(12) United States Patent
Kuo et al.

(10) Patent No.: US 7,750,048 B2
(45) Date of Patent: Jul. 6, 2010

(54) GPR40 AGONISTS

(75) Inventors: Gee-Hong Kuo, Scotch Plains, NJ (US);
Fengbin Song, Princeton, NJ (US);
Joseph Gunnet, Flemington, NJ (US);
Keith Demarest, Flemington, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 75 days.

(21) Appl. No.: 11/939,039

(22) Filed: Nov. 13, 2007

(65) Prior Publication Data

US 2008/0176912 A1    Jul. 24, 2008

Related U.S. Application Data

(60) Provisional application No. 60/865,940, filed on Nov. 15, 2006.

(51) Int. Cl.
*A61K 31/192* (2006.01)
*C07C 59/64* (2006.01)

(52) U.S. Cl. ..................... 514/570; 562/468

(58) Field of Classification Search .......... 514/365, 514/570, 372, 374, 438, 461; 548/203, 235; 549/79, 499; 562/465
See application file for complete search history.

(56) References Cited

U.S. PATENT DOCUMENTS

| | | | |
|---|---|---|---|
| 4,962,117 | A | 10/1990 | Young et al. |
| 5,102,881 | A | 4/1992 | Zamboni et al. |
| 5,232,916 | A | 8/1993 | Zamboni et al. |
| 5,266,718 | A | 11/1993 | Wierzbicki et al. |
| 5,439,869 | A | 8/1995 | Klung et al. |
| 5,605,914 | A | 2/1997 | Muller |
| 5,622,977 | A * | 4/1997 | Warrellow et al. .......... 514/336 |
| 5,698,579 | A | 12/1997 | Muller |
| 5,877,200 | A | 3/1999 | Muller |
| 6,071,856 | A | 6/2000 | Baker et al. |
| 6,075,041 | A | 6/2000 | Muller |
| 6,200,987 | B1 | 3/2001 | Muller |
| 6,479,554 | B2 | 11/2002 | Muller et al. |
| 7,314,888 | B1 | 1/2008 | Chaki et al. |
| 2003/0144325 | A1 | 7/2003 | Muller et al. |
| 2003/0216480 | A1 | 11/2003 | Holtzman |
| 2006/0004012 | A1 | 1/2006 | Akerman et al. |
| 2008/0021069 | A1 | 1/2008 | Itoh et al. |

FOREIGN PATENT DOCUMENTS

| | | |
|---|---|---|
| EP | 0501876 A1 | 2/1992 |
| EP | 1127869 A1 | 8/2001 |
| EP | 1484304 A1 | 8/2004 |
| WO | WO 95/01348 A2 | 1/1995 |

OTHER PUBLICATIONS

Vippagunta et al., Crystalline solids, 2001, Advanced Drug Delivery Reviews, 48, pp. 3 and 18.*
Arner, P., "The adipocyte in insulin resistance: key molecules and the impact of the thiazolidinediones.", Trends in Endocrinology and Metabolism, Apr. 2003, vol. 14(3), pp. 137-145.
Berge et al., "Pharmaceutical Salts.", J. Pharm.Sci., 1977, vol. 66(1), pp. 1-19.
Boden, G.,"Role of Fatty Acids in the Pathogenesis of Insulin Resistance and NIDDM.", Diabetes, 1997, vol. 46(1), pp. 3-10.
Briscoe et al., "The Orphan G Protein-coupled Receptor GPR40 Is Activated by Medium and Long Chain Fatty Acids.", J. of Biological Chemistry, 2003, vol. 278(13), pp. 11303-11311, USA.
Brown et al., "The Orphan G Protein-coupled Receptors GPR41 and GPR43 Are Activated by Propionate and Other Short Chain Carboxylic Acids*.", J. of Biological Chemistry, 2003, vol. 278(13), pp. 11312-11319, USA.
Gould P.L., "Salt Selection for Basic Drugs.", International J. Pharm., 1986, vol. 33, pp. 201-217.
Itoh et al., "Free fatty acids regulate insulin secretion from pancreatic β cells through CPR40.", Nature, Mar. 2003, vol. 422, pp. 173-176.
Kotarsky et al., "A human cell surface receptor activated by free fatty acids and thiazolidinedione drugs.", Biochem. and Biophysical Research Communications, 2003, vol. 301, pp. 406-410.
Sawzdargo et al., "A Cluster of Four Novel Human G Protein-Coupled Receptor Genes Occurring in Close Proximity to CD22 Gene on Chromosome 19q13.1.", Biochemical and Biophysical Research Communications, 1997, vol. 239(2), pp. 543-547.
Still et al., "Rapid Chromatographic Technique for Preparative Separations with Moderate Resolution.", J. Org. Chem., 1978, vol. 43(14), pp. 2923-2925.

* cited by examiner

*Primary Examiner*—Kamal A Saeed
*Assistant Examiner*—Kristin Bianchi

(57) ABSTRACT

The invention is directed to compounds of Formula (I) useful as GPR40 agonists. Pharmaceutical compositions and methods of treating one or more conditions including, but not limited to, insulin resistance, hyperglycemia, obesity, diabetes such as NIDDM, and other disorders related to lipid metabolism, energy homeostasis, and complications thereof, using compounds of the invention are also described.

17 Claims, No Drawings

GPR40 AGONISTS

CROSS-REFERENCE TO RELATED APPLICATIONS

This application claims priority to U.S. Provisional Patent Application No. 60/865,940, filed Nov. 15, 2006, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

Free fatty acid (FFA) can directly affect insulin release and indirectly affect insulin sensitivity. In search for novel G-protein coupled receptors (GPCRs), four FFA receptors were discovered, sequenced and de-orphanized. GPR41 was discovered in 1997 and initially cloned from rat lung while the human GPR41 sequence was published later the same year as part of an effort to identify galanin GPCR subtypes (Sawzdargo, M., et al., Biochemical and Biophysical Research Communications, 1997. 239(2): p. 543-7). Four GPCRs were identified (GPR40, GPR41, GPR42 and GPR43) and found as a cluster near chromosome 19q13.1. The receptors fall within the same GPCR subfamily but do not share a great deal of homology and differ in their tissue distributions and ligand specificities. While GPR40, GPR41 and GPR43 are functional receptors activated by various FFAs, GPR42 is non-functional and is thought to be the product of a polymorphic gene insert (Brown, A. J., et al., Journal of Biological Chemistry, 2003. 278(13): p. 11312-11319).

GPR40 is specifically activated by medium to long chain FFAs and signals through Gq protein coupling (Briscoe, C. P., et al., Journal of Biological Chemistry, 2003. 278(13): p. 11303-11311; Kotarsky, K., et al., Biochemical and Biophysical Research Communications, 2003. 301(2): p. 406-410). The tissue distribution as determined by rtPCR (reverse transcription Polymerase Chain Reaction) found that pancreas and brain expressed far more GPR40 than any other tissue (Briscoe, C. P., et al., Journal of Biological Chemistry, 2003. 278(13): p. 11303-11311; Kotarsky, K., et al., Biochemical and Biophysical Research Communications, 2003. 301(2): p. 406-410; Itoh, Y., et al., Nature, 2003. 422: p. 173-176). No expression of GPR40 was found in human peripheral blood mononucleocytes, B-lymphocytes or neutrophils (Briscoe, C. P., et al., Journal of Biological Chemistry, 2003. 278(13): p. 11303-11311). Within the pancreas, the expression was localized to the islets. Double staining with in situ hybridization in rat pancreas found GPR40 expression in those cells staining for insulin (β-cells) but not glucagon (α cells) (Itoh, Y., et al., Nature, 2003. 422: p. 173-176). Further supporting the islet specificity of GPR40 is the fact that both murine MIN6 and rat INS-1E pancreatic β-cell lines express GPR40 homologues and display an intracellular calcium response to long chain FFAs (Briscoe, C. P., et al., Journal of Biological Chemistry, 2003. 278(13): p. 11303-11311; Kotarsky, K., et al., Biochemical and Biophysical Research Communications, 2003. 301(2): p. 406-410). Long chain FFAs also stimulate insulin secretion from MIN6 cells in vitro. Insulin secretion is greater in the presence of high glucose indicating that FFAs amplify glucose-stimulated insulin release. To relate the expression of GPR40 to an in vivo state, the expression of the murine GPR40 homologue was compared in the pancreas of obese ob/ob mice and lean mice. In whole pancreas GPR40 was 6.5 fold greater in the ob/ob mice.

Adipose tissue plays an active role in energy balance far beyond that of simple energy storage. Elevated blood levels of FFA are common in obese and diabetic patients and have been implicated in insulin resistance and reduced glucose uptake. There is an enormous body of evidence relating FFAs to obesity, the metabolic syndrome and diabetes (see, e.g., Boden, G., Diabetes, 1997. 46(1): p. 3-10; Arner, P., Trends in Endocrinology and Metabolism, 2003. 14(3): p. 137-145). There is a continuing need for new GPR40 agonists, which can activate the pancreatic GPR40 receptor and stimulate glucose-induced insulin secretion. There is a further need for new GPR40 agonists that are efficacious in both lean and obese subjects. There is a further need for new GPR40 agonists for the treatment of insulin resistance, hyperglycemia, obesity, diabetes such as Non-insulin Dependent Diabetes Mellitus (NIDDM), and other disorders related to lipid metabolism, energy homeostasis, and complications thereof.

SUMMARY OF THE INVENTION

In one aspect, the present invention is directed to a compound of Formula (I):

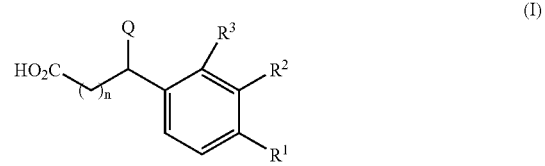

wherein
$R^1$ is —O—$R^4$, or when $R^2$ is —O—$R^5$, $R^1$ is H;
$R^2$ is selected from H, halo, cyano, acetyl, $C_{1-3}$alkyl optionally substituted with halo, $C_{1-3}$alkoxy optionally substituted with halo, and —O—$R^5$;
$R^3$ is selected from H, halo, cyano, acetyl, $C_{1-3}$alkyl optionally substituted with halo, and $C_{1-3}$alkoxy optionally substituted with halo;
$R^4$ and $R^5$ are each independently selected from $C_{3-8}$alkyl optionally substituted with halo or cyano, $C_{3-8}$alkenyl optionally substituted with halo, $C_{3-8}$alkynyl optionally substituted with halo, $C_{3-8}$cycloalkyl optionally substituted with $C_{1-3}$alkyl, $C_{1-4}$alkoxy-$C_{3-5}$alkyl;
Q is selected from phenyl,

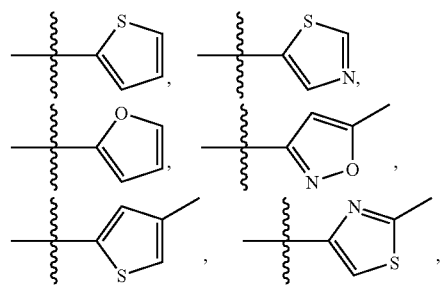

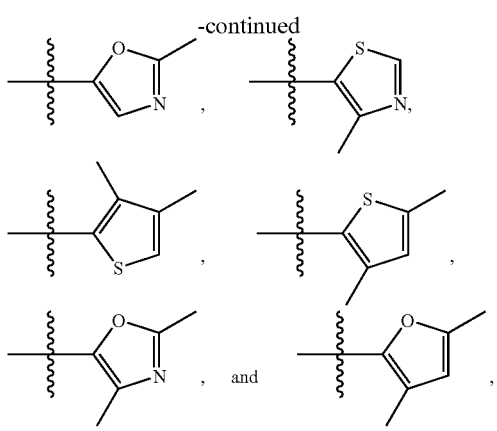

said Q being substituted with 0-2 groups independently selected from halo, $C_{1-3}$alkyl, halo substituted $C_{1-3}$alkyl, $C_{1-3}$alkoxy, halo substituted $C_{1-3}$alkoxy, cyano, acetyl or hydroxy; and n is 1, 2 or 3;

or an optical isomer, enantiomer, diastereomer, racemate, or pharmaceutically acceptable salt or solvate thereof.

In another aspect, the present invention is directed to pharmaceutical compositions containing one or more compounds, pharmaceutically acceptable salts or solvates of Formula (I) as described herein admixed with a pharmaceutically acceptable carrier, excipient or diluent, wherein the compositions can be used to treat a condition directly or indirectly mediated by GPR40.

In yet another aspect, the present invention is directed to a method of treating or preventing a disease or condition in a mammal which disease or condition is affected by the modulation of GPR40, which method comprises administering to a mammal in need of such treatment or prevention a therapeutically effective amount of a compound of Formula (I) or a pharmaceutically acceptable salt or solvate thereof as described herein.

In a further aspect, the present invention is directed to a method for treating or preventing a disease or condition selected from insulin resistance, hyperglycemia, obesity, diabetes such as NIDDM, and other disorders related to lipid metabolism, energy homeostasis, and complications thereof, said method comprising the step of administering to a mammal in need of such treatment a therapeutically effective amount of a compound of Formula (I) or a pharmaceutically acceptable salt or solvate thereof as described herein.

In still a further aspect, the present invention is directed to a kit comprising in one or more containers an amount of the compound of Formula (I) effective to treat or prevent a disease or condition selected from insulin resistance, hyperglycemia, obesity, diabetes such as NIDDM, and other disorders related to lipid metabolism, energy homeostasis, and complications thereof.

DETAILED DESCRIPTION OF THE INVENTION

The invention features compounds of Formula (I), pharmaceutically acceptable salts or solvates thereof, compositions containing the same, and methods of using them.

Compounds of the invention are GPR40 agonists, that preferably are useful for treating preventing or inhibiting the progression of a disease or condition which is directly or indirectly mediated by GPR40. Examples of a condition intended to be within the scope of the present invention include, but are not limited to, insulin resistance, hyperglycemia, obesity, diabetes such as NIDDM, and other disorders related to lipid metabolism and energy homeostasis complications thereof.

As used herein, the following underlined terms are intended to have the following meanings unless otherwise noted:

With reference to substituents, the term "independently" means that when more than one of such substituent is possible, such substituents may be the same or different from each other.

With reference to substituents, the term "optionally substituted" means one or more hydrogen atoms, preferably one to three hydrogen atoms can be each independently replaced with the same or different substituent(s).

"$C_{i-j}$" (where i and j are integers) refers to a radical containing from i to j carbon atoms inclusive. For example, $C_{1-3}$ denotes a radical containing 1, 2 or 3 carbon atoms.

"Alkyl" refers to a straight or branched chain monovalent hydrocarbon radical derived by the removal of one hydrogen atom from a single carbon atom of a parent alkane. Typical alkyl groups include, but are not limited to, methyl; ethyl; propyl; butyl, 2-methyl-propyl, 2-methyl-prop-2-yl, etc.; and the like.

"Cycloalkyl" can be, for example, $C_{3-10}$cycloalkyl; preferably, cycloalkyl is $C_{3-8}$cycloalkyl. Examples of such cycloalkyl rings include cyclopropyl, cyclobutyl, cyclopentyl, or cyclohexyl.

"Alkenyl" refers to a straight or branched chain monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, etc.; and the like.

"Alkynyl" refers to a straight or branched chain monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy" refers to oxygen ethers formed from the previously described straight, branched chain alkyl groups.

"Halogen" or "halo" refers to iodo (I), bromo (Br), chloro (Cl), and fluoro (F).

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Throughout this disclosure, the terminal portion of the designated side chain is described first, followed by the adjacent functionality toward the point of attachment. Thus, for example, a "phenyl$C_{1-6}$alkylaminocarbonyl$C_{1-6}$alkyl" substituent refers to a group of the formula:

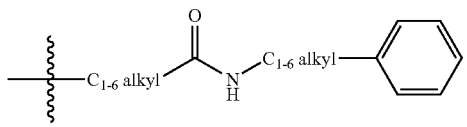

The present invention is directed to a compound of Formula (I):

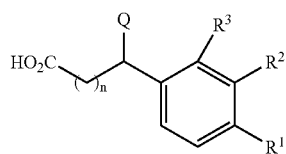

wherein $R^1$ is —O—$R^4$, or when $R^2$ is —O—$R^5$, $R^1$ is H;

$R^2$ is selected from H, halo, cyano, acetyl, $C_{1-3}$alkyl optionally substituted with halo, $C_{1-3}$alkoxy optionally substituted with halo, and —O—$R^5$;

$R^3$ is selected from H, halo, cyano, acetyl, $C_{1-3}$alkyl optionally substituted with halo, and $C_{1-3}$alkoxy optionally substituted with halo;

$R^4$ and $R^5$ are each independently selected from $C_{3-8}$alkyl optionally substituted with halo or cyano, $C_{3-8}$alkenyl optionally substituted with halo, $C_{3-8}$alkynyl optionally substituted with halo, $C_{3-8}$cycloalkyl optionally substituted with $C_{1-3}$alkyl, $C_{1-4}$alkoxy-$C_{3-5}$alkyl;

Q is selected from phenyl,

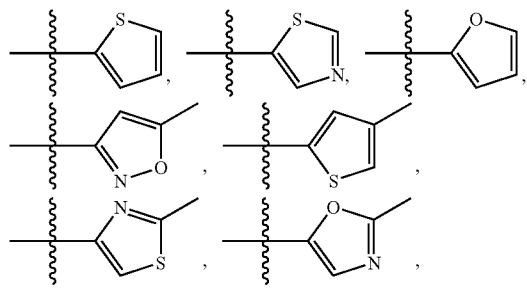

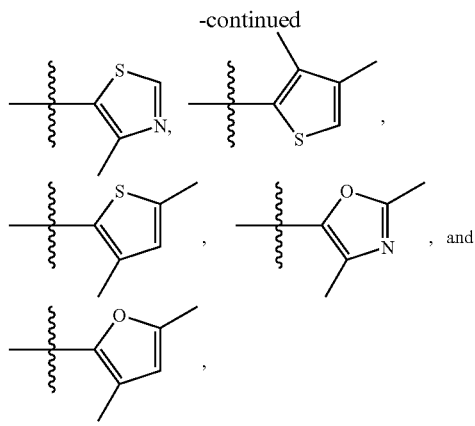

said Q being substituted with 0-2 groups independently selected from halo, $C_{1-3}$alkyl, halo substituted $C_{1-3}$alkyl, $C_{1-3}$alkoxy, halo substituted $C_{1-3}$alkoxy, cyano, acetyl or hydroxy; and n is 1, 2 or 3;

or an optical isomer, enantiomer, diastereomer, racemate, or pharmaceutically acceptable salt or solvate thereof.

Particularly, the present invention features a compound of Formula (I) wherein $R^1$ is —O—$R^4$, wherein $R^4$ is selected from $C_{3-7}$alkyl optionally substituted with halo, methoxy-$C_{3-5}$ alkyl-, $C_{3-8}$alkenyl, and $C_{5-6}$cycloalkyl optionally substituted with methyl.

Particularly, the present invention features a compound of Formula (I) wherein $R^2$ and $R^3$ are both H.

Particularly, the present invention features a compound of Formula (I) wherein Q is phenyl or

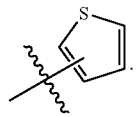

More particularly, Q is phenyl.

Particularly, the present invention features a compound of Formula (I) wherein Q is substituted with 0-2 groups selected from halo, $CF_3$, and OH.

Particularly, the present invention features a compound of Formula (I) wherein n is 1.

In particular, the present invention is directed to a compound of Formula (I) wherein:

$R^1$ is —O—$R^4$;

$R^2$ is selected from H, halo, cyano, acetyl, $C_{1-3}$alkyl optionally substituted with halo, and $C_{1-3}$alkoxy optionally substituted with halo;

$R^3$ is selected from H, halo, cyano, acetyl, $C_{1-3}$alkyl optionally substituted with halo, and $C_{1-3}$alkoxy optionally substituted with halo;

$R^4$ is selected from $C_{3-8}$alkyl optionally substituted with halo or cyano, $C_{3-8}$alkenyl optionally substituted with halo, $C_{3-8}$alkynyl optionally substituted with halo, $C_{3-8}$cycloalkyl optionally substituted with $C_{1-3}$alkyl, $C_{1-4}$alkoxy-$C_{3-5}$alkyl;

Q is selected from phenyl,

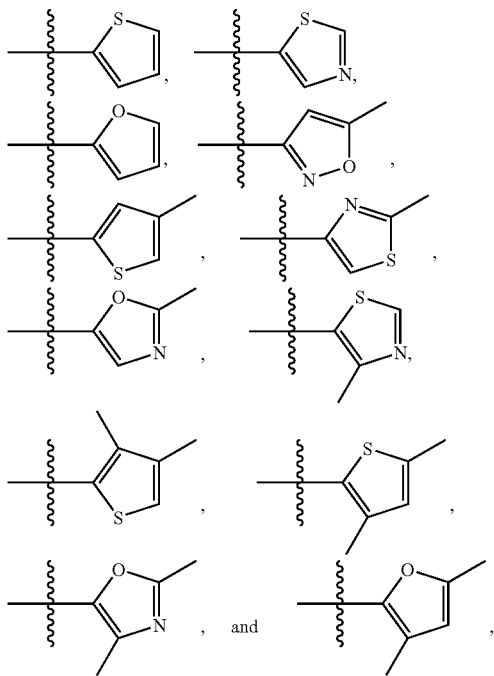

said Q being substituted with 0-2 groups independently selected from halo, $C_{1-3}$alkyl, halo substituted $C_{1-3}$alkyl, $C_{1-3}$alkoxy, halo substituted $C_{1-3}$alkoxy, cyano, acetyl or hydroxy; and
n is 1;

or an optical isomer, enantiomer, diastereomer, racemate, or pharmaceutically acceptable salt or solvate thereof.

Particularly, $R^1$ is —O—$R^4$, wherein $R^4$ is selected from $C_{3-7}$alkyl optionally substituted with halo, methoxy-$C_{3-5}$alkyl-, $C_{3-8}$alkenyl, and $C_{5-6}$cycloalkyl optionally substituted by methyl;
$R^2$ and $R^3$ are both H; and
Q is phenyl or

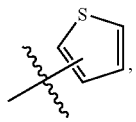

said Q being optionally substituted with 1 or 2 groups independently selected from halo, $CF_3$, or OH.

In particular, the present invention is also directed to a compound of Formula (I) wherein:
$R^1$ is H;
$R^2$ is —O—$R^5$;
$R^3$ is H; and
Q is phenyl or

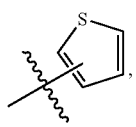

said Q being optionally substituted with 1 or 2 groups independently selected from halo, $CF_3$, or OH;

or an optical isomer, enantiomer, diastereomer, racemate, or pharmaceutically acceptable salt or solvate thereof. Particularly, n is 1.

The present invention is further directed to compositions comprising a compound of Formula (I) for use as a GPR40 agonists:

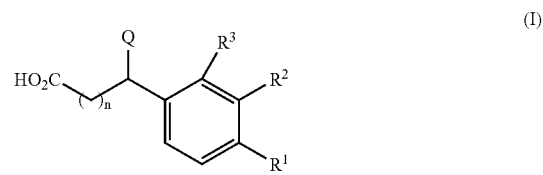

wherein
$R^1$ is —O—$R^4$, or when $R^2$ is —$R^5$, $R^1$ is H;
$R^2$ is selected from H, halo, cyano, acetyl, $C_{1-3}$alkyl optionally substituted with halo, $C_{1-3}$alkoxy optionally substituted with halo, and —O—$R^5$;
$R^3$ is selected from H, halo, cyano, acetyl, $C_{1-3}$alkyl optionally substituted with halo, and $C_{1-3}$alkoxy optionally substituted with halo;
$R^4$ and $R^5$ are each independently selected from $C_{3-8}$alkyl optionally substituted with halo or cyano, $C_{3-8}$alkenyl optionally substituted with halo, $C_{3-8}$alkynyl optionally substituted with halo, $C_{3-8}$cycloalkyl optionally substituted with $C_{1-3}$alkyl, $C_{1-4}$alkoxy-$C_{3-5}$alkyl;
Q is selected from phenyl,

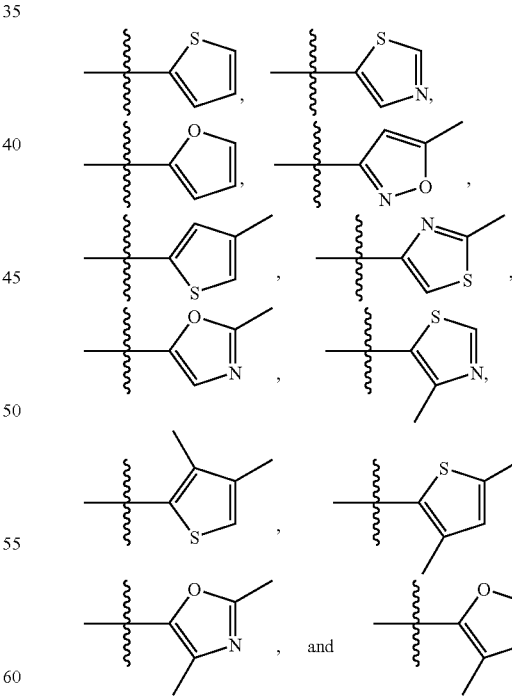

said Q being substituted with 0-2 groups independently selected from halo, $C_{1-3}$alkyl, halo substituted $C_{1-3}$alkyl, $C_{1-3}$alkoxy, halo substituted $C_{1-3}$alkoxy, cyano, acetyl or hydroxy; and
n is 1, 2 or 3;

or an optical isomer, enantiomer, diastereomer, racemate, or pharmaceutically acceptable salt or solvate thereof.

In particular, the present invention is directed to a compound of Formula (I) wherein $R^1$ is —O—$R^4$, wherein $R^4$ is selected from —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH$_2$CH$_2$CH$_2$CH$_2$CH$_3$, —CH$_2$CH$_2$CH$_2$CF$_3$, —CH$_2$CH$_2$CH(CH$_3$)$_2$, —CH$_2$CH$_2$C(CH$_3$)=CH$_2$, —CH$_2$CH=CHCH$_3$, —CH$_2$CH$_2$CH$_2$—O—CH$_3$, —CH$_2$CH(CH$_2$CH$_3$)$_2$, —CH$_2$CH(CH$_3$)CH$_2$CH$_3$, or 4-methylcyclohexyl;

$R^2$ and $R^3$ are both H; and

Q is phenyl,

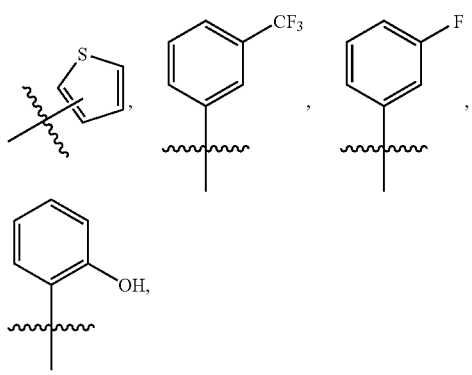

or an optical isomer, enantiomer, diastereomer, racemate, or pharmaceutically acceptable salt or solvate thereof.

In particular, the present invention is directed to a compound selected from the group consisting of:

3-Phenyl-3-(4-propoxy-phenyl)-propionic acid;
3-(4-Butoxy-phenyl)-3-phenyl-propionic acid;
3-(4-Pentyloxy-phenyl)-3-phenyl-propionic acid;
3-(4-Hexyloxy-phenyl)-3-phenyl-propionic acid;
3-(4-Heptyloxy-phenyl)-3-phenyl-propionic acid;
3-Phenyl-3-[4-(4,4,4-trifluoro-butoxy)-phenyl]-propionic acid;
3-[4-(3-Methyl-but-3-enyloxy)-phenyl]-3-phenyl-propionic acid;
3-[4-(3-Methyl-butoxy)-phenyl]-3-phenyl-propionic acid;
3-[4-(3-methoxy-propoxy)-phenyl]-3-phenyl-propionic acid;
3-(3-Pentyloxy-phenyl)-3-phenyl-propionic acid;
5-(4-Butoxy-phenyl)-5-phenyl-pentanoic acid;
3-(4-But-2-enyloxy-phenyl)-3-phenyl-propionic acid;
3-[4-(4-Methyl-cyclohexyloxy)-phenyl]-3-phenyl-propionic acid;
3-[4-(2-Ethyl-butoxy)-phenyl]-3-phenyl-propionic acid;
3-[4-(2-Methyl-butoxy)-phenyl]-3-phenyl-propionic acid;
3-(4-Butoxy-phenyl)-3-(3-fluoro-phenyl)-propionic acid;
3-(4-Butoxy-phenyl)-3-(3-trifluoromethyl-phenyl)-propionic acid;
3-(4-Butoxy-phenyl)-3-(2-hydroxy-phenyl)-propionic acid;
3-(4-Butoxy-phenyl)-3-thiophen-2-yl-propionic acid;
3-[4-(2-Methoxy-ethoxy)-phenyl]-3-phenyl-propionic acid;
3-[4-(1-Ethyl-propoxy)-phenyl]-3-phenyl-propionic acid;
3-(4-Butoxy-phenyl)-3-(4-trifluoromethoxy-phenyl)-propionic acid;
3-(4-Butoxy-phenyl)-3-(4-trifluoromethyl-phenyl)-propionic acid;
3-[4-(3,3-Dimethyl-butoxy)-phenyl]-3-phenyl-propionic acid; and an optical isomer, enantiomer, diastereomer, racemate, or pharmaceutically acceptable salt or solvate thereof.

In particular, the present invention is directed to a compound of Formula (I) selected from the compounds shown in Table 1 below and an optical isomer, enantiomer, diastereomer, racemate, or pharmaceutically acceptable salt or solvate thereof.

More particularly, the present invention is directed to a compound of Formula (I) selected from:

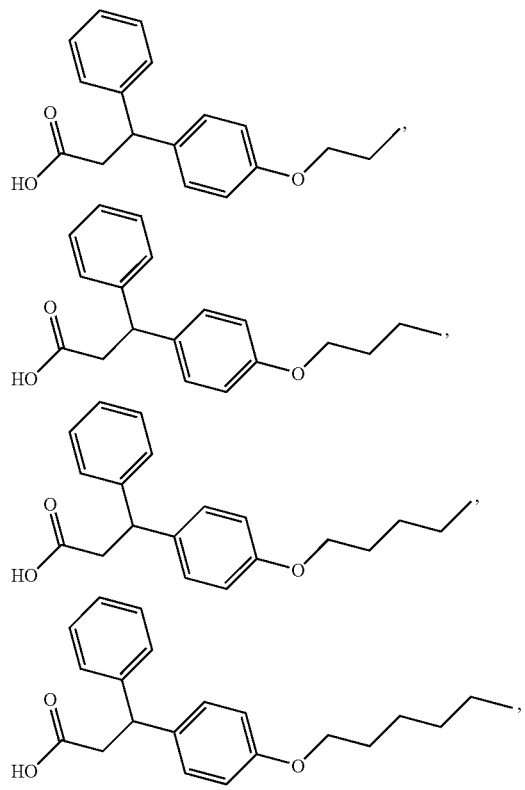

and an optical isomer, enantiomer, diastereomer, racemate, or pharmaceutically acceptable salt or solvate thereof.

In another aspect, the present invention is directed to pharmaceutical compositions containing one or more compounds of Formula (I) or pharmaceutically acceptable salts or solvates thereof as described herein admixed with a pharmaceutically acceptable carrier, excipient or diluent, wherein the compositions can be used to treat a condition directly or indirectly mediated by GPR40. More particularly, said pharmaceutical composition contains a compound selected from the group consisting of

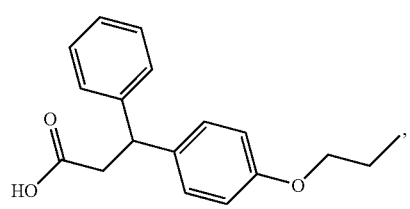

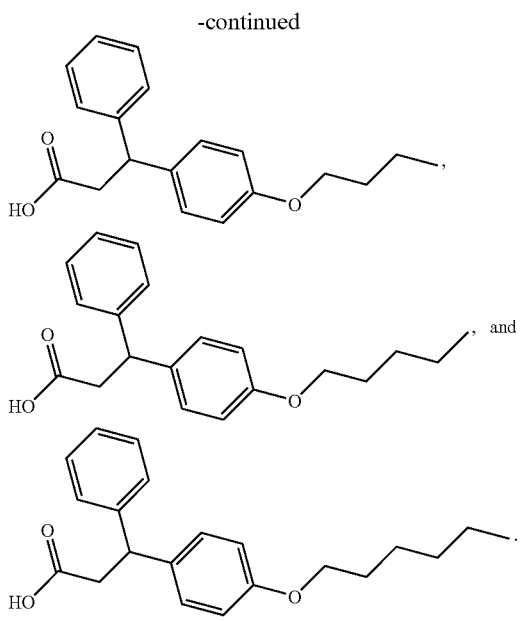

The present invention is also directed to a method of treating or preventing a disease or condition in a subject, particularly a mammal including human, which disease or condition is affected by the modulation of GPR40. In particular, the method comprises administering to a subject in need of such treatment or prevention a therapeutically effective amount of a compound of Formula (I). More particularly, this invention provides a method of stimulating glucose-induced insulin secretion in a subject, which method comprises administering to a subject in need thereof a therapeutically effective amount of a compound of Formula (I) or a pharmaceutically acceptable salt or solvate thereof. Specifically, said therapeutically effective amount comprises a dose range of from about 0.1 mg to about 2,000 mg. More specifically, said therapeutically effective amount comprises a dose range of from about 1 mg to about 1000 mg, preferably about 50 mg to about 1000 mg.

In a further aspect, the present invention is directed to a method for treating or preventing a disease or condition selected from the group consisting of insulin resistance, hyperglycemia, obesity, diabetes, and other disorders related to lipid metabolism, energy homeostasis and complications thereof, said method comprising the step of administering to a mammal in need of such treatment a therapeutically effective amount of a compound of Formula (I).

In still a further aspect, the present invention is directed to a kit comprising in one or more containers an amount of the composition of Formula (I) effective to treat or prevent a disease or condition selected from insulin resistance, hyperglycemia, obesity, diabetes such as NIDDM, and other disorders related to lipid metabolism and energy homeostasis complications thereof.

Another embodiment of the present invention is a composition comprising the dextrorotatory enantiomer of a compound of Formula (I), wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of Formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. Representative hydroxy group prodrug forms include, but are not limited to, $C_{1-4}$alkylethers, substituted $C_{1-4}$alkylethers, and $C_{1-4}$alkyl esters.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

In certain embodiments, the present invention is directed to a process for preparation of the compounds of Formula (I).

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

For example, in certain examples herein, racemic mixture D-1 was resolved by chiral HPLC to give enantiomer A (shorter retention time) and enantiomer B (longer retention time). The absolute stereochemistry of enantiomers A and B can be further determined according to known procedures or methods in the art.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood. Other ingredients may be added to increase solubility or preservation. Injectable suspensions or solutions may also be prepared utilizing aqueous carriers along with appropriate additives.

For buccal or sublingual administration the compositions may be administered in the form of tablets or lozenges which can be formulated in a conventional manner.

For liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption Advantageously, compounds of the present invention may be administered in a single daily dose, or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as GPR40 agonists is required for a subject in need thereof.

The invention also provides a pharmaceutical pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

For oral administration, a pharmaceutical composition is preferably provided in the form of tablets containing 0.1, 10.0, 50.0, 100, 150, 200, 250, and 500 milligrams of the active ingredient for the symptomatic adjustment of the dosage to the subject to be treated.

In regard to the use of the present compounds in treatment of the diseases or conditions such as those listed above, a therapeutically effective dose can be determined by persons skilled in the art by the use of established animal models. Such a dose would likely fall in the range of from about 0.1 mg to about 2,000 mg, preferably from about 1 to about 1000 mg, more preferably from about 50 mg to about 1000 mg of active ingredient administered 1 to 4 times per day for an average (70 kg) human.

General Synthetic Methods

Representative compounds of the present invention can be synthesized in accordance with the general synthetic methods described below as well as the illustrative examples that follow. Since the schemes are an illustration only, the invention should not be construed as being limited by the chemical reactions and conditions expressed. The preparation of the various starting materials used in the schemes is well within the skill of persons versed in the art.

In accordance with Schemes 1a and 1b, wherein Q, $R^2$, $R^3$, $R^4$, and $R^5$ are as described herein, R" is alkyl, and M is metal, compounds A and A' are converted to compounds of Formula (Ia) and (Ia'), respectively.

$Et_3SiH$ in $TFA/CH_2Cl_2$. Treatment of the phenol methyl ether compound C with a demethylation reagent such as a $BBr_3$ in a solvent such as $CH_2Cl_2$ gives compound D. Compound D can also be prepared by Rhodium-catalyzed conjugated addition of Q-M (aryl silane, aryl tin or aryl boronic acid) to α,β-unsaturated ester E. Compound D is converted to compound F either through a) alkylation with alkyl halide $R^4X$ in the presence of an appropriate base such as CsF, in a suitable

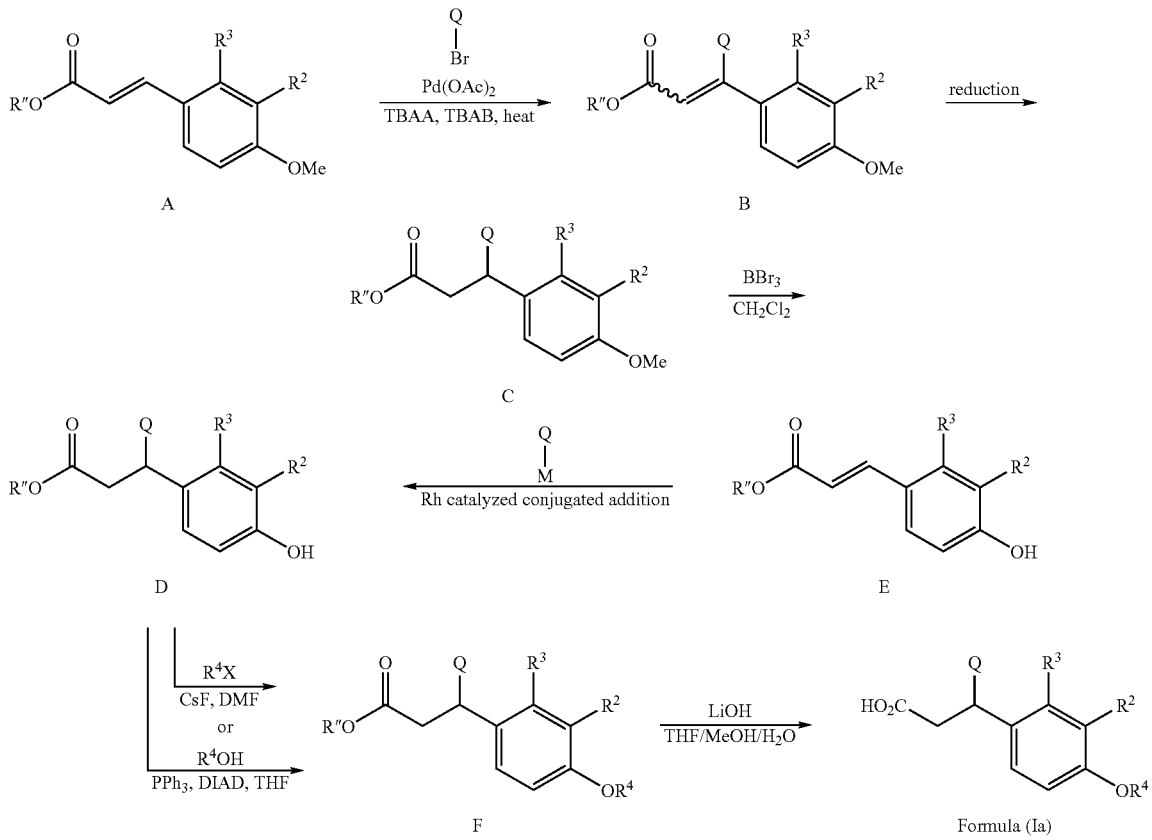

In Scheme 1a, A is coupled with aryl bromide Q-Br to form compound B employing an agent such as $Pd(OAc)_2$ as the catalyst in the presence of a base such as TBAA with molten TBAB as the solvent. The C=C double bond of compound B α,β-unsaturated ester is saturated to give compound C either by Pd catalyzed hydrogenation or by silane reduction such as solvent such as DMF, or b) through coupling with the corresponding alkyl alcohol $R^4OH$ under standard Mitsunobu reaction conditions. Under basic conditions such as LiOH in an aqueous alcoholic solvent system such as $THF/MeOH/H_2O$, saponification of compound F provides compounds of Formula (Ia).

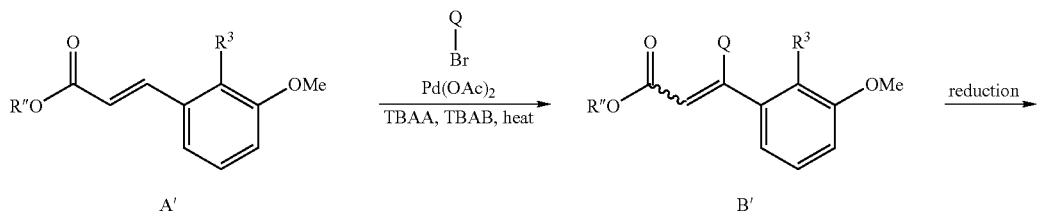

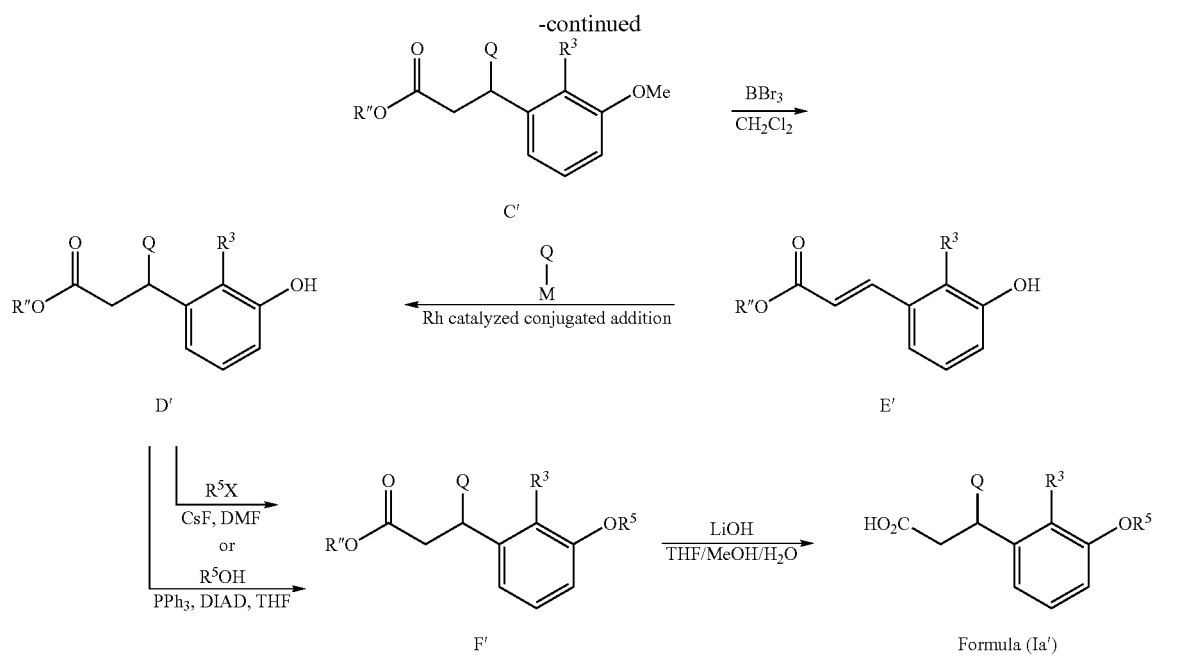

Similarly, compounds A' are converted to compounds of Formula (Ia') as described in Scheme 1b.

Compounds of Formula (Ib) and (Ib') can be made following Schemes 2a and 2b, respectively:

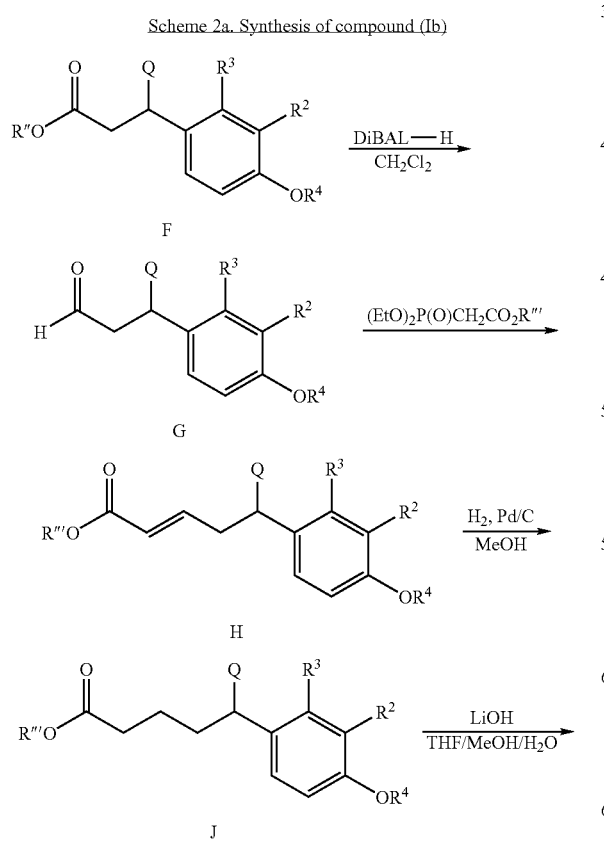

In scheme 2a, wherein Q, $R^2$, $R^3$, and $R^4$ are as described herein, and R" and R'" are independently alkyl, ester F, which is prepared as described above, is reduced to aldehyde G using a reducing reagent such as DiBAL-H in a suitable solvent such as $CH_2Cl_2$. Extension of the aldehyde G to α,β-unsaturated ester H is achieved by reaction with phosphonate such as $(EtO)_2P(O)CH_2CO_2R'''$, in the presence of a base such as NaH, in an aprotic solvent such as THF. Hydrogenation of compound H using a metal catalyst such as Pd/C, under $H_2$ in a suitable solvent such as MeOH, gives compound J. Under basic conditions such as LiOH in an aqueous alcoholic solvent system such as $THF/MeOH/H_2O$, saponification of ester J provides compound (Ib).

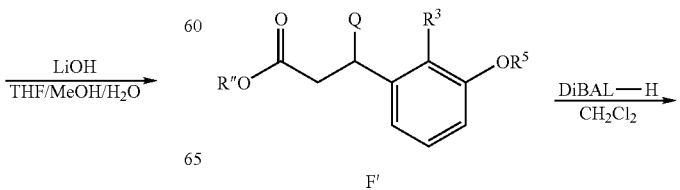

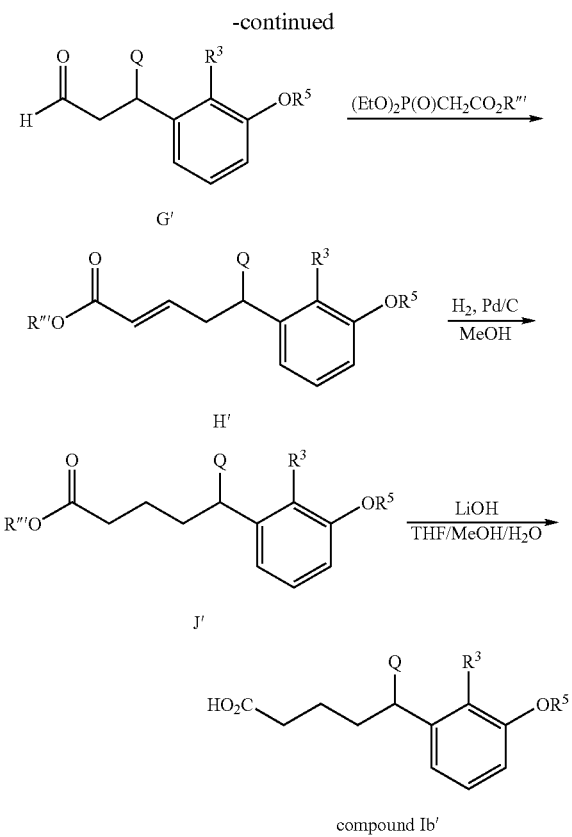

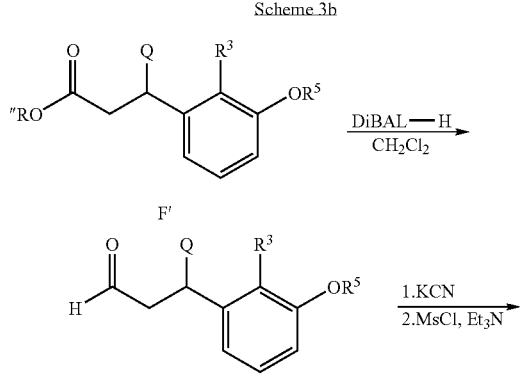

Similarly, compounds F' are converted to compounds of Formula (Ib') as described in Scheme 2b wherein Q, $R^3$, and $R^5$ are as described herein, and R" and R"' are independently alkyl.

Compounds of Formula (Ic) and (Ic') can be made following Schemes 3a and 3b, respectively:

In scheme 3a, wherein Q, R", $R^2$, $R^3$, and $R^4$ are as described herein, ester F, which is prepared as described above, is converted to G using a reducing reagent such as DiBAL-H. Reaction of G with an agent such as KCN, followed by dehydration condition (e.g., MsCl, $Et_3N$) can give K. Hydrolysis (e.g., HCl, $H_2O$) of K can give L, which is followed by hydrogenation condition to give the compound (Ic).

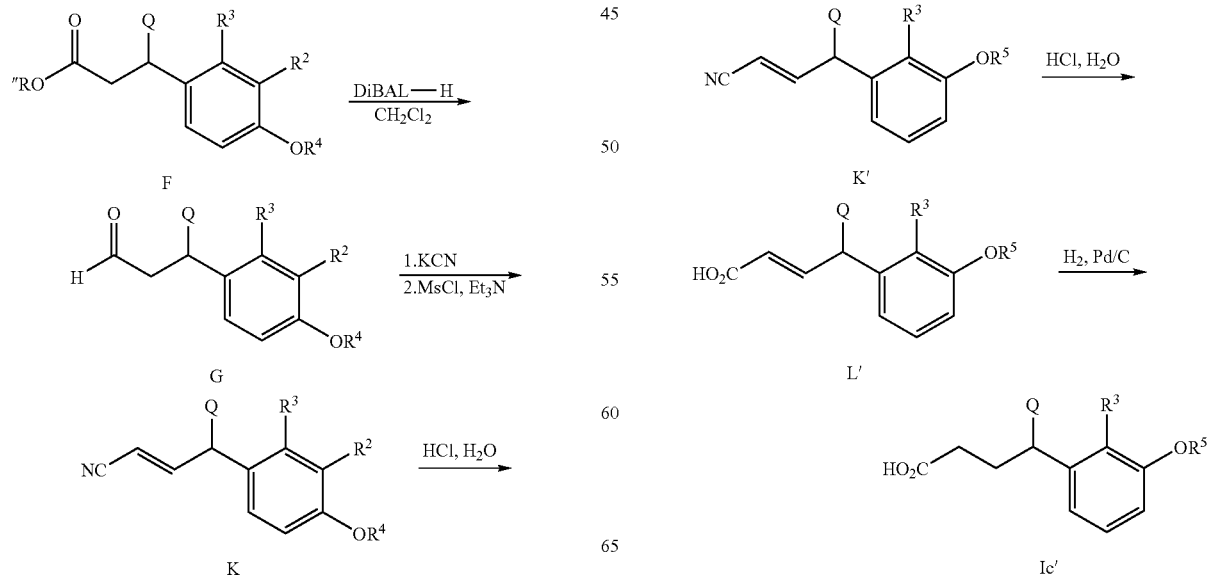

Similarly, compounds F' are converted to compounds of Formula (Ic') as described in Scheme 3b wherein Q, R", $R^3$, and $R^5$ are as described herein.

Compounds of Formula (I) that are chiral may be separated into their enantiomers by chromatography on a chiral stationary phase. Alternatively, the basic compounds of the present invention may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

abbreviations
Ac=$CH_3C(O)$—
Aq=aqueous
Cpd, Cmpd=compound
con=concentration
DCE=dichloroethane
DCM=dichloromethane
DIAD=diisopropyl azodicarboxlate
DiBAL-H=diisobutylaluminum hydride
DIEA=diisopropylethyl amine
DMF=N,N-dimethylformamide
DMSO=dimethylsulfoxide
DPPF=diphenylphosphinoferrocene
Et=ethyl
EtOAc=ethyl acetate
FDSS=Functional Drug Screening System
h or hr=hour(s)
HATU=N-[(dimethylamino)(3H-1,2,3-triazolo(4,5-b)pyridine-3-yloxy)methylene]-N-methylmethanaminium hexafluorophosphate
HDL=High Density Lipoprotein
HDL-C=high density lipoprotein cholesterol
IDL=Intermediate Density Lipoprotein
LAH=lithium aluminum hydride
LDL=Low Density Lipoprotein
LDL-C=Low Density Lipoprotein cholesterol
LiN(TMS)$_2$=Lithium bis(trimethylsilyl)amide
Me=methyl
min=minute(s)
NBS=N-bromosuccinimide
Ph=phenyl
PPA=polyphosphoric acid
psi=pascal per square inch Rf=retention time
RT or rt=room temperature
TBAA=tetrabutylammonium acetate
TBAB=tetrabutylammonium bromide
t-Boc=tert-butoxycarbonyl
TBSO=tert-butyldimethylsilyloxy
t-Bu=tert-butyl
TEA=triethylamine
TFA=trifluoroacetic acid
THF=tetrahydrofuran
TLC=(thin layer chromatography)
TMS=trimethylsilyl
TMSOTf=trimethylsilyl triflate
Tol=toluene
Ts=Tosylate
VLDL=Very Low Density Lipoprotein
Yb(OTf)$_3$=Ytterbium tristriflate

EXAMPLES

Example A

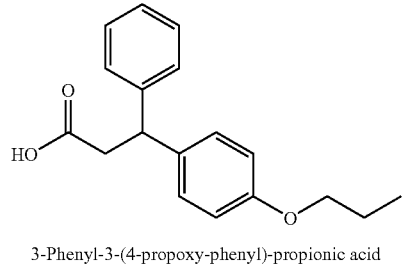

Compound 1

3-Phenyl-3-(4-propoxy-phenyl)-propionic acid

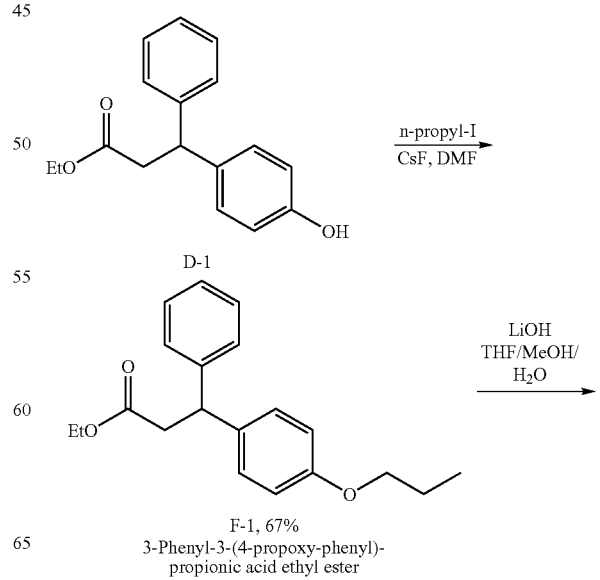

Scheme A

F-1, 67%
3-Phenyl-3-(4-propoxy-phenyl)-propionic acid ethyl ester

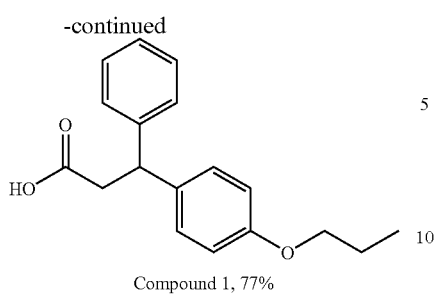

Compound 1, 77%

To a mixture of D-1 (189 mg, 0.70 mmol) in DMF (7 mL) with CsF (320 mg, 2.10 mmol) was added 1-iodopropane (143 mg, 0.84 mmol). The reaction was stirred at room temperature for overnight. Water was added and the mixture was extracted with EtOAc thrice. The combined extracts were washed with $H_2O$, brine and dried over $Na_2SO_4$. Concentration and chromatograph on silica gel (10:1 hexane/EtOAc) gave 146 mg (67%) of F-1 as colorless oil. $^1$H NMR (300 MHz, $CDCl_3$) δ7.30-7.10 (m, 7H), 6.81 (d, J=6.0 Hz, 2H), 4.49 (t, J=9.0 Hz, 1H), 4.00 (q, J=6.0 Hz, 2H), 3.87 (t, J=6.0 Hz, 2H), 3.01 (d, J=9.0 Hz, 2H), 1.77 (tq, J=6.0, 6.0 Hz, 2H), 1.11 (t, J=6.0 Hz, 3H), 1.01 (t, J=6.0 Hz, 3H); MS (ES) m/z: 335 (M+Na$^+$).

A solution of F-1 (128 mg, 0.41 mmol) in THF/MeOH/$H_2O$ (4:1:1 v/v/v, 12 mL) was treated with LiOH (1 M in $H_2O$, 2.0 mL, 2.0 mmol). The mixture was stirred at room temperature for overnight. Saturated $NH_4Cl$ aqueous solution was added and it was extracted with EtOAc thrice. The combined extracts were washed with brine and dried over $Na_2SO_4$. Concentration and chromatograph on silica gel (20:1 $CH_2Cl_2$/MeOH) gave 90 mg (77%) of the acid 1 as white solid. $^1$H NMR (300 MHz, $CDCl_3$) δ7.31-7.09 (m, 7H), 6.81 (d, J=6.0 Hz, 2H), 4.47 (t, J=9.0 Hz, 1H), 3.87 (t, J=6.0 Hz, 2H), 3.06 (d, J=9.0 Hz, 2H), 1.77 (tq, J=6.0 Hz, J=6.0 Hz, 2H), 1.01 (t, J=6.0 Hz, 3H); MS (ES) m/z: 307 (M+Na$^+$).

Example B

Compound 2

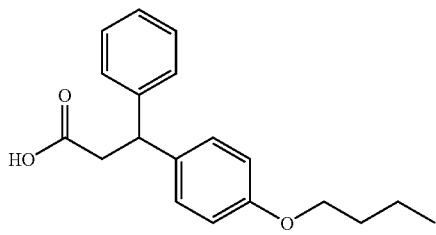

3-(4-Butoxy-phenyl)-3-phenyl-propionic acid

Scheme B

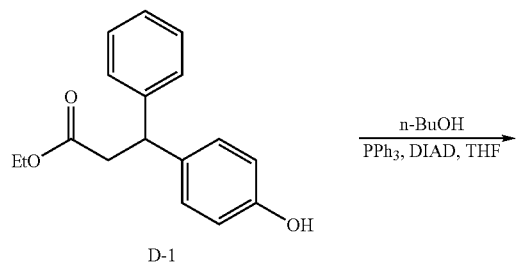

D-1

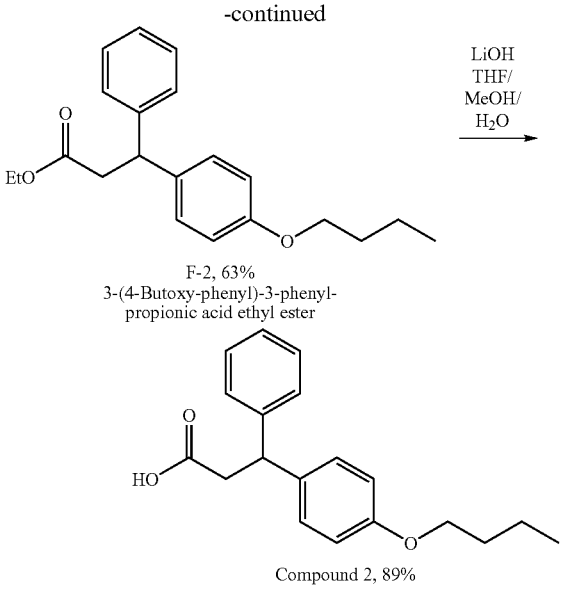

F-2, 63%
3-(4-Butoxy-phenyl)-3-phenyl-propionic acid ethyl ester

Compound 2, 89%

A solution of D-1 (135 mg, 0.50 mmol), 1-butanol (37 mg, 0.50 mmol) and PPh$_3$ (157 mg, 0.60 mmol) in THF (3 mL) was treated with DIAD (107 mg, 0.53 mmol). The reaction was stirred at room temperature for 7 h. Concentration and chromatograph on silica gel (20:1 hexane/EtOAc) gave 103 mg (63%) of F-2 as colorless oil. $^1$H NMR (300 MHz, $CDCl_3$) δ7.30-7.10 (m, 7H), 6.80 (d, J=6.0 Hz, 2H), 4.49 (t, J=6.0 Hz, 1H), 4.02 (q, J=6.0 Hz, 2H), 3.91 (t, J=6.0 Hz, 2H), 3.01 (d, J=6.0 Hz, 2H), 1.73 (tt, J=6.0, 6.0 Hz, 2H), 1.52-142 (m, 2H), 1.11 (t, J=6.0 Hz, 3H), 0.95 (t, J=6.0 Hz, 3H); MS (ES) m/z: 327 (M+H$^+$).

A solution of F-2 (80 mg, 0.24 mmol) in THF/MeOH/$H_2O$ (4:1:1 v/v/v, 12 mL) was treated with LiOH (1 M in $H_2O$, 2.0 mL, 2.0 mmol). The mixture was stirred at room temperature overnight. Saturated $NH_4Cl$ aqueous solution was added and it was extracted with EtOAc thrice. The combined extracts were washed with brine and dried over $Na_2SO_4$. Concentration and chromatograph on silica gel (20:1 $CH_2Cl_2$/MeOH) gave 65 mg (89%) of the acid 2 as white solid. $^1$H NMR (300 MHz, $CDCl_3$) δ7.31-7.09 (m, 7H), 6.80 (d, J=6.0 Hz, 2H), 4.46 (t, J=6.0 Hz, 1H), 3.90 (t, J=6.0 Hz, 2H), 3.04 (d, J=6.0 Hz, 2H), 1.74 (tt, J=6.0, 6.0 Hz, 2H), 1.46 (tq, J=6.0 Hz, J=6.0 Hz, 2H), 0.95 (t, J=6.0 Hz, 3H); MS (ES) m/z: 321 (M+Na$^+$).

Example C

Compound 3

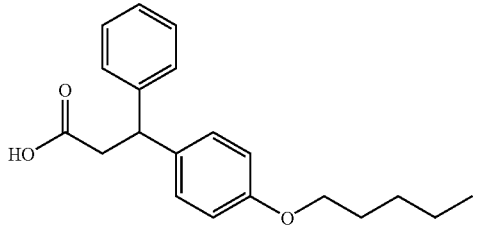

3-(4-Pentyloxy-phenyl)-3-phenyl-propionic acid

Scheme C

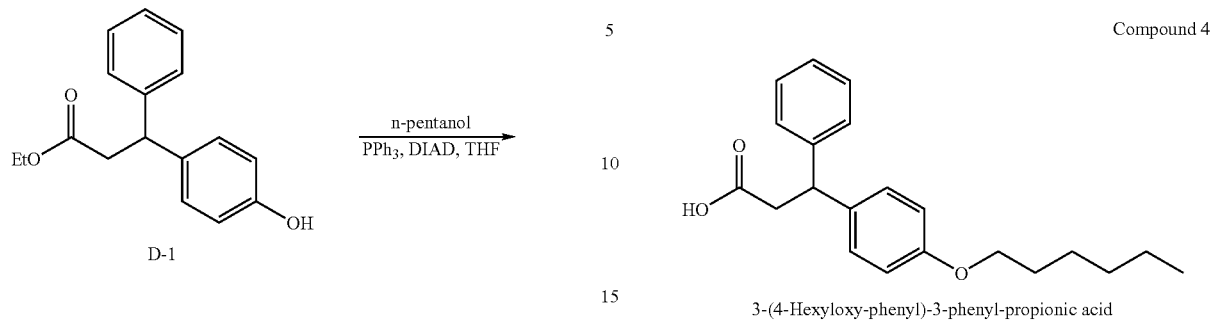

A solution of D-1 (135 mg, 0.50 mmol), n-pentanol (44 mg, 0.50 mmol) and PPh₃ (157 mg, 0.60 mmol) in THF (3 mL) was treated with DIAD (107 mg, 0.53 mmol). The reaction was stirred at room temperature for 7 h. Concentration and chromatograph on silica gel (20:1 hexane/EtOAc) gave 118 mg (69%) of F-3 as colorless oil. $^1$H NMR (300 MHz, CDCl₃) δ7.30-7.10 (m, 7H), 6.80 (d, J=8.0 Hz, 2H), 4.49 (t, J=7.5 Hz, 1H), 4.02 (q, J=6.0 Hz, 2H), 3.90 (t, J=6.0 Hz, 2H), 3.01 (d, J=7.5 Hz, 2H), 1.75 (tt, J=6.0, 6.0 Hz, 2H), 1.45-1.27 (m, 4H), 1.10 (t, J=6.0 Hz, 3H), 0.93 (t, J=6.0 Hz, 3H); MS (ES) m/z: 341 (M+H⁺).

A solution of F-3 (99 mg, 0.29 mmol) in THF/MeOH/H₂O (4:1:1 v/v/v, 15 mL) was treated with LiOH (1 M in H₂O, 2.5 mL, 2.5 mmol). The mixture was stirred at room temperature overnight. Saturated NH₄Cl aqueous solution was added and it was extracted with EtOAc thrice. The combined extracts were washed with brine and dried over Na₂SO₄. Concentration and chromatograph on silica gel (20:1 CH₂Cl₂/MeOH) gave 74 mg (81%) of the acid 3 as white solid. $^1$H NMR (300 MHz, CDCl₃) δ7.35-7.09 (m, 7H), 6.80 (d, J=8.0 Hz, 2H), 4.46 (t, J=7.5 Hz, 1H), 3.90 (t, J=6.0 Hz, 2H), 3.04 (d, J=7.5 Hz, 2H), 1.82-1.65 (m, 2H), 1.46-1.25 (m, 4H), 0.91 (t, J=6.0 Hz, 3H); MS (ES) m/z: 335 (M+Na⁺).

Example D

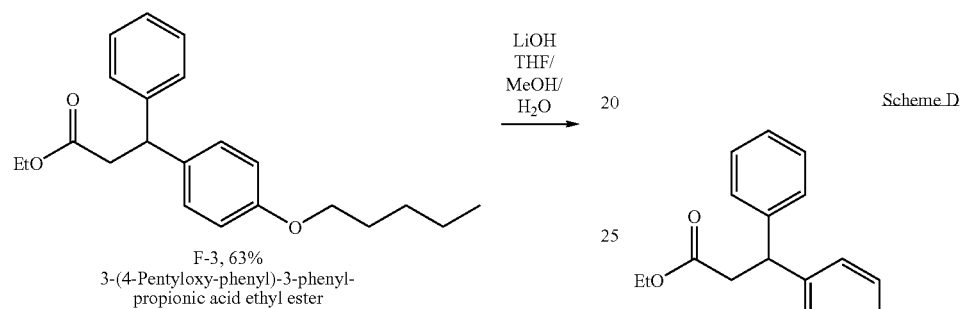

3-(4-Hexyloxy-phenyl)-3-phenyl-propionic acid

Scheme D

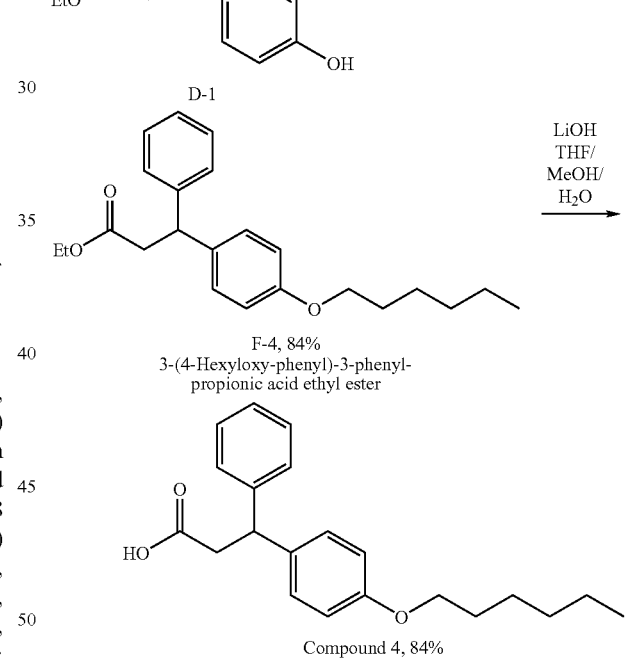

To a mixture of D-1 (189 mg, 0.70 mmol) in DMF (7 mL) with CsF (320 mg, 2.10 mmol) was added 1-iodohexane (178 mg, 0.84 mmol). The reaction was stirred at room temperature overnight. Water was added and the mixture was extracted with EtOAc thrice. The combined extracts were washed with H₂O, brine and dried over Na₂SO₄. Concentration and chromatograph on silica gel (10:1 hexane/EtOAc) gave 207 mg (84%) of F-4 as colorless oil. $^1$H NMR (300 MHz, CDCl₃) δ7.30-7.10 (m, 7H), 6.80 (d, J=9.0 Hz, 2H), 4.49 (t, J=7.5 Hz, 1H), 4.03 (q, J=6.0 Hz, 2H), 3.90 (t, J=6.0 Hz, 2H), 3.01 (d, J=7.5 Hz, 2H), 1.79-1.68 (tt, J=6.0, 6.0 Hz, 2H), 1.47-1.23 (m, 6H), 1.11 (t, J=6.0 Hz, 3H), 0.91 (t, J=6.0 Hz, 3H); MS (ES) m/z: 355 (M+H⁺).

A solution of F-4 (130 mg, 0.37 mmol) in THF/MeOH/H$_2$O (4:1:1 v/v/v, 12 mL) was treated with LiOH (1 M in H$_2$O, 2.0 mL, 2.0 mmol). The mixture was stirred at room temperature overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 101 mg (84%) of the acid 4 as white solid. $^1$H NMR (300 MHz, CDCl$_3$) δ7.30-7.10 (m, 7H), 6.80 (d, J=8.0 Hz, 2H), 4.47 (t, J=9.0 Hz, 1H), 3.90 (t, J=6.0 Hz, 2H), 3.05 (d, J=9.0 Hz, 2H), 1.74 (tt, J=6.0, 6.0 Hz, 2H), 1.48-1.26 (m, 6H), 0.89 (t, J=6.0 Hz, 3H); MS (ES) m/z: 349 (M+Na$^+$).

Example E

Compound 5

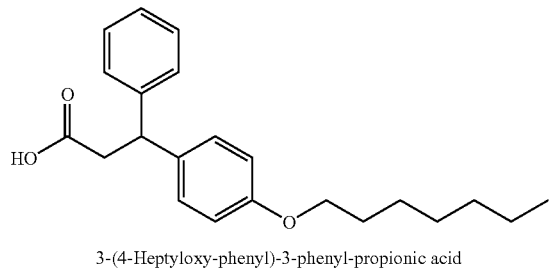

3-(4-Heptyloxy-phenyl)-3-phenyl-propionic acid

To a mixture of D-1 (189 mg, 0.70 mmol) in DMF (7 mL) with CsF (320 mg, 2.10 mmol) was added 1-iodoheptane (190 mg, 0.84 mmol). The reaction was stirred at room temperature overnight. Water was added and the mixture was extracted with EtOAc thrice. The combined extracts were washed with H$_2$O, brine and dried over Na$_2$SO$_4$. Concentration and chromatograph on silica gel (10:1 hexane/EtOAc) gave 228 mg (89%) of F-5 as colorless oil. $^1$H NMR (300 MHz, CDCl$_3$) δ7.30-7.10 (m, 7H), 6.80 (d, J=9.0 Hz, 2H), 4.49 (t, J=7.5 Hz, 1H), 4.03 (q, J=6.0 Hz, 2H), 3.90 (t, J=6.0 Hz, 2H), 3.01 (d, J=7.5 Hz, 2H), 1.79-1.65 (m, 2H), 1.47-1.21 (m, 8H), 1.11 (t, J=6.0 Hz, 3H), 0.88 (t, J=6.0 Hz, 3H); MS (ES) m/z: 369 (M+H$^+$).

A solution of F-5 (166 mg, 0.45 mmol) in THF/MeOH/H$_2$O (4:1:1 v/v/v, 18 mL) was treated with LiOH (1 M in H$_2$O, 3.0 mL, 3.0 mmol). The mixture was stirred at room temperature for overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 121 mg (79%) of the acid 5 as white solid. $^1$H NMR (300 MHz, CDCl$_3$) δ7.30-7.09 (m, 7H), 6.80 (d, J=6.0 Hz, 2H), 4.47 (t, J=7.5 Hz, 1H), 3.90 (t, J=6.0 Hz, 2H), 3.05 (d, J=7.5 Hz, 2H), 1.74 (tt, J=6.0, 6.0 Hz, 2H), 1.48-1.22 (m, 8H), 0.88 (t, J=6.0 Hz, 3H); MS (ES) m/z: 363 (M+Na$^+$).

Example F

Compound 6

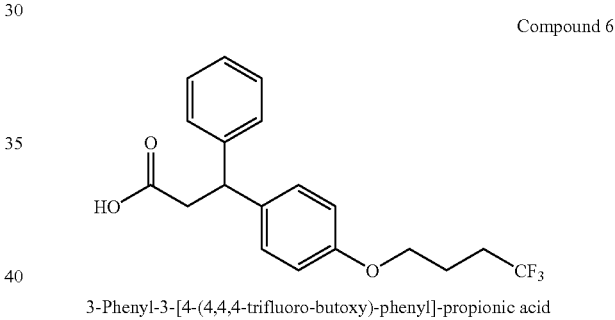

3-Phenyl-3-[4-(4,4,4-trifluoro-butoxy)-phenyl]-propionic acid

Scheme E

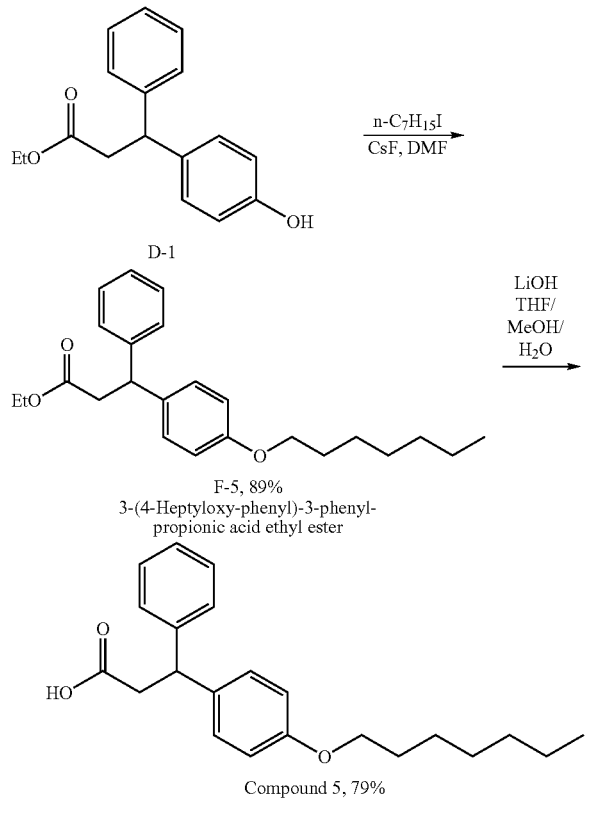

Scheme F

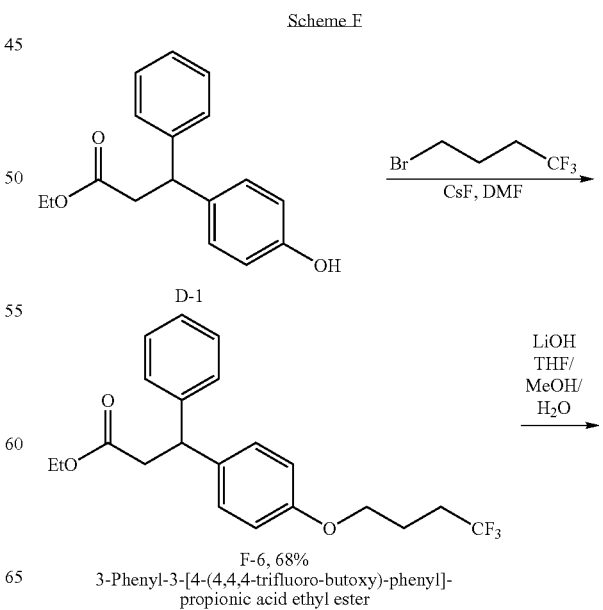

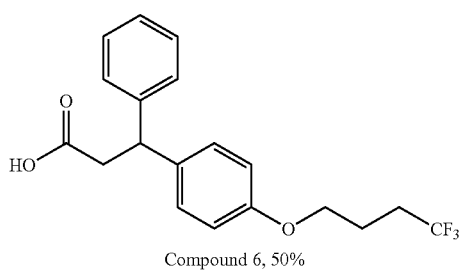

Compound 6, 50%

To a mixture of D-1 (162 mg, 0.60 mmol) in DMF (2 mL) with CsF (274 mg, 1.80 mmol) was added 4-Bromo-1,1,1-trifluoro-butane (172 mg, 0.9 mmol). The reaction was stirred at 80° C. overnight. Water was added and the mixture was extracted with EtOAc thrice. The combined extracts were washed with H$_2$O, brine and dried over Na$_2$SO$_4$. Concentration and chromatograph on silica gel (10:1 hexane/EtOAc) gave 155 mg (68%) of F-6 as colorless oil. $^1$H NMR (300 MHz, CDCl$_3$) δ7.30-7.11 (m, 7H), 6.79 (d, J=9.0 Hz, 2H), 4.49 (t, J=8.0 Hz, 1H), 4.03 (q, J=7.2 Hz, 2H), 3.97 (t, J=6.0 Hz, 2H), 3.01 (d, J=8.0 Hz, 2H), 2.38-2.20 (m, 2H), 2.06-1.95 (m, 2H), 1.11 (t, J=7.2 Hz, 3H); MS (ES) m/z: 403 (M+Na$^+$).

A solution of F-6 (97 mg, 0.25 mmol) in THF/MeOH/H$_2$O (4:1:1 v/v/v, 6 mL) was treated with LiOH (1 M in H$_2$O, 1.0 mL, 1.0 mmol). The mixture was stirred at room temperature overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 45 mg (50%) of the acid 6 as white solid. $^1$H NMR (300 MHz, CDCl$_3$) δ7.30-7.10 (m, 7H), 6.80 (d, J=8.6 Hz, 2H), 4.47 (t, J=7.8 Hz, 1H), 3.96 (t, J=6.0 Hz, 2H), 3.05 (d, J=7.8 Hz, 2H), 2.36-2.20 (m, 2H), 2.08-1.96 (m, 2H); MS (ES) m/z: 375 (M+Na$^+$).

Examples G & H

Compound 7

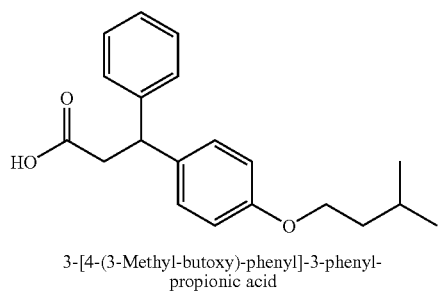

3-[4-(3-Methyl-butoxy)-phenyl]-3-phenyl-propionic acid

Compound 8

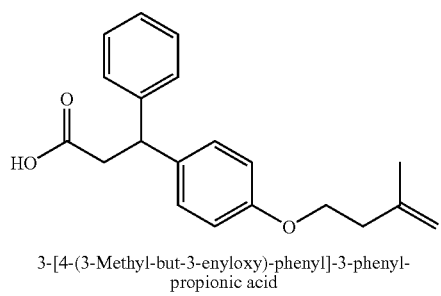

3-[4-(3-Methyl-but-3-enyloxy)-phenyl]-3-phenyl-propionic acid

Scheme G & H

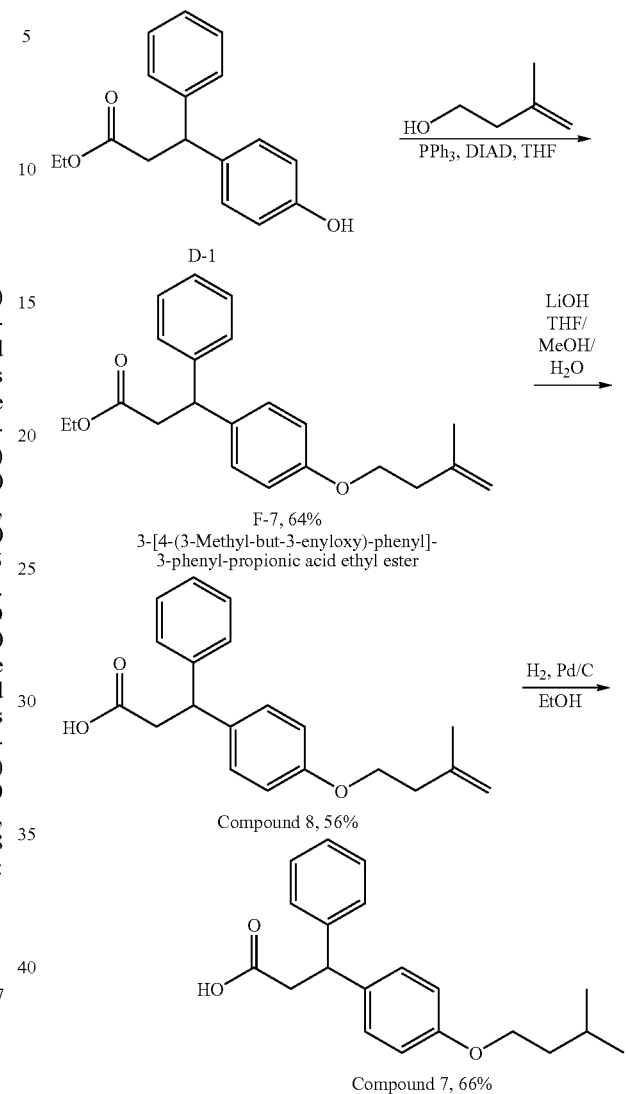

A solution of D-1 (100.0 mg, 0.37 mmol), 3-methyl-but-3-en-1-ol (32 mg, 0.37 mmol) and PPh$_3$ (117 mg, 0.44 mmol) in THF (2 mL) was treated with DIAD (79 mg, 0.39 mmol). The reaction was stirred at room temperature for 14 h. Concentration and chromatograph on silica gel (20:1 hexane/EtOAc) gave 80 mg (64%) of F-7 as colorless oil. $^1$H NMR (300 MHz, CDCl$_3$) δ7.30-7.10 (m, 7H), 6.82 (d, J=9.0 Hz, 2H), 4.82 (s, 1H), 4.78 (s, 1H), 4.49 (t, J=9.0 Hz, 1H), 4.08-3.99 (m, 2H), 3.01 (d, J=9.0 Hz, 2H), 2.47 (t, J=6.0 Hz, 2H), 1.78 (s, 3H), 1.11 (t, J=6.0 Hz, 3H); MS (ES) m/z: 361 (M+Na$^+$).

A solution of F-7 (60 mg, 0.18 mmol) in THF/MeOH/H$_2$O (4:1:1 v/v/v, 9 mL) was treated with LiOH (1 M in H$_2$O, 1.5 mL, 1.5 mmol). The mixture was stirred at room temperature for overnight. Saturated NH$_4$Cl aqueous solution was added and it was extracted with EtOAc thrice. The combined extracts were washed with brine and dried over Na$_2$SO$_4$. Concentration and chromatography on silica gel (20:1 CH$_2$Cl$_2$/MeOH) gave 31 mg (56%) of the acid 8 as white solid. $^1$H NMR (400 MHz, CDCl$_3$) δ7.30-7.15 (m, 5H), 7.13 (d, J=8.0 Hz, 2H), 6.81 (d, J=8.0 Hz, 2H), 4.82 (s, 1H), 4.78

(s, 1H), 4.47 (t, J=8.0 Hz, 1H), 4.03 (t, J=8.0 Hz, 2H), 3.05 (d, J=8.0 Hz, 2H), 2.47 (t, J=8.0 Hz, 2H), 1.79 (s, 3H); MS (ES) m/z: 333 (M+Na⁺).

A mixture of compound 8 (15 mg, 0.05 mmol) in EtOH (5 mL) with Pd/C (10% w/w, 20 mg) was shaken under H₂ (55 psi) for 5 h in Parr shaker. Filtration though Celite and concentration gave the crude. Chromatograph on silica gel (20:1 CH₂Cl₂/MeOH) gave 10 mg (66%) of the acid 7 as white solid. ¹H NMR (300 MHz, CDCl₃) δ7.30-7.15 (m, 5H), 7.12 (d, J=9.0 Hz, 2H), 6.80 (d, J=9.0 Hz, 2H), 4.46 (t, J=7.5 Hz, 1H), 3.93 (t, J=6.0 Hz, 2H), 3.04 (d, J=7.5 Hz, 2H), 1.87-1.72 (m, 1H), 1.64 (dt, J=6.0, 6.0 Hz, 2H), 0.94 (d, J=6.0 Hz, 6H); MS (ES) m/z: 335 (M+Na⁺).

Example I

Compound 9

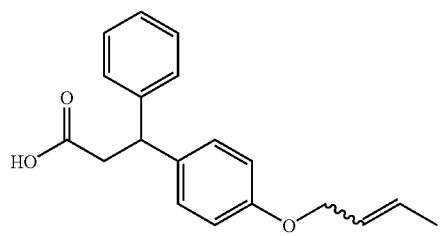

3-(4-But-2-enyloxy-phenyl)-3-phenyl-propionic acid

Scheme I

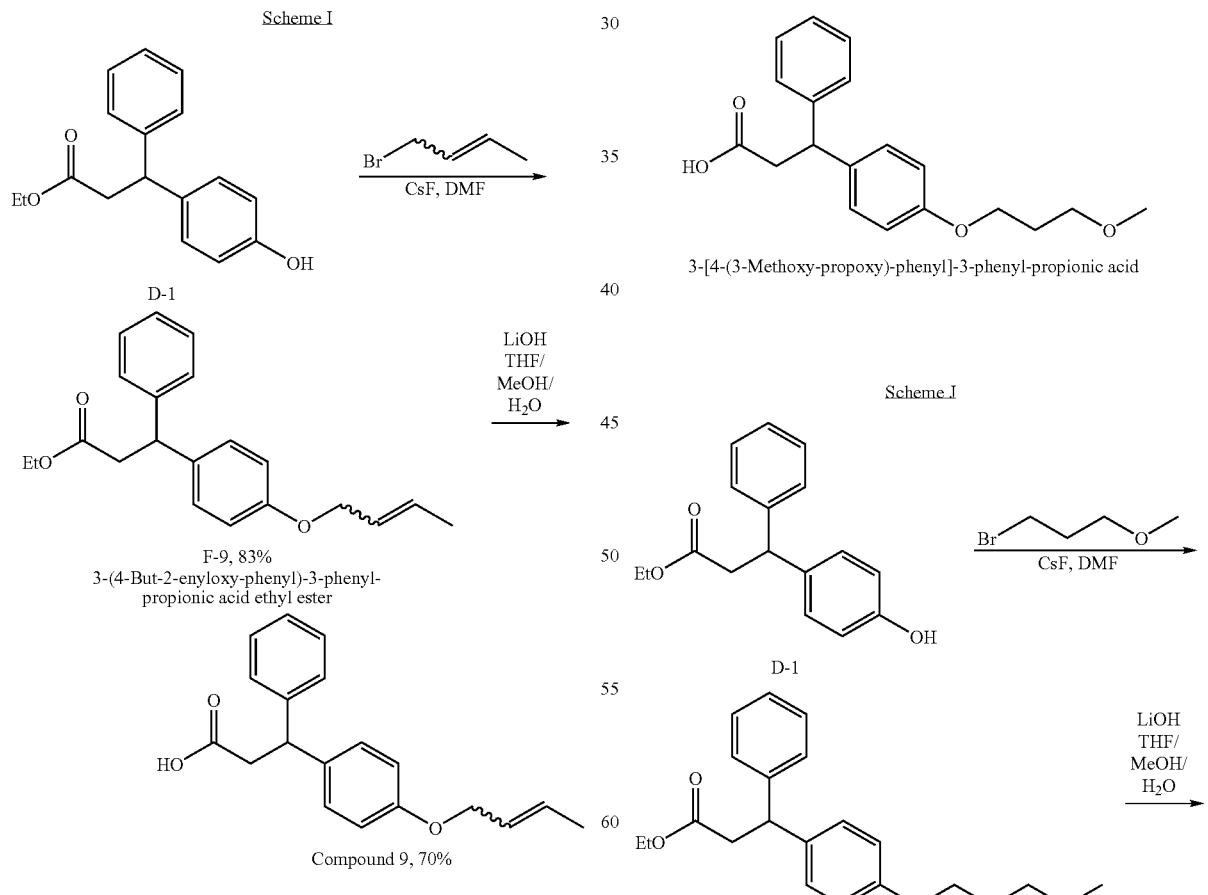

Compound D-1 (100 mg, 0.37 mmol) in DMF (3.5 mL) was treated with CsF (169 mg, 1.11 mmol) and then 1-Bromo-but-2-ene (71 mg, 0.44 mmol). The reaction mixture was stirred at room temperature for overnight. Water was added and the mixture was extracted with Et₂O thrice. The combined extracts were washed with H₂O, brine and dried over Na₂SO₄. Concentration and chromatograph on silica gel (20:1 hexane/EtOAc) gave 100 mg (83%) of F-9 as colorless oil. ¹H NMR (300 MHz, CDCl₃) δ7.30-7.10 (m, 7H), 6.82 (d, J=9.0 Hz, 2H), 5.89-5.64 (m, 2H), 4.56-4.38 (m, 3H), 4.03 (q, J=6.0 Hz, 2H), 3.01 (d, J=9.0 Hz, 2H), 1.74 (d, J=6.0 Hz, 3H), 1.11 (t, J=6.0 Hz, 3H); MS (ES) m/z: 347 (M+Na⁺).

A solution of F-9 (95 mg, 0.29 mmol) in THF/MeOH/H₂O (4:1:1 v/v/v, 9 mL) was treated with LiOH (1 M in H₂O, 1.5 mL, 1.5 mmol). The mixture was stirred at room temperature for overnight. Saturated NH₄Cl aqueous solution was added and it was extracted with EtOAc thrice. The combined extracts were washed with brine and dried over Na₂SO₄. Concentration and chromatograph on silica gel (20:1 CH₂Cl₂/MeOH) gave 61 mg (70%) of the acid 9 as white solid. ¹H NMR (300 MHz, CDCl₃) δ7.30-7.10 (m, 7H), 6.82 (d, J=9.0 Hz, 2H), 5.89-5.64 (m, 2H), 4.56-4.38 (m, 3H), 3.05 (d, J=9.0 Hz, 2H), 1.74 (d, J=6.0 Hz, 3H); MS (ES) m/z: 319 (M+Na⁺).

Example J

-continued

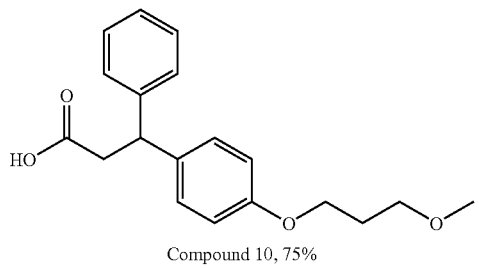

Compound 10, 75%

Compound D-1 (94 mg, 0.35 mmol) in DMF (1.0 mL) was treated with CsF (160 mg, 1.05 mmol) and then 1-bromo-3-methoxy-propane (54 mg, 0.35 mmol). The reaction mixture was stirred at room temperature overnight. Water was added and the mixture was extracted with Et$_2$O thrice. The combined extracts were washed with H$_2$O, brine and dried over Na$_2$SO$_4$. Concentration and chromatograph on silica gel (4:1 hexane/EtOAc) gave 96 mg (80%) of F-10 as colorless oil. $^1$H NMR (300 MHz, CDCl$_3$) δ7.30-7.10 (m, 7H), 6.81 (d, J=9.0 Hz, 2H), 4.49 (t, J=9.0 Hz, 1H), 4.08-3.95 (m, 4H), 3.53 (t, J=6.0 Hz, 2H), 3.33 (s, 3H), 3.01 (d, J=9.0 Hz, 2H), 2.08-1.95 (m, 2H), 1.11 (t, J=6.0 Hz, 3H); MS (ES) m/z: 343 (M+H$^+$).

A solution of F-10 (96 mg, 0.28 mmol) in THF/MeOH/H$_2$O (4:1:1 v/v/v, 9 mL) was treated with LiOH (1 M in H$_2$O, 1.5 mL, 1.5 mmol). The mixture was stirred at room temperature overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 67 mg (75%) of the acid 10 as white solid. $^1$H NMR (300 MHz, CDCl$_3$) δ7.30-7.10 (m, 7H), 6.81 (d, J=9.0 Hz, 2H), 4.46 (t, J=9.0 Hz, 1H), 4.00 (t, J=6.0 Hz, 2H), 3.53 (t, J=6.0 Hz, 2H), 3.33 (s, 3H), 3.04 (d, J=9.0 Hz, 2H), 2.01 (tt, J=6.0, 6.0 Hz, 2H); MS (ES) m/z: 333 (M+Na$^+$).

Example K

Compound 11

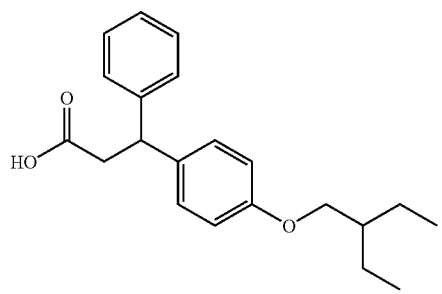

3-[4-(2-Ethyl-butoxy)-phenyl]-3-phenyl-propionic acid

Scheme K

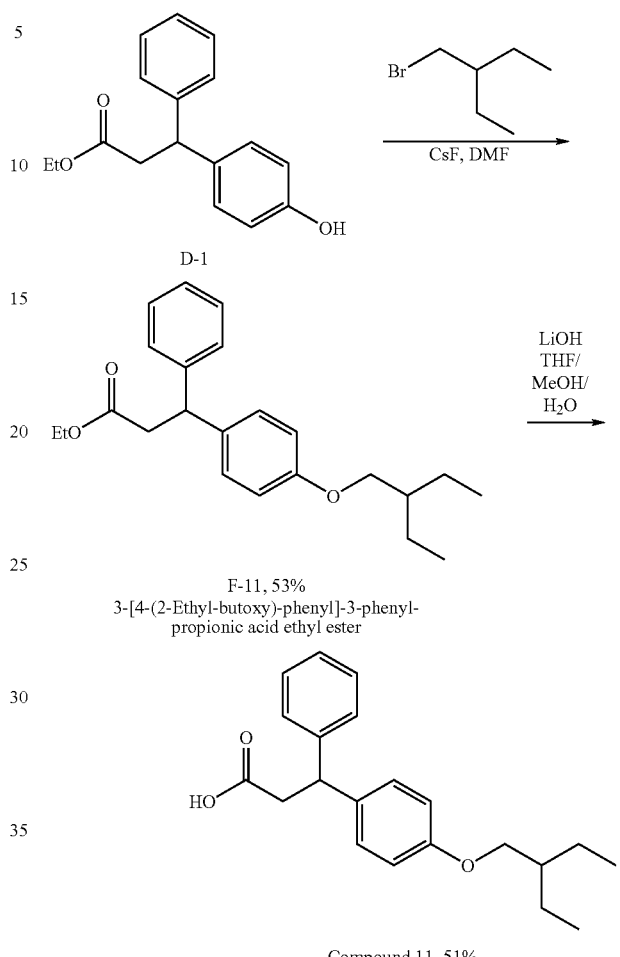

F-11, 53%
3-[4-(2-Ethyl-butoxy)-phenyl]-3-phenyl-propionic acid ethyl ester

Compound 11, 51%

Compound D-1 (108 mg, 0.40 mmol) in DMF (2 mL) was treated with CsF (182 mg, 1.20 mmol) and then 1-Bromo-2-ethylbutane (99 mg, 0.60 mmol). The reaction was stirred at room temperature for 48 h. Water was added and the mixture was extracted with EtOAc thrice. The combined extracts were washed with H$_2$O, brine and dried over Na$_2$SO$_4$. Concentration and chromatograph on silica gel (10:1 hexane/EtOAc) gave 75 mg (53%) of F-11 as colorless oil. $^1$H NMR (300 MHz, CDCl$_3$) δ7.30-7.15 (m, 5H), 7.13 (d, J=6.6 Hz, 2H), 6.81 (d, J=6.6 Hz, 2H), 4.49 (t, J=8.0 Hz, 1H), 4.03 (q, J=7.2 Hz, 2H), 3.79 (d, J=5.7 Hz, 2H), 3.01 (d, J=8.0 Hz, 2H), 1.69-1.53 (m, 1H), 1.50-1.38 (m, 4H), 1.11 (t, J=7.2 Hz, 3H), 0.91 (t, J=7.4 Hz, 6H); MS (ES) m/z: 355 (M+H$^+$).

A solution of F-11 (66 mg, 0.19 mmol) in THF/MeOH/H$_2$O (4:1:1 v/v/v, 6 mL) was treated with LiOH (1.0 M in H$_2$O, 1.0 mL, 1.0 mmol). The mixture was stirred at room temperature for overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 31 mg (51%) of the acid 11 as white solid. $^1$H NMR (300 MHz, CDCl$_3$) δ7.30-7.15 (m, 5H), 7.12 (d, J=6.6 Hz, 2H), 6.81 (d, J=6.6 Hz, 2H), 4.46 (t, J=8.0

Hz, 1H), 3.79 (d, J=5.7 Hz, 2H), 3.04 (d, J=8.0 Hz, 2H), 1.69-1.53 (m, 1H), 1.50-1.38 (m, 4H), 0.91 (t, J=7.4 Hz, 6H); MS (ES) m/z: 349 (M+Na$^+$).

Example L

Compound 12

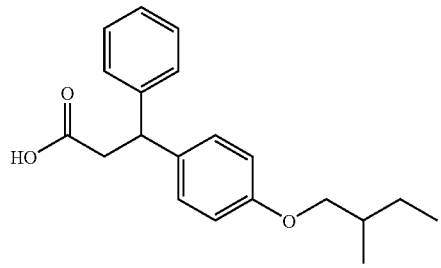

3-[4-(2-Methyl-butoxy)-phenyl]-3-phenyl-propionic acid

Scheme L

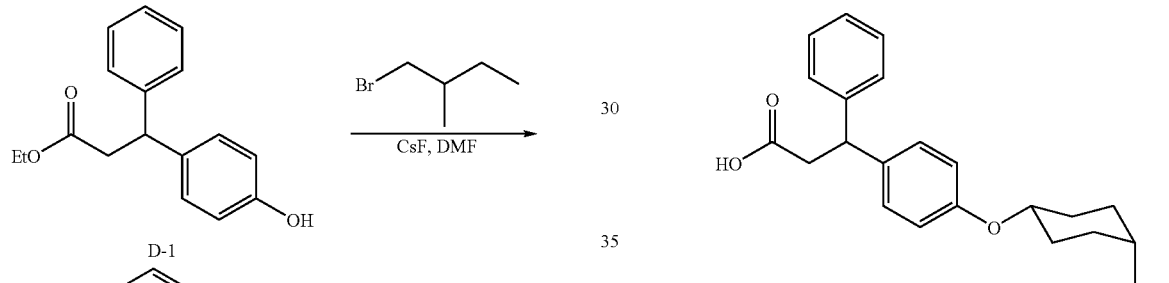

F-12, 65%
3-[4-(2-Methyl-butoxy)-phenyl]-3-phenyl-propionic acid ethyl ester

Compound 12, 56%

Compound D-1 (108 mg, 0.40 mmol) in DMF (2 mL) was treated with CsF (182 mg, 1.20 mmol) and then 1-Bromo-2-methylbutane (91 mg, 0.60 mmol). The reaction was stirred at room temperature for 48 h. Water was added and the mixture was extracted with EtOAc thrice. The combined extracts were washed with H$_2$O, brine and dried over Na$_2$SO$_4$. Concentration and chromatograph on silica gel (10:1 hexane/EtOAc) gave 88 mg (65%) of F-12 as colorless oil. $^1$H NMR (300 MHz, CDCl$_3$) δ7.30-7.10 (m, 7H), 6.80 (d, J=8.7 Hz, 2H), 4.49 (t, J=8.0 Hz, 1H), 4.03 (q, J=7.2 Hz, 2H), 3.77 (dd, J=6.0, 9.0 Hz, 1H), 3.68 (dd, J=6.5, 9.0 Hz, 1H), 3.01 (d, J=8.0 Hz, 2H), 1.89-1.63 (m, 1H), 1.35-1.16 (m, 2H), 1.11 (t, J=7.2 Hz, 3H), 0.99 (d, J=7.4 Hz, 3H), 0.93 (t, J=7.4 Hz, 3H); MS (ES) m/z: 341 (M+H$^+$).

A solution of F-12 (80 mg, 0.24 mmol) in THF/MeOH/H$_2$O (4:1:1 v/v/v, 9 mL) was treated with LiOH (1.0 M in H$_2$O, 1.5 mL, 1.5 mmol). The mixture was stirred at room temperature for overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 41 mg (56%) of the acid 12 as white solid.

Example M

Compound 13

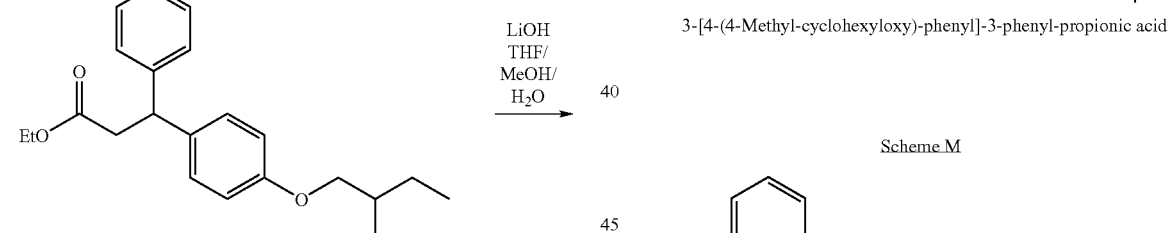

3-[4-(4-Methyl-cyclohexyloxy)-phenyl]-3-phenyl-propionic acid

Scheme M

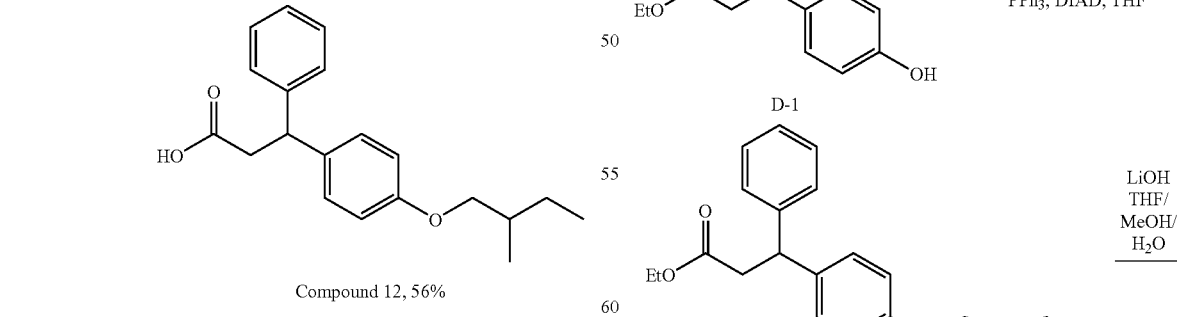

F-13, 36%
3-[4-(2-Methyl-cyclohexyloxy)-phenyl]-3-phenyl-propionic acid ethyl ester

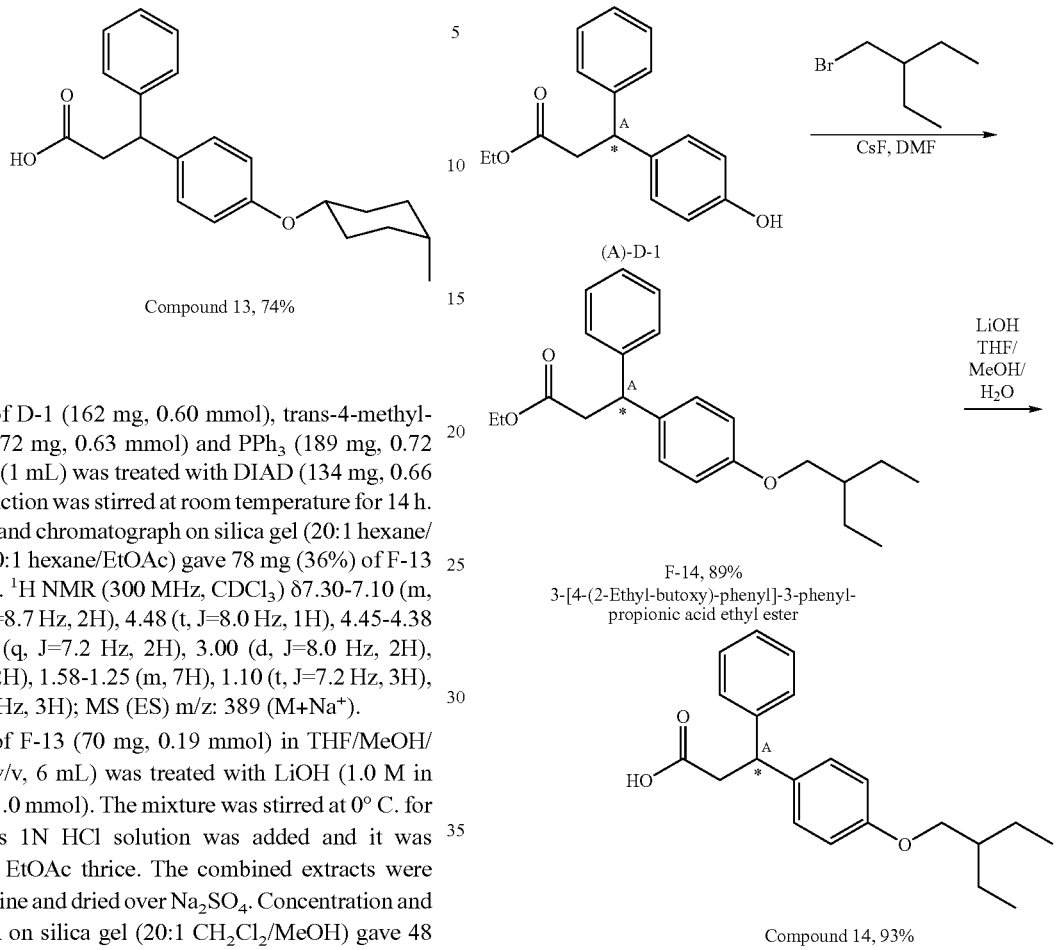

A solution of D-1 (162 mg, 0.60 mmol), trans-4-methyl-cyclohexanol (72 mg, 0.63 mmol) and PPh$_3$ (189 mg, 0.72 mmol) in THF (1 mL) was treated with DIAD (134 mg, 0.66 mmol). The reaction was stirred at room temperature for 14 h. Concentration and chromatograph on silica gel (20:1 hexane/EtOAc, then 10:1 hexane/EtOAc) gave 78 mg (36%) of F-13 as colorless oil. $^1$H NMR (300 MHz, CDCl$_3$) δ7.30-7.10 (m, 7H), 6.81 (d, J=8.7 Hz, 2H), 4.48 (t, J=8.0 Hz, 1H), 4.45-4.38 (m, 1H), 4.02 (q, J=7.2 Hz, 2H), 3.00 (d, J=8.0 Hz, 2H), 2.00-1.87 (m, 2H), 1.58-1.25 (m, 7H), 1.10 (t, J=7.2 Hz, 3H), 0.92 (d, J=5.8 Hz, 3H); MS (ES) m/z: 389 (M+Na$^+$).

A solution of F-13 (70 mg, 0.19 mmol) in THF/MeOH/H$_2$O (4:1:1 v/v/v, 6 mL) was treated with LiOH (1.0 M in H$_2$O, 1.0 mL, 1.0 mmol). The mixture was stirred at 0° C. for 48 h. Aqueous 1N HCl solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 48 mg (74%) of the acid 13 as white solid. $^1$H NMR (300 MHz, CDCl$_3$) δ7.30-7.10 (m, 7H), 6.81 (d, J=8.7 Hz, 2H), 4.48 (t, J=8.0 Hz, 1H), 4.43-4.38 (m, 1H), 3.04 (d, J=8.0 Hz, 2H), 2.00-1.87 (m, 2H), 1.58-1.35 (m, 7H), 0.92 (d, J=5.8 Hz, 3H); MS (ES) m/z: 361 (M+Na$^+$).

Example N

Compound 14

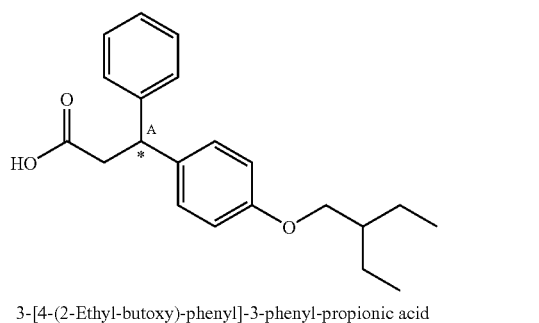

3-[4-(2-Ethyl-butoxy)-phenyl]-3-phenyl-propionic acid

Racemic mixture D-1 was resolved by chiral HPLC to give enantiomer A (shorter retention time) and enantiomer B (longer retention time). Compound (A)-D-1 (53 mg, 0.20 mmol) in DMF (0.5 mL) was treated with CsF (90 mg, 0.59 mmol) and then 1-Bromo-2-ethylbutane (49 mg, 0.29 mmol). The reaction was stirred at room temperature for overnight. Water was added and the mixture was extracted with EtOAc thrice. The combined extracts were washed with H$_2$O, brine and dried over Na$_2$SO$_4$. Concentration and chromatograph on silica gel (10:1 hexane/EtOAc) gave 62 mg (89%) of F-14 as colorless oil. $^1$H NMR (300 MHz, CDCl$_3$) δ7.30-7.10 (m, 7H), 6.81 (d, J=6.6 Hz, 2H), 4.49 (t, J=8.0 Hz, 1H), 4.03 (q, J=7.2 Hz, 2H), 3.79 (d, J=5.7 Hz, 2H), 3.01 (d, J=8.0 Hz, 2H), 1.69-1.53 (m, 1H), 1.50-1.38 (m, 4H), 1.11 (t, J=7.2 Hz, 3H), 0.91 (t, J=7.4 Hz, 6H); MS (ES) m/z: 377 (M+Na$^+$).

A solution of F-14 (48 mg, 0.14 mmol) in THF/MeOH/H$_2$O (4:1:1 v/v/v, 6 mL) was treated with LiOH (1.0 M in H$_2$O, 1.0 mL, 1.0 mmol). The mixture was stirred at room temperature for overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 41 mg (93%) of the acid 14 as white solid. $^1$H NMR (300 MHz, CDCl$_3$) δ7.30-7.15 (m, 5H), 7.12 (d, J=6.6 Hz, 2H), 6.81 (d, J=6.6 Hz, 2H), 4.46 (t, J=8.0

Hz, 1H), 3.79 (d, J=5.7 Hz, 2H), 3.04 (d, J=8.0 Hz, 2H), 1.69-1.53 (m, 1H), 1.50-1.38 (m, 4H), 0.91 (t, J=7.4 Hz, 6H); MS (ES) m/z: 349 (M+Na+).

Example O

Compound 15

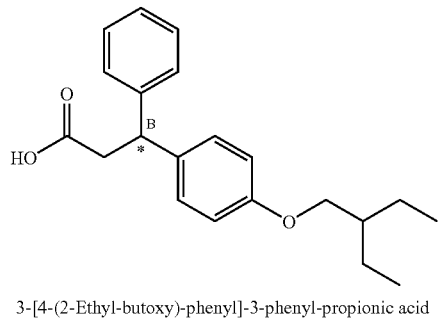

3-[4-(2-Ethyl-butoxy)-phenyl]-3-phenyl-propionic acid

Scheme O

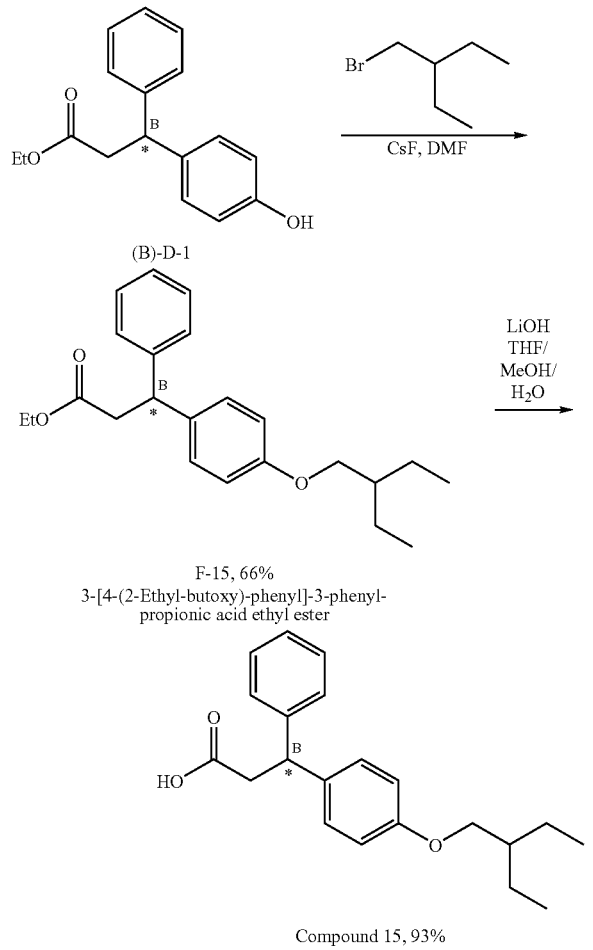

Racemic mixture D-1 was resolved by chiral HPLC to give enantiomer A (shorter retention time) and enantiomer B (longer retention time). Compound (B)-D-1 (38 mg, 0.14 mmol) in DMF (0.5 mL) was treated with CsF (64 mg, 0.42 mmol) and then 1-Bromo-2-ethylbutane (35 mg, 0.21 mmol). The reaction was stirred at room temperature for overnight. Water was added and the mixture was extracted with EtOAc thrice. The combined extracts were washed with H₂O, brine and dried over Na₂SO₄. Concentration and chromatograph on silica gel (10:1 hexane/EtOAc) gave 33 mg (66%) of F-15 as colorless oil. $^1$H NMR (300 MHz, CDCl$_3$) δ7.30-7.10 (m, 7H), 6.81 (d, J=6.6 Hz, 2H), 4.49 (t, J=8.0 Hz, 1H), 4.03 (q, J=7.2 Hz, 2H), 3.79 (d, J=5.7 Hz, 2H), 3.01 (d, J=8.0 Hz, 2H), 1.69-1.53 (m, 1H), 1.50-1.38 (m, 4H), 1.11 (t, J=7.2 Hz, 3H), 0.91 (t, J=7.4 Hz, 6H); MS (ES) m/z: 355 (M+H+).

A solution of F-15 (28 mg, 0.08 mmol) in THF/MeOH/H₂O (4:1:1 v/v/v, 3 mL) was treated with LiOH (1.0 M in H₂O, 0.5 mL, 0.5 mmol). The mixture was stirred at room temperature for overnight. Saturated NH₄Cl aqueous solution was added and it was extracted with EtOAc thrice. The combined extracts were washed with brine and dried over Na₂SO₄. Concentration and chromatograph on silica gel (20:1 CH₂Cl₂/MeOH) gave 24 mg (93%) of the acid 15 as white solid. $^1$H NMR (300 MHz, CDCl$_3$) δ7.30-7.15 (m, 5H), 7.12 (d, J=6.6 Hz, 2H), 6.81 (d, J=6.6 Hz, 2H), 4.46 (t, J=8.0 Hz, 1H), 3.79 (d, J=5.7 Hz, 2H), 3.04 (d, J=8.0 Hz, 2H), 1.69-1.53 (m, 1H), 1.50-1.38 (m, 4H), 0.91 (t, J=7.4 Hz, 6H); MS (ES) m/z: 349 (M+Na+).

Example P

Compound 16

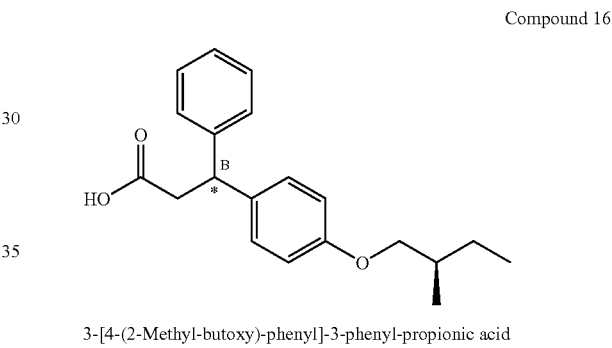

3-[4-(2-Methyl-butoxy)-phenyl]-3-phenyl-propionic acid

Scheme P

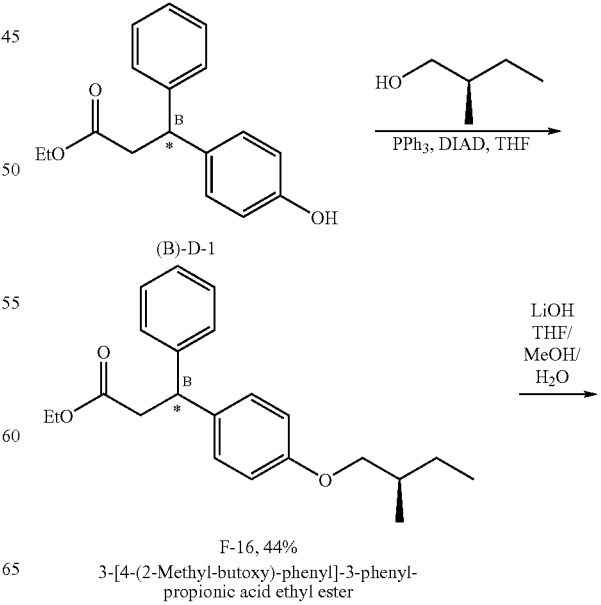

-continued

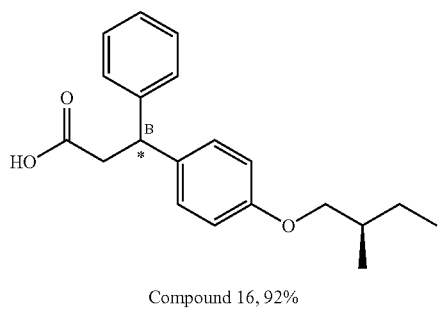

Compound 16, 92%

A solution of compound (B)-D-1 (81 mg, 0.30 mmol), (R)-2-methyl-butan-1-ol (26 mg, 0.30 mmol) and PPh$_3$ (94 mg, 0.36 mmol) in THF (1 mL) was treated with DIAD (67 mg, 0.33 mmol). The reaction was stirred at room temperature for 14 h. Concentration and chromatograph on silica gel (10:1 hexane/EtOAc) gave 45 mg (44%) of F-16 as colorless oil. $^1$H NMR (400 MHz, CDCl$_3$) δ7.30-7.10 (m, 7H), 6.81 (d, J=8.7 Hz, 2H), 4.49 (t, J=8.0 Hz, 1H), 4.03 (q, J=7.1 Hz, 2H), 3.76 (dd, J=6.0 Hz, J=9.0 Hz, 1H), 3.68 (dd, J=6.6, 9.0 Hz, 1H), 3.01 (d, J=8.0 Hz, 2H), 1.86-1.76 (m, 1H), 1.60-1.49 (m, 1H), 1.30-1.19 (m, 1H), 1.13 (t, J=7.1 Hz, 3H), 0.98 (d, J=6.7 Hz, 3H), 0.93 (t, J=7.2 Hz, 3H); MS (ES) m/z: 341 (M+H$^+$).

A solution of F-16 (45 mg, 0.13 mmol) in THF/MeOH/H$_2$O (4:1:1 v/v/v, 3.0 mL) was treated with LiOH (1.0 M in H$_2$O, 0.5 mL, 0.5 mmol). The mixture was stirred at room temperature for overnight. Aqueous 1N HCl solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 38 mg (92%) of the acid 16 as colorless oil film. $^1$H NMR (400 MHz, CDCl$_3$) δ7.30-7.10 (m, 7H), 6.81 (d, J=8.6 Hz, 2H), 4.48 (t, J=7.8 Hz, 1H), 3.77 (dd, J=6.0, 9.0 Hz, 1H), 3.68 (dd, J=6.6, 9.0 Hz, 1H), 3.06 (d, J=7.9 Hz, 2H), 1.86-1.76 (m, 1H), 1.60-1.49 (m, 1H), 1.30-1.19 (m, 1H), 0.98 (d, J=6.7 Hz, 3H), 0.92 (t, J=7.4 Hz, 3H); MS (ES) m/z: 335 (M+Na$^+$).

Example Q

Compound 17

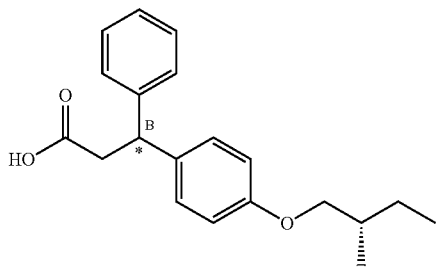

3-[4-(2-Methyl-butoxy)-phenyl]-3-phenyl-propionic acid

Scheme Q

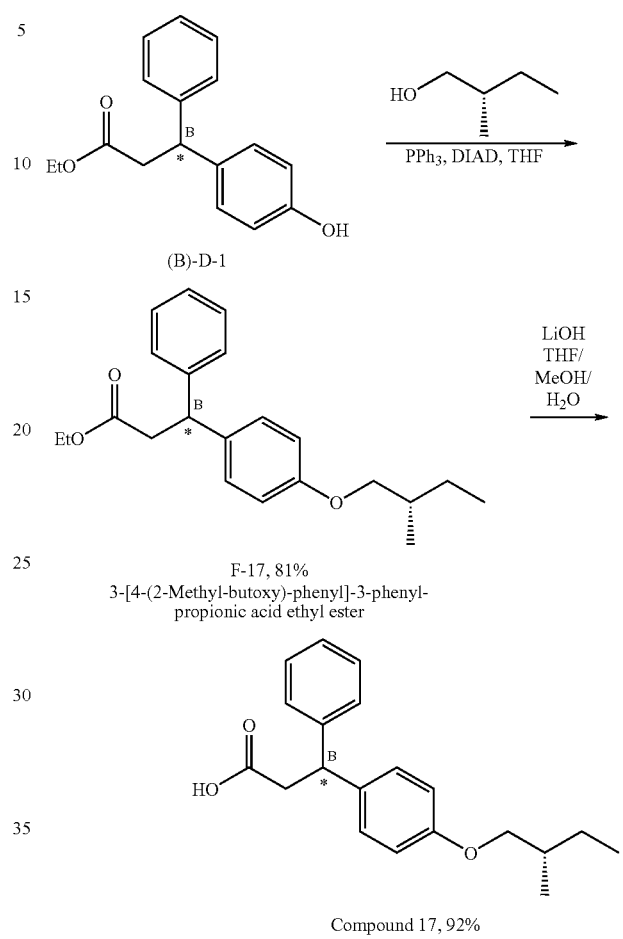

A solution of compound (B)-D-1 (216 mg, 0.80 mmol), (S)-2-methyl-butan-1-ol alcohol (74 mg, 0.84 mmol) and PPh$_3$ (252 mg, 0.96 mmol) in THF (1.5 mL) was treated with DIAD (178 mg, 0.88 mmol). The reaction was stirred at room temperature for 14 h. Concentration and chromatograph on silica gel (20:1 hexane/EtOAc) gave 221 mg (81%) of F-17 as colorless oil. $^1$H NMR (300 MHz, CDCl$_3$) δ7.30-7.10 (m, 7H), 6.81 (d, J=8.7 Hz, 2H), 4.49 (t, J=8.0 Hz, 1H), 4.03 (q, J=7.1 Hz, 2H), 3.77 (dd, J=6.0, 9.0 Hz, 1H), 3.68 (dd, J=6.6, 9.0 Hz, 1H), 3.01 (d, J=8.1 Hz, 2H), 1.86-1.76 (m, 1H), 1.60-1.49 (m, 1H), 1.30-1.19 (m, 1H), 1.11 (t, J=7.1 Hz, 3H), 0.99 (d, J=6.7 Hz, 3H), 0.93 (t, J=7.2 Hz, 3H); MS (ES) m/z: 341 (M+H$^+$); α[□]$_D$=5.5 (c=1).

A solution of F-17 (200 mg, 0.59 mmol) in THF/MeOH/H$_2$O (4:1:1 v/v/v, 6.0 mL) was treated with LiOH (1.0 M in H$_2$O, 1.0 mL, 1.0 mmol). The mixture was stirred at room temperature for overnight. Aqueous 1N HCl solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 168 mg (92%) of the acid 17 as white solid. $^1$H NMR (300 MHz, CDCl$_3$) δ7.30-7.10 (m, 7H), 6.81 (d, J=8.6 Hz, 2H), 4.47 (t, J=7.8 Hz, 1H), 3.77 (dd, J=6.0, 9.0 Hz, 1H), 3.68 (dd, J=6.6, 9.0 Hz, 1H), 3.05 (d, J=7.9 Hz, 2H), 1.88-1.76 (m, 1H), 1.60-1.46 (m, 1H), 1.31-1.18 (m, 1H), 0.98 (d, J=6.7 Hz, 3H), 0.92 (t, J=7.4 Hz, 3H); MS (ES) m/z: 335 (M+Na+).

Example R

Compound 18

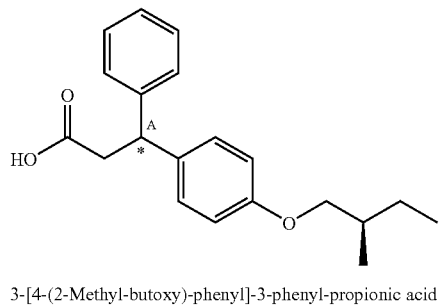

3-[4-(2-Methyl-butoxy)-phenyl]-3-phenyl-propionic acid

Scheme R

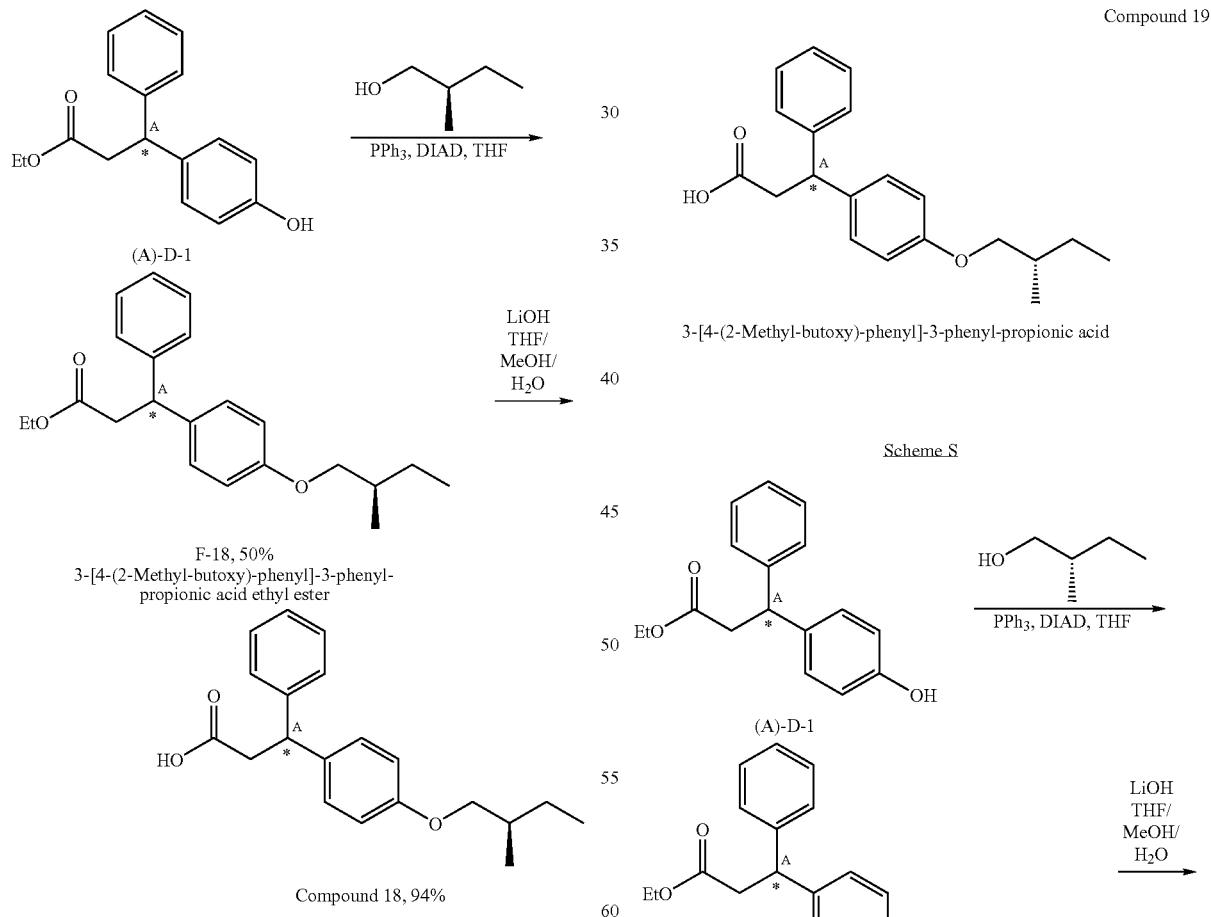

A solution of (A)-D-1 (81 mg, 0.30 mmol), (R)-2-methyl-butan-1-ol alcohol (26 mg, 0.30 mmol) and PPh₃ (94 mg, 0.36 mmol) in THF (1 mL) was treated with DIAD (67 mg, 0.33 mmol). The reaction was stirred at room temperature for 14 h. Concentration and chromatograph on silica gel (10:1 hexane/EtOAc) gave 51 mg (50%) of F-18 as colorless oil. $^1$H NMR (300 MHz, CDCl₃) δ7.30-7.10 (m, 7H), 6.81 (d, J=8.7 Hz, 2H), 4.49 (t, J=8.0 Hz, 1H), 4.03 (q, J=7.1 Hz, 2H), 3.77 (dd, J=6.0, 9.0 Hz, 1H), 3.68 (dd, J=6.6, 9.0 Hz, 1H), 3.01 (d, J=8.1 Hz, 2H), 1.86-1.76 (m, 1H), 1.60-1.48 (m, 1H), 1.30-1.15 (m, 1H), 1.11 (t, J=7.1 Hz, 3H), 0.99 (d, J=6.7 Hz, 3H), 0.93 (t, J=7.2 Hz, 3H); MS (ES) m/z: 341 (M+H+).

A solution of F-18 (51 mg, 0.15 mmol) in THF/MeOH/H₂O (4:1:1 v/v/v, 3 mL) was treated with LiOH (1.0 M in H₂O, 0.5 mL, 0.5 mmol). The mixture was stirred at room temperature for overnight. Aqueous 1N HCl solution was added and it was extracted with EtOAc thrice. The combined extracts were washed with brine and dried over Na₂SO₄. Concentration and chromatograph on silica gel (20:1 CH₂Cl₂/MeOH) gave 44 mg (94%) of the acid 18 as white solid. $^1$H NMR (300 MHz, CDCl₃) δ7.30-7.10 (m, 7H), 6.81 (d, J=8.6 Hz, 2H), 4.47 (t, J=7.8 Hz, 1H), 3.77 (dd, J=6.0, 9.0 Hz, 1H), 3.68 (dd, J=6.6, 9.0 Hz, 1H), 3.05 (d, J=7.9 Hz, 2H), 1.88-1.76 (m, 1H), 1.60-1.46 (m, 1H), 1.31-1.18 (m, 1H), 0.98 (d, J=6.7 Hz, 3H), 0.92 (t, J=7.4 Hz, 3H); MS (ES) m/z: 335 (M+Na+).

Example S

Compound 19

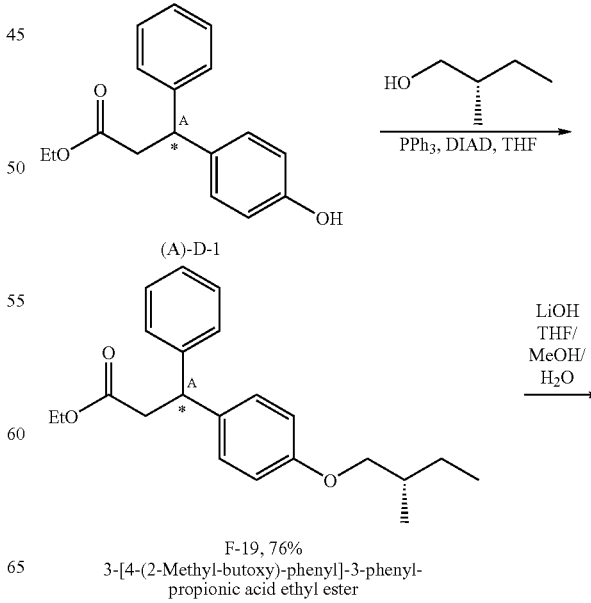

3-[4-(2-Methyl-butoxy)-phenyl]-3-phenyl-propionic acid

Scheme S

-continued

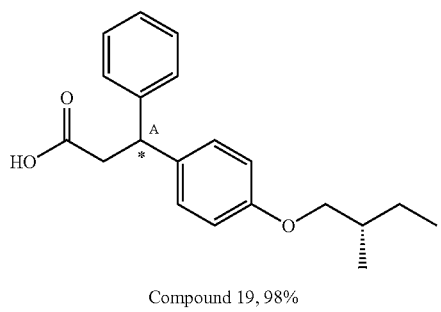

Compound 19, 98%

A solution of (A)-D-1 (108 mg, 0.40 mmol), (S)-2-methyl-butan-1-ol alcohol (37 mg, 0.42 mmol) and PPh$_3$ (126 mg, 0.48 mmol) in THF (1 mL) was treated with DIAD (89 mg, 0.44 mmol). The reaction was stirred at room temperature for 14 h. Concentration and chromatograph on silica gel (10:1 hexane/EtOAc) gave 103 mg (76%) of F-19 as colorless oil. $^1$H NMR (300 MHz, CDCl$_3$) δ7.30-7.10 (m, 7H), 6.81 (d, J=8.7 Hz, 2H), 4.49 (t, J=8.0 Hz, 1H), 4.03 (q, J=7.1 Hz, 2H), 3.77 (dd, J=6.0, 9.0 Hz, 1H), 3.68 (dd, J=6.6, 9.0 Hz, 1H), 3.01 (d, J=8.1 Hz, 2H), 1.86-1.76 (m, 1H), 1.60-1.49 (m, 1H), 1.30-1.19 (m, 1H), 1.11 (t, J=7.1 Hz, 3H), 0.99 (d, J=6.7 Hz, 3H), 0.93 (t, J=7.2 Hz, 3H); MS (ES) m/z: 341 (M+H$^+$).

A solution of F-19 (92 mg, 0.27 mmol) in THF/MeOH/H$_2$O (4:1:1 v/v/v, 6.0 mL) was treated with LiOH (1.0 M in H$_2$O, 1.0 mL, 1.0 mmol). The mixture was stirred at room temperature for overnight. Aqueous 1N HCl solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 83 mg (98%) of the acid 19 as colorless oil film. $^1$H NMR (300 MHz, CDCl$_3$) δ7.30-7.10 (m, 7H), 6.81 (d, J=8.6 Hz, 2H), 4.47 (t, J=7.8 Hz, 1H), 3.77 (dd, J=6.0, 9.0 Hz, 1H), 3.68 (dd, J=6.6, 9.0 Hz, 1H), 3.05 (d, J=7.9 Hz, 2H), 1.88-1.76 (m, 1H), 1.60-1.46 (m, 1H), 1.31-1.18 (m, 1H), 0.98 (d, J=6.7 Hz, 3H), 0.92 (t, J=7.4 Hz, 3H); MS (ES) m/z: 335 (M+Na$^+$).

Example T

Compound 20

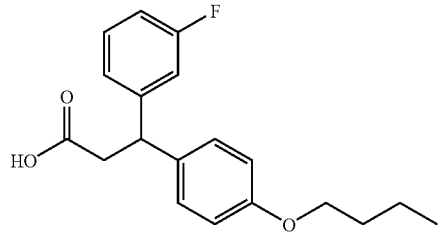

3-(4-Butoxy-phenyl)-3-(3-fluoro-phenyl)-propionic acid

Scheme T

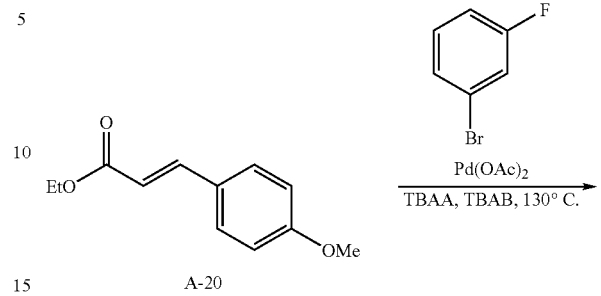

A-20

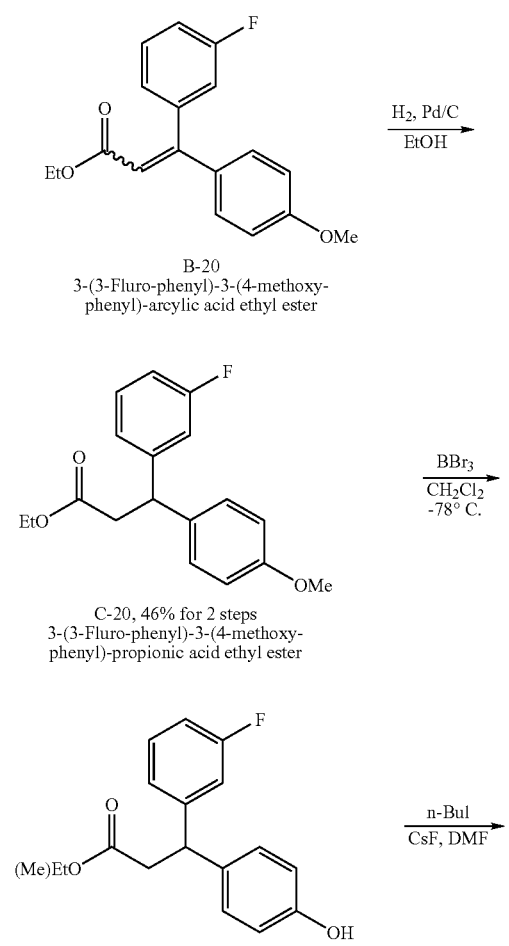

B-20
3-(3-Fluro-phenyl)-3-(4-methoxy-phenyl)-arcylic acid ethyl ester

C-20, 46% for 2 steps
3-(3-Fluro-phenyl)-3-(4-methoxy-phenyl)-propionic acid ethyl ester

D-20, 96%

F-20, 78%

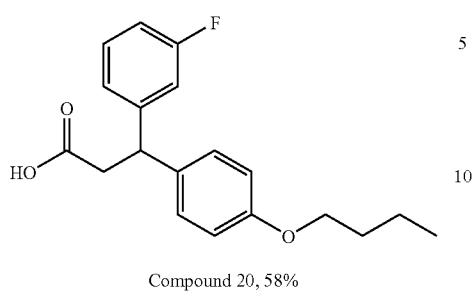

Compound 20, 58%

Tetrabutylammonium bromide (1.64 g) was melted at 130° C. Compound A-20 (618 mg, 3.0 mmol), 1-Bromo-3-fluorobenzene (788 mg, 4.5 mmol), Pd(OAc)$_2$ (20 mg, 0.09 mmol) and then tetrabutylammonium acetate (2.26 g, 7.5 mmol) were added. The mixture was stirred at 130° C. for 30 h. Water was added to the cooled mixture and it was extracted with hexane thrice. The combined extracts were washed with water (×2), brine and dried over Na$_2$SO$_4$. Concentration and chromatograph (10:1 hexane/EtOAc) gave 839.2 mg of a mixture containing B-20. The mixture (826 mg) was dissolved in EtOH (50 mL) with Pd/C (10% w/w, 450 mg) and then was shaken under H$_2$ in Parr shaker for overnight. Filtration through Celite and concentration gave the crude. Chromatograph on silica gel (20:1 hexane/EtOAc) gave 421 mg (46% for 2 steps) of C-20 as colorless oil. $^1$H NMR (400 MHz, CDCl$_3$) δ7.26-7.20 (m, 1H), 7.14 (d, J=8.0 Hz, 2H), 7.01 (d, J=8.0 Hz, 1H), 6.92-6.84 (m, 2H), 6.83 (d, J=8.0 Hz, 2H), 4.49 (t, J=7.8 Hz, 1H), 4.04 (q, J=8.0 Hz, 2H), 3.77 (s, 3H), 2.99 (d, J=7.8 Hz, 2H), 1.12 (t, J=8.0 Hz, 3H); MS (ES) m/z: 325 (M+Na$^+$).

Compound C-20 (384 mg, 1.30 mmol) in CH$_2$Cl$_2$ (15 mL) at −78° C. was treated with BBr$_3$ (1.0 M in CH$_2$Cl$_2$, 1.90 ml, 1.90 mmol). The mixture was stirred at room temperature for 5 h. Anhydrous MeOH was added and the then solution was concentrated. This process was repeated thrice. The residue was purified by chromatograph on silica gel (4:1 hexane/EtOAc) to give 346 mg (96%) of a 1:1 mixture of the methyl ester and the ethyl ester of D-20.

Compound D-20 (49 mg) in DMF (1.5 mL) with CsF (79 mg, 0.52 mmol) was treated with n-butyl iodide (48 mg, 0.26 mmol). The mixture was stirred for overnight. Chromatograph of the mixture on silica gel (10:1 hexane/EtOAc) gave 46 mg (78%) of F-20.

A solution of F-20 (46 mg) in THF/MeOH/H$_2$O (4:1:1 v/v/v, 6.0 mL) was treated with LiOH (1.0 mL, 1.0 mmol, 1 N). The mixture was stirred at room temperature for overnight. Aqueous 1N HCl solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 25 mg (58%) of the acid 20 as white solid. $^1$H NMR (400 MHz, CDCl$_3$) δ7.26-7.20 (m, 1H), 7.11 (d, J=8.0 Hz, 2H), 7.00 (d, J=8.0 Hz, 1H), 6.90-6.83 (m, 2H), 6.82 (d, J=8.0 Hz, 2H), 4.45 (t, J=7.8 Hz, 1H), 3.92 (t, J=8.0 Hz, 2H), 3.02 (d, J=7.8 Hz, 2H), 1.78-1.69 (m, 2H), 1.52-1.40 (m, 2H), 0.96 (t, J=8.0 Hz, 3H); MS (ES) m/z: 339 (M+Na$^+$).

Example U

Compound 21

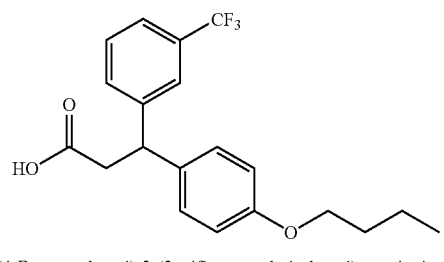

3-(4-Butoxy-phenyl)-3-(3-trifluoromethyl-phenyl)-propionic acid

Scheme U

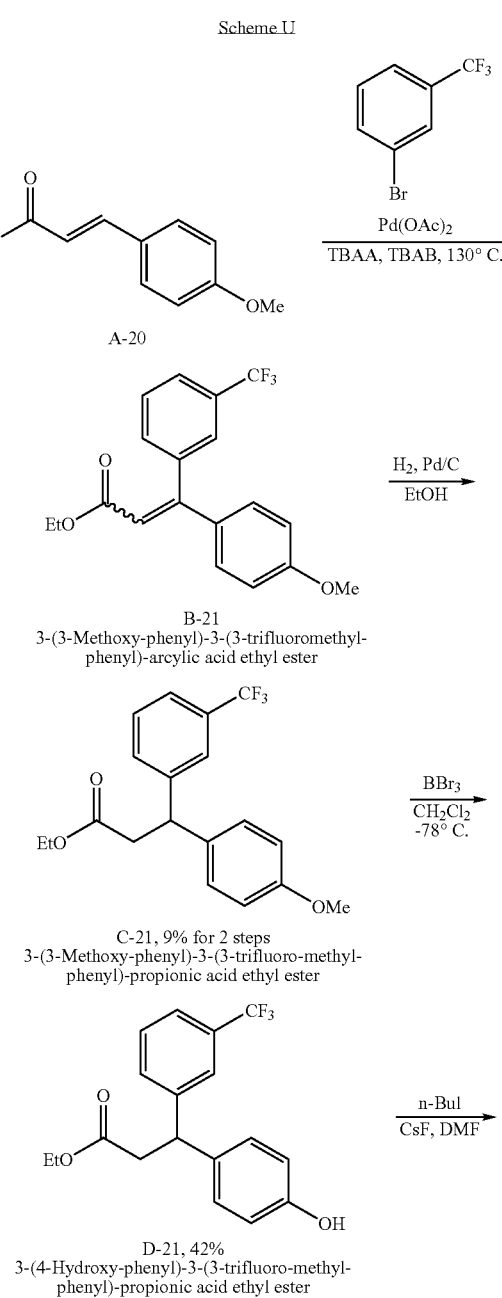

-continued

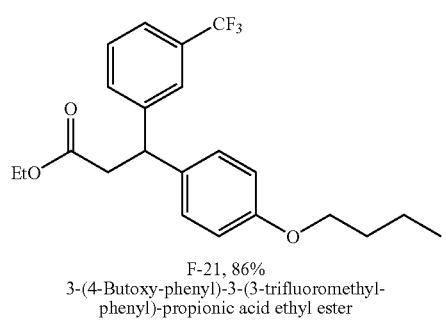

F-21, 86%
3-(4-Butoxy-phenyl)-3-(3-trifluoromethyl-phenyl)-propionic acid ethyl ester LiOH
THF/
MeOH/
H$_2$O

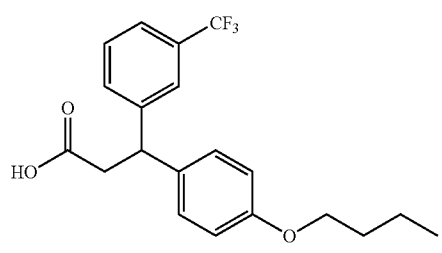

Compound 21, 65%

Tetrabutylammonium bromide (3.00 g) was melted at 130° C. Compound A-20 (1.17 g, 5.70 mmol), 1-Bromo-3-trifluoromethyl-benzene (1.28 g, 5.70 mmol), Pd(OAc)$_2$ (19 mg, 0.08 mmol), and then tetrabutylammonium acetate (4.28 g, 14.2 mmol) were added. The mixture was stirred at 130° C. for overnight. Water was added to the cooled mixture and it was extracted with Et$_2$O. The organic phase was concentrated to give the crude. Chromatograph on silica gel (20:1 hexane/EtOAc) gave 335 mg of a mixture containing B-21. The mixture (335 mg) was dissolved in EtOH (30 mL) with Pd/C (10% w/w, 300 mg) and was shaken under H$_2$ (55 psi) for 6 h. Filtration through Celite and concentration gave the crude. Chromatograph on silica gel (20:1 hexane/EtOAc) gave 187 mg (9% for 2 steps) of C-21 as colorless oil. $^1$H NMR (400 MHz, CDCl$_3$) δ7.59-7.36 (m, 3H), 7.12 (d, J=8.0 Hz, 2H), 6.83 (d, J=8.0 Hz, 2H), 4.54 (t, J=7.8 Hz, 1H), 4.04 (q, J=8.0 Hz, 2H), 3.77 (s, 3H), 3.02 (d, J=7.8 Hz, 2H), 1.11 (t, J=8.0 Hz, 3H); MS (ES) m/z: 353 (M+H$^+$).

Compound C-21 (188 mg, 0.53 mmol) in CH$_2$Cl$_2$ (6 mL) at −78° C. was treated with BBr$_3$ (1.0 M in CH$_2$Cl$_2$, 0.80 ml, 0.80 mmol,). The mixture was stirred at 0° C. for 2 h and then at room temperature for overnight. Saturated NaHCO$_3$ aqueous solution was added to the cooled (0° C.) reaction mixture. The mixture was extracted with EtOAc thrice. The combined extracts were washed with H$_2$O, brine and dried (Na$_2$SO$_4$). Concentration and chromatograph on silica gel (4:1 hexane/EtOAc) give 75 mg (42%) of D-21 as colorless oil. $^1$H NMR (400 MHz, CDCl$_3$) δ7.49-7.36 (m, 3H), 7.07 (d, J=8.0 Hz, 2H), 6.74 (d, J=8.0 Hz, 2H), 5.16 (s, 1H, OH), 4.54 (t, J=7.8 Hz, 1H), 4.03 (q, J=8.0 Hz, 2H), 3.02 (d, J=7.8 Hz, 2H), 1.12 (t, J=8.0 Hz, 3H); MS (ES) m/z: 339 (M+H$^+$).

Compound D-21 (22 mg, 0.07 mmol) in DMF (0.6 mL) with CsF (30 mg, 0.20 mmol) was treated with n-butyl iodide (15 mg, 0.08 mmol). The mixture was stirred at room temperature for overnight. Chromatograph of the mixture on silica gel (20:1 hexane/EtOAc) gave 22 mg (86%) of F-21 as colorless oil. $^1$H NMR (300 MHz, CDCl$_3$) δ7.49-7.36 (m, 3H), 7.12 (d, J=8.0 Hz, 2H), 6.83 (d, J=8.0 Hz, 2H), 4.55 (t, J=7.8 Hz, 1H), 4.04 (q, J=8.0 Hz, 2H), 3.92 (t, J=6.0 Hz, 2H), 3.02 (d, J=7.8 Hz, 2H), 1.75 (tt, J=6.0, 6.0 Hz, 2H), 1.47 (tq, J=6.0, 6.0 Hz, 2H), 1.11 (t, J=8.0 Hz, 3H), 0.96 (t, J=6.0 Hz, 3H); MS (ES) m/z: 395 (M+H$^+$).

Compound F-21 (20 mg, 0.05 mmol) in THF/MeOH/H$_2$O (4:1:1 v/v/v, 3.6 mL) was treated with LiOH (1.0 M in H$_2$O, 0.6 mL, 0.6 mmol). The mixture was stirred at room temperature for overnight. Aqueous 1N HCl solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 12 mg (65%) of the acid 21 as colorless oil. $^1$H NMR (300 MHz, CDCl$_3$) δ7.46-7.35 (m, 3H), 7.11 (d, J=8.0 Hz, 2H), 6.82 (d, J=8.0 Hz, 2H), 4.52 (t, J=7.5 Hz, 1H), 3.92 (t, J=6.0 Hz, 2H), 3.06 (d, J=7.5 Hz, 2H), 1.74 (tt, J=6.0, 6.0 Hz, 2H), 1.47 (tq, J=6.0, 6.0 Hz, 2H), 0.96 (t, J=6.0 Hz, 3H); MS (ES) m/z: 367 (M+H$^+$).

Example V

Compound 22

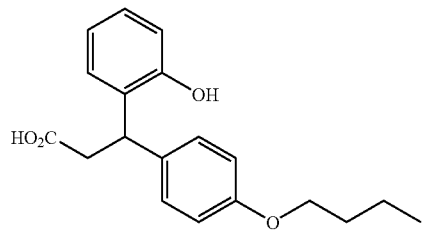

3-(4-Butoxy-phenyl)-3-(2-hydroxy-phenyl)-propionic acid

Scheme V

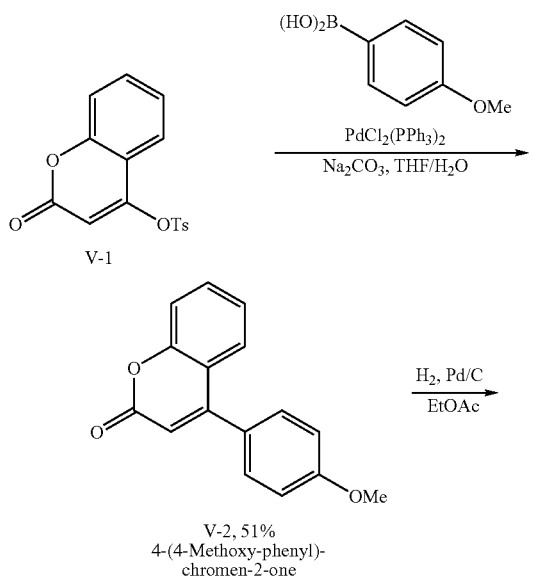

V-2, 51%
4-(4-Methoxy-phenyl)-chromen-2-one

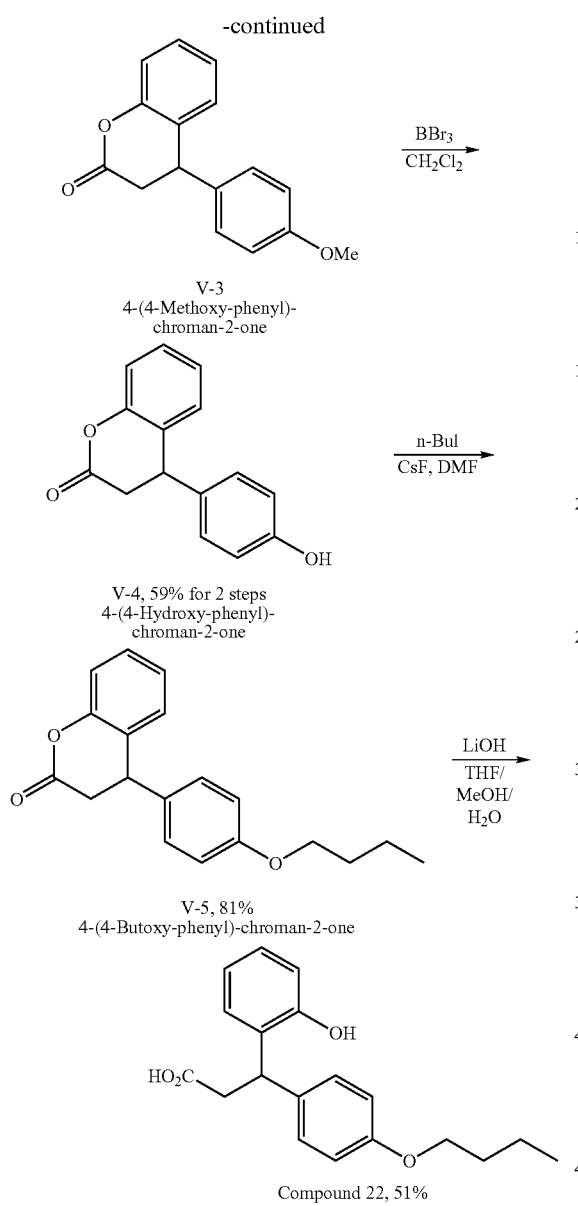

V-3
4-(4-Methoxy-phenyl)-chroman-2-one

V-4, 59% for 2 steps
4-(4-Hydroxy-phenyl)-chroman-2-one

V-5, 81%
4-(4-Butoxy-phenyl)-chroman-2-one

Compound 22, 51%

To a mixture of compound V-1 (1.58 g, 5.0 mmol) and 4-methoxyphenylboronic acid (1.52 g, 10.0 mmol) in THF (40 mL) was added $PdCl_2(PPh_3)_2$ (176 mg, 0.25 mmol), followed by $Na_2CO_3$ (2.0M in $H_2O$, 40 mL, 80 mmol). The reaction mixture was stirred at 60° C. for overnight. The cooled reaction mixture was extracted with EtOAc twice. The combined organic phase was washed successively with $H_2O$, brine and dried ($Na_2SO_4$). Concentration and chromatograph on silica gel (4:1 hexane/$CH_2Cl_2$, 4:1 hexane/EtOAc, then 2:1 hexane/EtOAc) gave 644 mg (51%) of V-2 as white solid. $^1$H NMR (300 MHz, $CDCl_3$) δ7.57 (d, J=9.0 Hz, 1H), 7.55 (t, J=9.0 Hz, 1H), 7.45-7.39 (m, 3H), 7.24 (t, J=9.0 Hz, 1H), 7.05 (d, J=9.0 Hz, 2H), 6.36 (s, 1H), 3.90 (s, 3H); MS (ES) m/z: 253 (M+H$^+$).

A mixture of V-2 (600 mg, 2.4 mmol) in EtOAc (50 mL) with Pd/C (10% w/w, 300 mg) was shaken under $H_2$ (55 psi) for 24 h. Filtration through Celite and concentration gave 538 mg of the crude V-3 as white solid. The crude solid V-3 (127 mg, 0.50 mmol) in $CH_2Cl_2$ (5 mL) at −78° C. was treated with $BBr_3$ (1.0 M in $CH_2Cl_2$, 0.75 mL, 0.75 mmol). The reaction mixture was stirred at −78° C. for 1 h, then at room temperature for 2 h. Saturated $NaHCO_3$ aqueous solution was added and the mixture was extracted with EtOAc thrice. The combined extracts were washed brine and dried ($Na_2SO_4$). Concentration and chromatograph on silica gel (2:1 hexane/EtOAc) gave 80 mg (59% for 2 steps) of V-4 as colorless oil. $^1$H NMR (300 MHz, $CDCl_3$) δ7.29 (t, J=8.6 Hz, 1H), 7.15-7.06 (m, 2H), 7.10-6.96 (m, 3H), 6.79 (d, J=8.6 Hz, 2H), 5.79 (s, 1H, OH), 4.28 (t, J=6.7 Hz, 1H), 3.10-2.94 (m, 2H); MS (ES) m/z: 263 (M+Na$^+$).

Compound V-4 (36 mg, 0.15 mmol) in DMF (1.0 mL) with CsF (69 mg, 0.45 mmol) was treated with n-butyl iodide (42 mg, 0.23 mmol). The mixture was stirred at room temperature for overnight. Chromatograph of the mixture on silica gel (10:1 hexane/EtOAc) gave 36 mg (81%) of V-5 as colorless oil. $^1$H NMR (300 MHz, $CDCl_3$) δ7.29 (t, J=8.4 Hz, 1H), 7.12 (d, J=8.4 Hz, 2H), 7.10-7.01 (m, 3H), 6.98 (d, J=8.4 Hz, 1H), 6.87 (d, J=8.7 Hz, 2H), 4.29 (dd, J=6.1, 8.1 Hz, 1H), 3.94 (t, J=6.5 Hz, 2H), 3.05 (dd, J=6.1, 15.8 Hz, 1H), 2.99 (dd, J=8.1, 15.8 Hz, 1H), 1.76 (tt, J=6.5 Hz, 2H), 1.55-1.42 (m, 2H), 0.97 (t, J=7.4 Hz, 3H); MS (ES) m/z: 297 (M+H$^+$).

Compound V-5 (36 mg, 0.12 mmol) in THF/MeOH/$H_2O$ (4:1:1 v/v/v, 6.0 mL) was treated with LiOH (1 M in $H_2O$, 1.0 mL, 1.0 mmol). The mixture was stirred at room temperature for overnight. Aqueous 1N HCl solution was added and it was extracted with EtOAc thrice. The combined extracts were washed with brine and dried over $Na_2SO_4$. Concentration and chromatograph on silica gel (20:1 $CH_2Cl_2$/MeOH) gave 19 mg (51%) of the acid 22 as white solid. $^1$H NMR (300 MHz, $CDCl_3$) δ7.18-7.03 (m, 4H), 6.90-6.75 (m, 4H), 4.74 (t, J=7.6 Hz, 1H), 3.91 (t, J=6.5 Hz, 2H), 3.00-2.98 (m, 2H), 1.73 (tt, J=6.5, 6.5 Hz, 2H), 1.53-1.40 (m, 2H), 0.95 (t, J=7.4 Hz, 3H); MS (ES) m/z: 337 (M+Na$^+$).

Example W

Compound 23

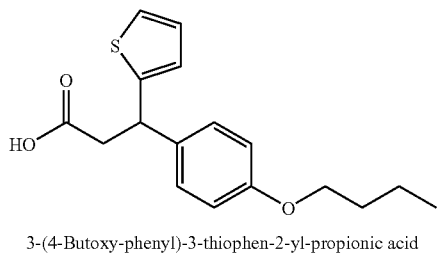

3-(4-Butoxy-phenyl)-3-thiophen-2-yl-propionic acid

Scheme W

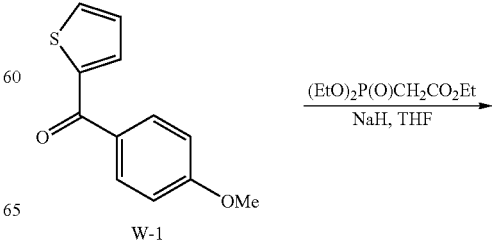

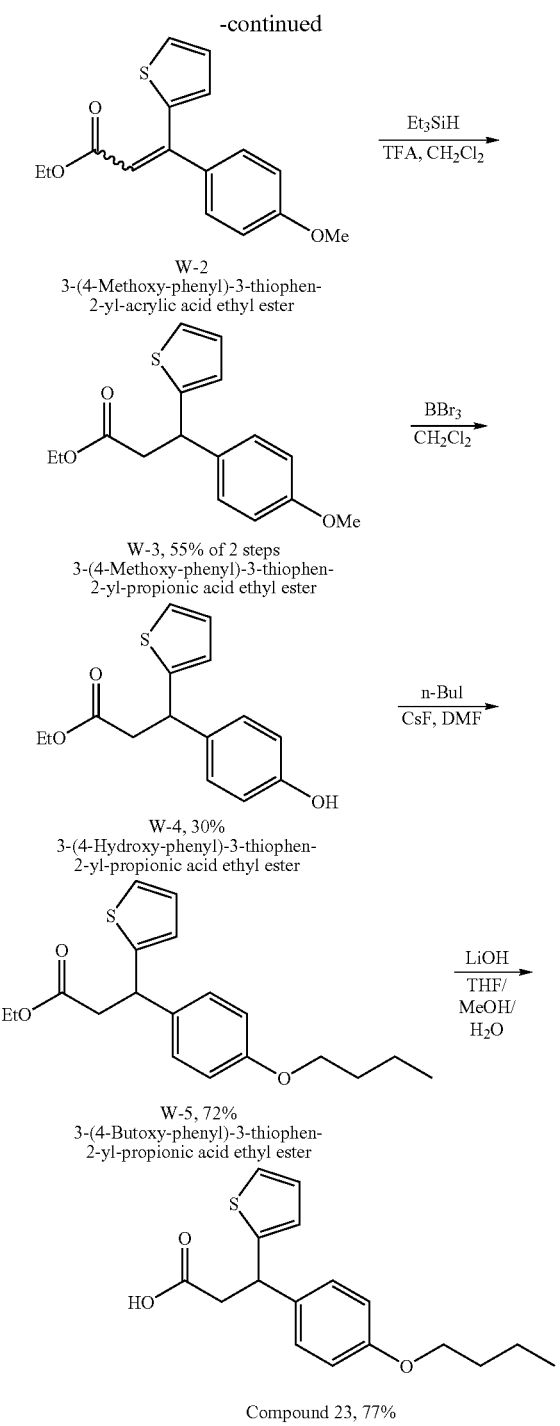

W-2
3-(4-Methoxy-phenyl)-3-thiophen-
2-yl-acrylic acid ethyl ester

W-3, 55% of 2 steps
3-(4-Methoxy-phenyl)-3-thiophen-
2-yl-propionic acid ethyl ester W-4, 30%
3-(4-Hydroxy-phenyl)-3-thiophen-
2-yl-propionic acid ethyl ester W-5, 72%
3-(4-Butoxy-phenyl)-3-thiophen-
2-yl-propionic acid ethyl ester Compound 23, 77%

(Diethoxy-phosphoryl)-acetic acid ethyl ester (3.36 g, 15.0 mmol) was added dropwise to a suspension of NaH in THF (10 ml) at 0° C. The mixture was stirred at room temperature for 30 min. A solution of compound W-1 (1.09 g, 5.0 mmol) in THF (5 mL) was added. The reaction mixture was stirred at 60° C. for overnight. The cooled mixture was poured into a saturated $NH_4Cl$ aqueous solution. The mixture was extracted with EtOAc thrice. The combined extracts were washed with $H_2O$, brine and dried ($Na_2SO_4$). Concentration gave 0.806 g of the crude W-2 as yellowish oil. The crude (0.806 g) was dissolved in $CH_2Cl_2$ (30 mL) with $Et_3SiH$ (10.7 mL, 67.2 mmol). Trifluoroacetic acid (21.5 mL, 280 mmol) was added at room temperature. After it was stirred at room temperature for 2 h, the reaction mixture was concentrated and then azeotroped with $CHCl_3$ three times. The residue was purified by chromatograph on silica gel (4:1 hexane/EtOAc) to afford 800 mg (55% for 2 steps) of W-3 as colorless oil. $^1$H NMR (400 MHz, $CDCl_3$) δ7.20 (d, J=8.0 Hz, 2H), 7.13 (d, J=8.0 Hz, 1H), 6.91-6.87 (m, 1H), 6.86-6.78 (m, 3H), 4.72 (t, J=8.0 Hz, 1H), 4.05 (q, J=8.0 Hz, 2H), 3.78 (s, 3H), 3.08 (dd, J=8.0, 16.0 Hz, 1H), 2.98 (dd, J=8.0, 16.0 Hz, 1H), 1.14 (t, J=8.0 Hz, 3H); MS (ES) m/z: 291 (M+H$^+$).

A solution of W-3 (1.273 g, 4.39 mmol) in $CH_2Cl_2$ (45 mL) at −78° C. was treated with $BBr_3$ (1.0 M in $CH_2Cl_2$, 6.6 mL, 6.6 mmol,). The reaction mixture was stirred at room temperature for overnight. Saturated $NaHCO_3$ aqueous solution was added and the mixture was extracted with $CH_2Cl_2$ thrice. The combined extracts were washed $H_2O$, brine and dried ($Na_2SO_4$). Concentration and chromatograph on silica gel (4:1 hexane/EtOAc) gave 361 mg (30%) of W-4 as yellowish oil. $^1$H NMR (400 MHz, $CDCl_3$) δ7.14-7.10 (m, 3H), 6.90 (dd, J=4.0, 8.0 Hz, 1H), 6.81 (d, J=4.0 Hz, 1H), 6.73 (d, J=8.0 Hz, 2H), 4.69 (t, J=8.0 Hz, 1H), 4.05 (q, J=8.0 Hz, 2H), 3.09 (dd, J=8.0, 16.0 Hz, 1H), 2.99 (dd, J=8.0, 16.0 Hz, 1H), 1.14 (t, J=8.0 Hz, 3H); MS (ES) m/z: 299 (M+Na$^+$).

Compound W-4 (79 mg, 0.29 mmol) in DMF (1.5 mL) with CsF (130 mg, 0.86 mmol) was treated with n-butyl iodide (79 mg, 0.43 mmol). The mixture was stirred at room temperature for overnight. Chromatograph of the mixture on silica gel (20:1 hexane/EtOAc, then 10:1 hexane/EtOAc) gave 69 mg (72%) of W-5 as colorless oil. $^1$H NMR (400 MHz, $CDCl_3$) δ7.18 (d, J=8.0 Hz, 2H), 7.13 (d, J=8.0 Hz, 1H), 6.90 (dd, J=4.0, 8.0 Hz, 1H), 6.86-6.80 (m, 3H), 4.70 (t, J=8.0 Hz, 1H), 4.05 (q, J=8.0 Hz, 2H), 3.93 (t, J=8.0H, 2H), 3.08 (dd, J=8.0, 16.0 Hz, 1H), 2.98 (dd, J=8.0, 16.0 Hz, 1H), 1.75 (tt, J=6.5 Hz, 2H), 1.49 (tq, J=8.0, 8.0 Hz, 2H), 1.14 (t, J=8.0 Hz, 3H) 0.96 (t, J=8.0 Hz, 3H); MS (ES) m/z: 333 (M+H$^+$).

Compound W-5 (61 mg, 0.18 mmol) in THF/MeOH/$H_2O$ (4:1:1 v/v/v, 6 mL) was treated with LiOH (1 M in $H_2O$, 1.0 mL, 1.0 mmol). The mixture was stirred at room temperature for overnight. Saturated $NH_4Cl$ aqueous solution was added and it was extracted with EtOAc thrice. The combined extracts were washed with brine and dried over $Na_2SO_4$. Concentration and chromatograph on silica gel (20:1 $CH_2Cl_2$/MeOH) gave 43 mg (77%) of the acid 23 as white solid. $^1$H NMR (400 MHz, $CDCl_3$) δ7.20-7.11 (m, 3H), 6.93-6.80 (m, 4H), 4.69 (t, J=7.6 Hz, 1H), 3.93 (t, J=6.5 Hz, 2H), 3.13 (dd, J=7.6, 15.9 Hz, 1H), 3.03 (dd, J=7.6, 15.9 Hz, 1H), 1.75 (tt, J=6.5 Hz, 2H), 1.53-1.45 (m, 2H), 0.96 (t, J=7.4 Hz, 3H); MS (ES) m/z: 305 (M+H$^+$).

Example X

Compound 24

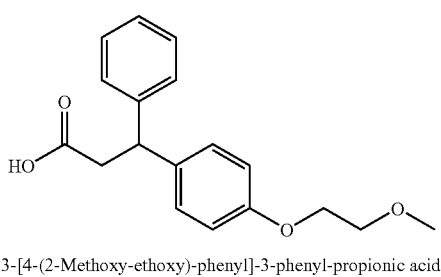

3-[4-(2-Methoxy-ethoxy)-phenyl]-3-phenyl-propionic acid

Scheme X

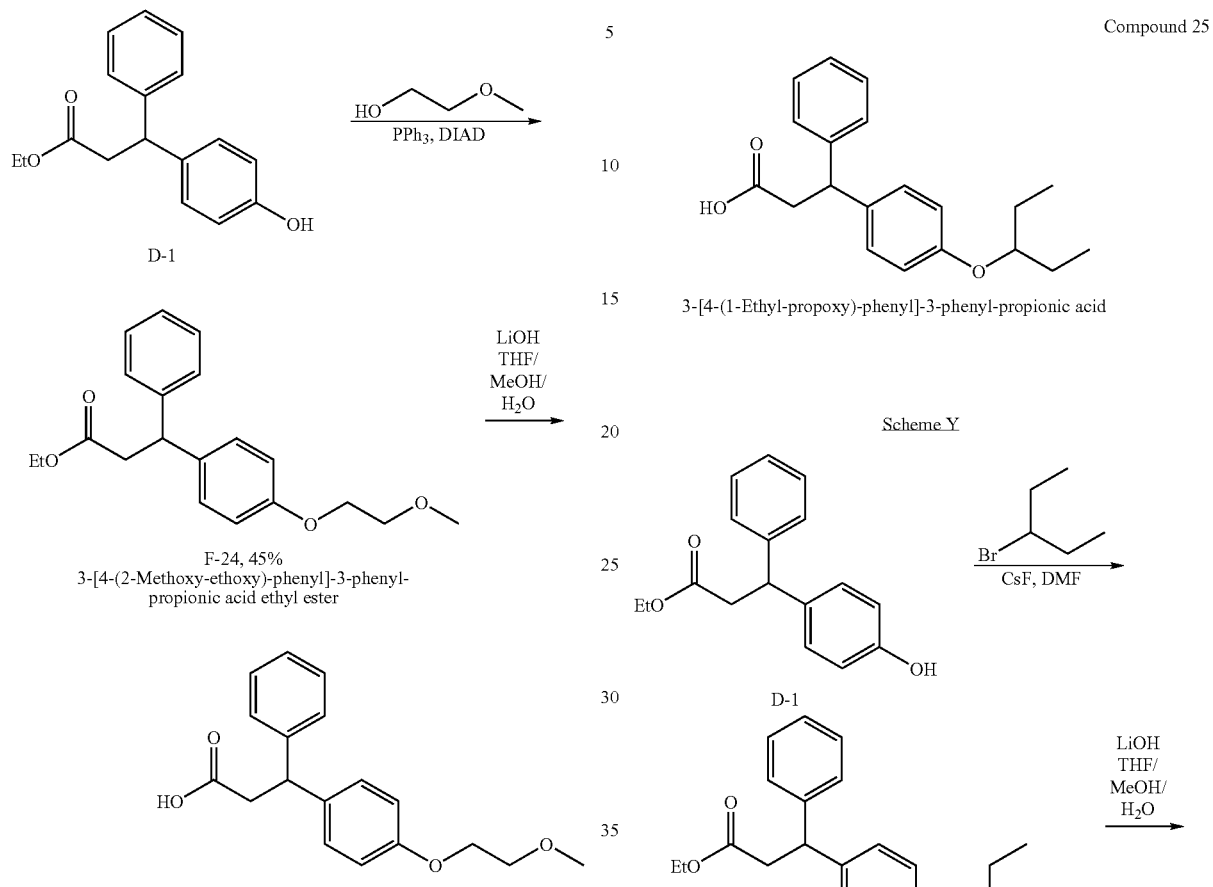

A solution of compound D-1 (54 mg, 0.20 mmol), 2-methoxy-ethanol (15 mg, 0.20 mmol) and $PPh_3$ (63 mg, 0.24 mmol) in THF (1 mL) was treated with DIAD (43 mg, 0.21 mmol). The reaction was stirred at room temperature for 48 h. Concentration and chromatograph on silica gel (4:1 hexane/EtOAc) gave 30 mg (45%) of F-24 as colorless oil. $^1H$ NMR (300 MHz, $CDCl_3$) δ7.30-7.16 (m, 5H), 7.14 (d, J=9.0 Hz, 2H), 6.84 (d, J=9.0 Hz, 2H), 4.49 (t, J=9.0 Hz, 1H), 4.09-3.98 (m, 4H), 3.71 (t, J=6.0 Hz, 2H), 3.42 (s, 3H), 3.01 (d, J=9.0 Hz, 2H), 1.10 (t, J=6.0 Hz, 3H); MS (ES) m/z: 351 (M+$Na^+$).

Compound F-24 (30 mg, 0.09 mmol) in THF/MeOH/$H_2O$ (4:1:1 v/v/v, 6 mL) was treated with LiOH (1M in $H_2O$, 1.0 mL, 1.0 mmol). The mixture was stirred at room temperature overnight. Aqueous 1N HCl solution was added to neutralize the reaction mixture and then it was extracted with EtOAc thrice. The combined extracts were washed with brine and dried over $Na_2SO_4$. Concentration and chromatograph on silica gel (20:1 $CH_2Cl_2$/MeOH) gave 15 mg (55%) of the acid 24 as sticky oil. $^1H$ NMR (300 MHz, $CDCl_3$) δ7.30-7.14 (m, 5H), 7.12 (d, J=9.0 Hz, 2H), 6.83 (d, J=9.0 Hz, 2H), 4.46 (t, J=7.5 Hz, 1H), 4.06 (t, J=6.0 Hz, 2H), 3.72 (t, J=6.0 Hz, 2H), 3.42 (s, 3H), 3.03 (d, J=7.5 Hz, 2H); MS (ES) m/z: 323 (M+$Na^+$).

Example Y

To a mixture of D-1 (108 mg, 0.40 mmol) and CsF (182 mg, 1.2 mmol) in DMF (2 mL) was added 3-Bromo-pentane (91 mg, 0.60 mmol). The reaction mixture was stirred at room temperature for overnight. Chromatograph on silica gel (10:1 hexane/EtOAc) gave 66 mg (48%) of F-25 as colorless oil. $^1H$ NMR (300 MHz, $CDCl_3$) δ7.30-7.16 (m, 5H), 7.12 (d, J=8.0 Hz, 2H), 6.79 (d, J=8.0 Hz, 2H), 4.48 (t, J=9.0 Hz, 1H), 4.06-3.99 (m, 3H), 3.01 (d, J=9.0 Hz, 2H), 1.71-1.58 (m, 4H), 1.10 (t, J=7.5 Hz, 3H), 0.92 (t, J=7.5 Hz, 6H); MS (ES) m/z: 363 (M+$Na^+$).

Compound F-25 (66 mg, 0.19 mmol) in THF/MeOH/(4:1:1 v/v/v, 6 mL) was treated with LiOH (1M in $H_2O$, 1.0 mL, 1.0 mmol). The mixture was stirred at room temperature for overnight. Saturated $NH_4Cl$ aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 41 mg (68%) of the acid 25 as white solid. $^1$H NMR (400 MHz, CDCl$_3$) δ7.30-7.15 (m, 5H), 7.09 (d, J=8.0 Hz, 2H), 6.79 (d, J=8.0 Hz, 2H), 4.45 (t, J=8.0 Hz, 1H), 4.06-4.01 (m, 1H), 3.04 (d, J=8.0 Hz, 2H), 1.67-1.60 (m, 4H), 0.92 (t, J=7.5 Hz, 6H); MS (ES) m/z: 335 (M+Na$^+$).

Example Z

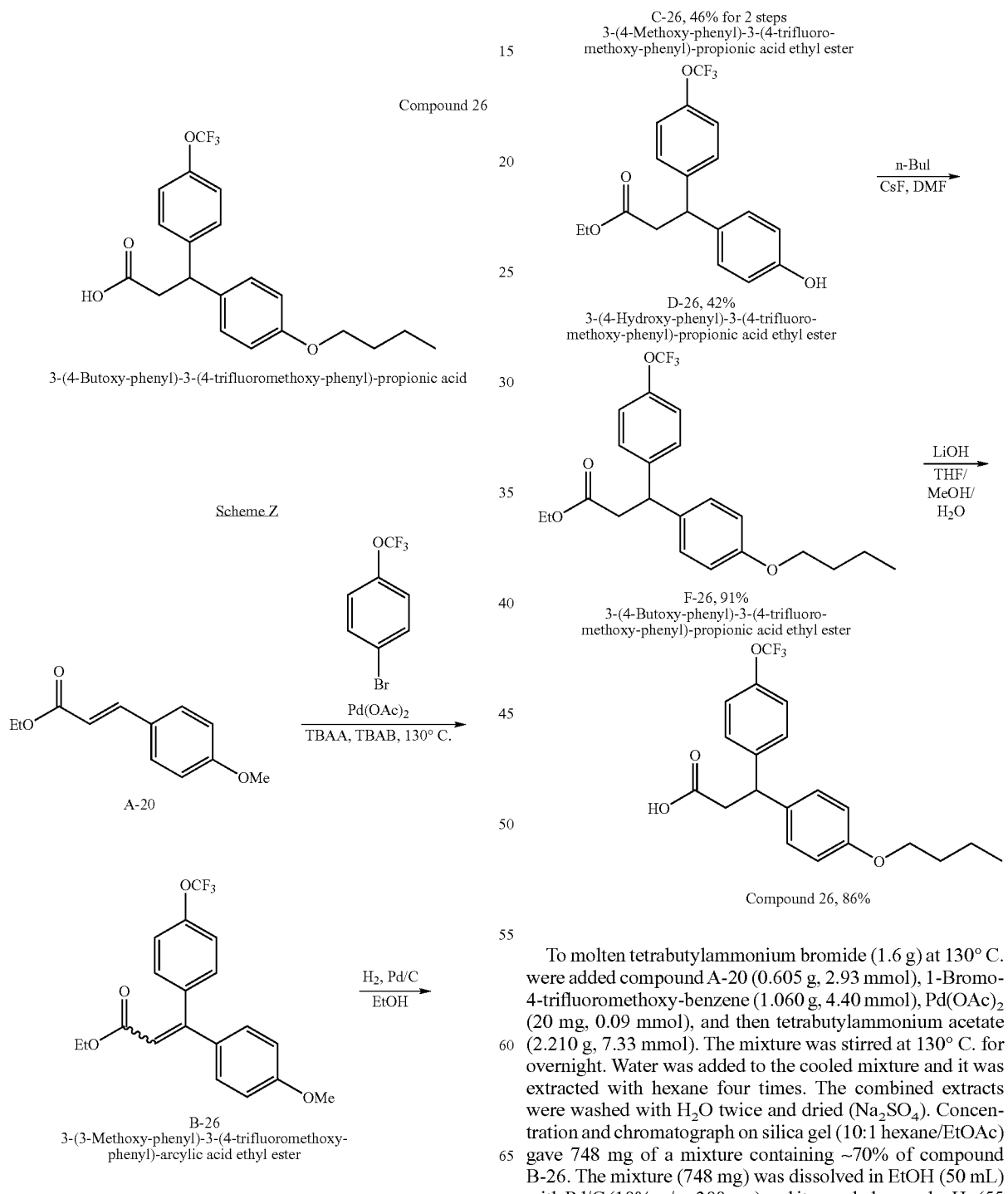

To molten tetrabutylammonium bromide (1.6 g) at 130° C. were added compound A-20 (0.605 g, 2.93 mmol), 1-Bromo-4-trifluoromethoxy-benzene (1.060 g, 4.40 mmol), Pd(OAc)$_2$ (20 mg, 0.09 mmol), and then tetrabutylammonium acetate (2.210 g, 7.33 mmol). The mixture was stirred at 130° C. for overnight. Water was added to the cooled mixture and it was extracted with hexane four times. The combined extracts were washed with H$_2$O twice and dried (Na$_2$SO$_4$). Concentration and chromatograph on silica gel (10:1 hexane/EtOAc) gave 748 mg of a mixture containing ~70% of compound B-26. The mixture (748 mg) was dissolved in EtOH (50 mL) with Pd/C (10% w/w, 300 mg) and it was shaken under H$_2$ (55 psi) overnight. Filtration through Celite and concentration gave the crude. Purification by chromatograph on silica gel (20:1 hexane/EtOAc) gave 497 mg (46% for 2 steps) of C-26 as colorless oil. $^1$H NMR (400 MHz, CDCl$_3$) δ7.24 (d, J=8.0 Hz, 2H), 7.13 (d, J=8.0 Hz, 2H), 7.11 (d, J=8.0 Hz, 2H), 6.83 (d, J=8.0 Hz, 2H), 4.51 (t, J=8.0 Hz, 1H), 4.03 (q, J=8.0 Hz, 2H), 3.77 (s, 3H), 2.99 (d, J=8.0 Hz, 2H), 1.11 (t, J=8.0 Hz, 3H); MS (ES) m/z: 391 (M+Na$^+$).

Compound C-26 (473 mg, 1.29 mmol) in CH$_2$Cl$_2$ (15 mL) at −78° C. was treated with BBr$_3$ (1.0 M in CH$_2$Cl$_2$, 1.93 ml, 1.93 mmol,). The mixture was stirred at room temperature overnight. Saturated NaHCO$_3$ aqueous solution was added to the cooled (0° C.) reaction mixture. The mixture was extracted with EtOAc thrice. The combined extracts were washed with H$_2$O, brine and dried (Na$_2$SO$_4$). Concentration and chromatograph on silica gel (4:1 hexane/EtOAc) give 190 mg (42%) of D-26 as colorless oil. $^1$H NMR (400 MHz, CDCl$_3$) δ7.23 (d, J=8.0 Hz, 2H), 7.11 (d, J=8.0 Hz, 2H), 7.08 (d, J=8.0 Hz, 2H), 6.75 (d, J=8.0 Hz, 2H), 4.71 (s, OH), 4.49 (t, J=8.0 Hz, 1H), 4.04 (q, J=8.0 Hz, 2H), 2.99 (d, J=8.0 Hz, 2H), 1.11 (t, J=8.0 Hz, 3H); MS (ES) m/z: 377 (M+Na$^+$).

Compound D-26 (64 mg, 0.18 mmol) in DMF (0.6 mL) with CsF (82 mg, 0.54 mmol) was treated with n-butyl iodide (50 mg, 0.27 mmol). The mixture was stirred at room temperature overnight. Chromatograph of the mixture on silica gel (20:1 hexane/EtOAc) gave 67 mg (91%) of F-26 as colorless oil. $^1$H NMR (400 MHz, CDCl$_3$) δ7.24 (d, J=8.0 Hz, 2H), 7.11 (d, J=8.0 Hz, 4H overlap), 6.82 (d, J=8.0 Hz, 2H), 4.50 (t, J=8.0 Hz, 1H), 4.03 (q, J=8.0 Hz, 2H), 3.91 (t, J=8.0 Hz, 2H), 2.99 (d, J=8.0 Hz, 2H), 1.73 (tt, J=8.0 Hz, 2H), 1.47 (tq, J=8.0 Hz, 2H), 1.11 (t, J=8.0 Hz, 3H), 0.96 (t, J=8.0 Hz, 3H); MS (ES) m/z: 433 (M+Na$^+$).

Compound F-26 (56 mg, 0.14 mmol) in THF/MeOH/H$_2$O (4:1:1 v/v/v, 8.4 mL) was treated with LiOH (1M in H$_2$O, 1.4 mL, 1.4 mmol). The mixture was stirred at room temperature overnight. Saturated NH$_4$Cl aqueous solution was added and it was extracted with EtOAc thrice. The combined extracts were washed with brine and dried over Na$_2$SO$_4$. The combined extracts were washed with brine and dried over Na$_2$SO$_4$. Concentration and chromatograph on silica gel (20:1 CH$_2$Cl$_2$/MeOH) gave 44 mg (84%) of the acid 26 as colorless sticky oil. $^1$H NMR (300 MHz, CDCl$_3$) δ7.22 (d, J=8.0 Hz, 2H), 7.14-7.08 (m, 4H), 6.82 (d, J=8.0 Hz, 2H), 4.47 (t, J=8.0 Hz, 1H), 3.91 (t, J=8.0 Hz, 2H), 3.03 (d, J=8.0 Hz, 2H), 1.74 (tt, J=8.0 Hz, 2H), 1.47 (tq, J=8.0 Hz, 2H), 0.95 (t, J=8.0 Hz, 3H); MS (ES) m/z: 405 (M+Na$^+$).

Example AA

Compound 27

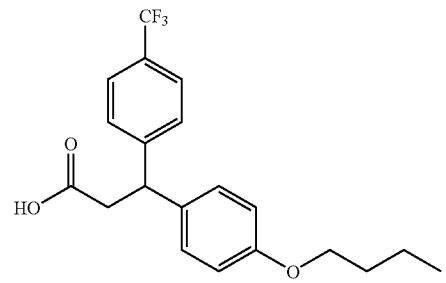

3-(4-Butoxy-phenyl)-3-(4-trifluoromethyl-phenyl)-propionic acid

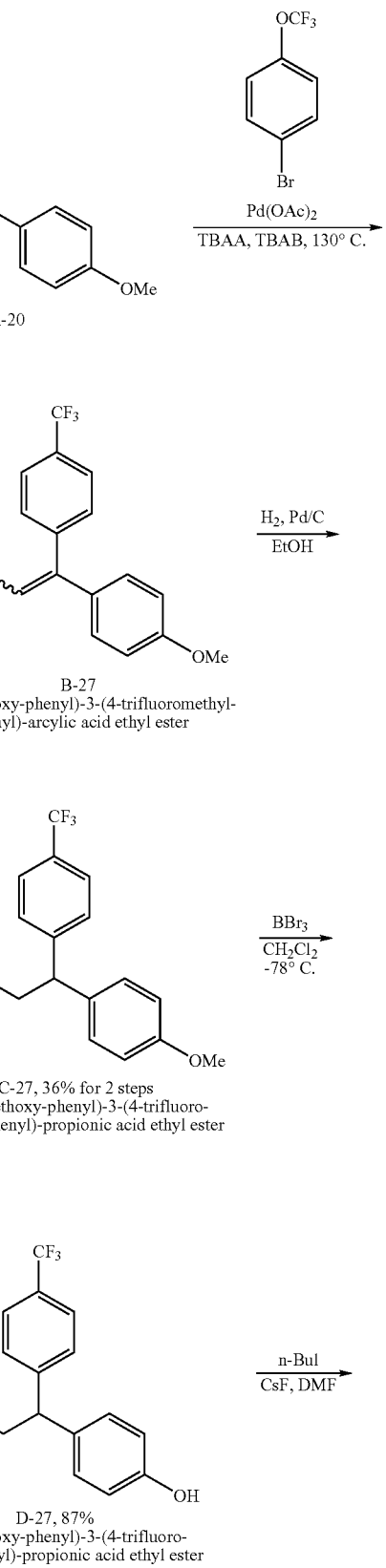

Scheme AA

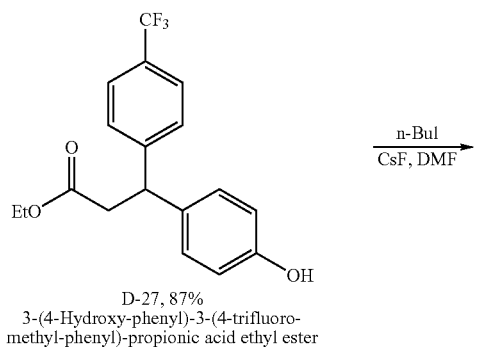

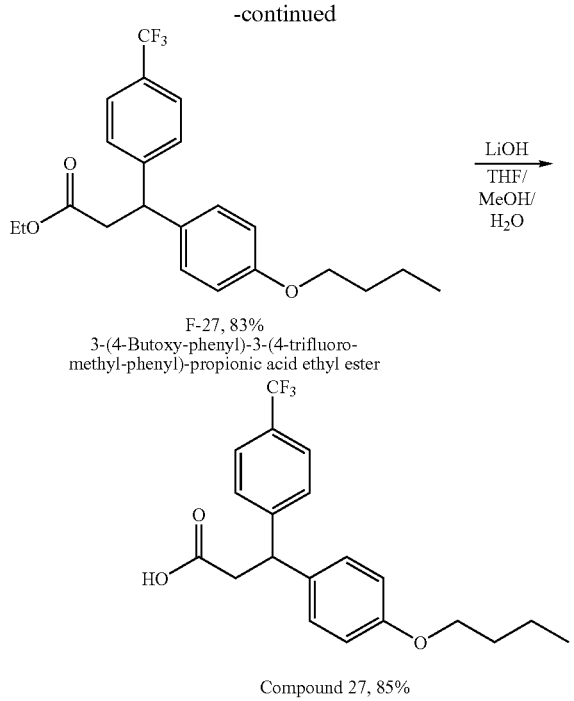

F-27, 83%
3-(4-Butoxy-phenyl)-3-(4-trifluoro-methyl-phenyl)-propionic acid ethyl ester Compound 27, 85%

To molten tetrabutylammonium bromide (1.6 g) at 130° C. were added 3-(4-Methoxy-phenyl)-acrylic acid ethyl ester (0.605 g, 2.93 mmol), 1-Bromo-4-trifluoromethyl-benzene (0.990 g, 4.40 mmol), Pd(OAc)$_2$ (20 mg, 0.09 mmol), and then tetrabutylammonium acetate (2.210 g, 7.33 mmol). The mixture was stirred at 130° C. overnight. Water was added to the cooled mixture and it was extracted with hexane four times. The combined extracts were washed with H$_2$O twice and dried (Na$_2$SO$_4$). Concentration and chromatograph on silica gel (10:1 hexane/EtOAc) gave 638 mg of a mixture containing ~60% of B-27. The mixture (638 mg) was dissolved in EtOH (50 mL) with Pd/C (10% w/w, 300 mg) and it was shaken under H$_2$ (55 psi) overnight. Filtration through Celite and concentration gave the crude. Purification by chromatograph on silica gel (20:1 hexane/EtOAc) gave 373 mg (36% for 2 steps) of C-27 as colorless oil. $^1$H NMR (400 MHz, CDCl$_3$) δ7.53 (d, J=7.5 Hz, 2H), 7.34 (d, J=7.5 Hz, 2H), 7.13 (d, J=7.5 Hz, 2H), 6.83 (d, J=7.5 Hz, 2H), 4.56 (t, J=9.0 Hz, 1H), 4.04 (q, J=7.5 Hz, 2H), 3.77 (s, 3H), 3.03 (d, J=9.0 Hz, 2H), 1.12 (t, J=7.5 Hz, 3H).

Compound C-27 (352 mg, 1.00 mmol) in CH$_2$Cl$_2$ (12 mL) at −78° C. was treated with BBr$_3$ (1.0 M in CH$_2$Cl$_2$, 1.50 ml, 1.50 mmol,). The mixture was stirred at room temperature overnight. Anhydrous MeOH was added and the mixture was evaporated under vacuum. This process was repeated three times. The residue was purified by chromatograph on silica gel (4:1 hexane/EtOAc) give 287 mg (87%) of a 1:1 mixture of the methyl ester and the ethyl ester of D-27.

Compound D-27 (62 mg) in DMF (1.5 mL) with CsF (86 mg, 0.56 mmol) was treated with n-butyl iodide (52 mg, 0.28 mmol). The mixture was stirred at room temperature overnight. Chromatograph of the mixture on silica gel (10:1 hexane/EtOAc) gave 60 mg (83%) of a 1:1 mixture of the methyl ester and the ethyl ester of F-27.

Compound F-27 (60 mg) in THF/MeOH/H$_2$O (4:1:1 v/v/v, 8.4 mL) was treated with LiOH (1M in H$_2$O, 1.4 mL, 1.4 mmol). The mixture was stirred at room temperature overnight. Aqueous 1N HCl solution was added to neutralize the reaction mixture and then it was extracted with EtOAc thrice. The combined extracts were washed with brine and dried over Na$_2$SO$_4$. Concentration and chromatograph on silica gel (20:1 CH$_2$Cl$_2$/MeOH) gave 48 mg (85%) of the acid 27 as colorless sticky oil. $^1$H NMR (300 MHz, CDCl$_3$) δ7.52 (d, J=6.0 Hz, 2H), 7.32 (d, J=6.0 Hz, 2H), 7.10 (d, J=9.0 Hz, 2H), 6.82 (d, J=9.0 Hz, 2H), 4.51 (t, J=7.5 Hz, 1H), 3.91 (t, J=6.0 Hz, 2H), 3.06 (d, J=7.5 Hz, 2H), 1.72 (tt, J=6.0 Hz, 2H), 1.46 (tq, J=6.0 Hz, 2H), 0.95 (t, J=6.0 Hz, 3H); MS (ES) m/z: 389 (M+Na$^+$).

Example AB

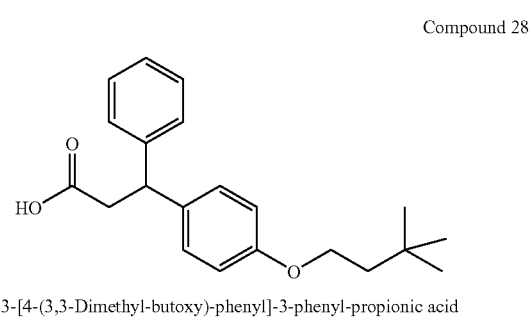

Compound 28

3-[4-(3,3-Dimethyl-butoxy)-phenyl]-3-phenyl-propionic acid

Scheme AB

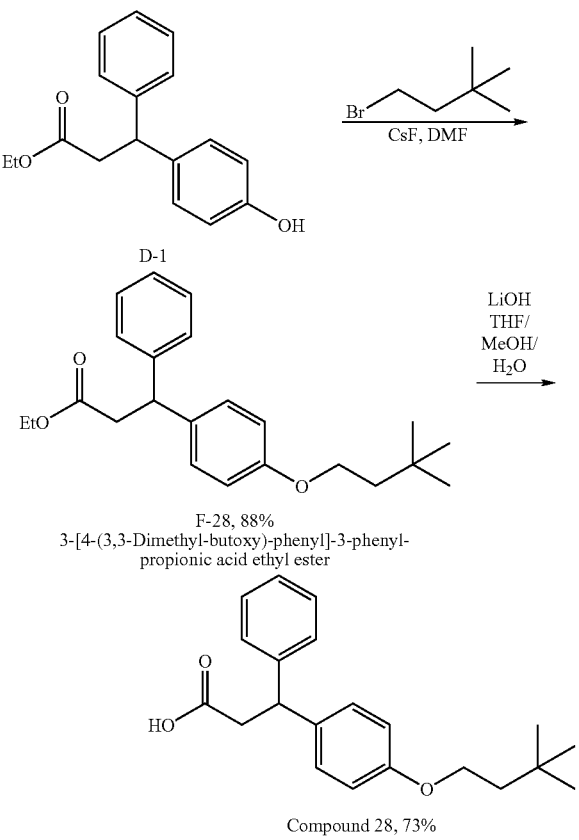

F-28, 88%
3-[4-(3,3-Dimethyl-butoxy)-phenyl]-3-phenyl-propionic acid ethyl ester Compound 28, 73%

To a mixture of compound D-1 (108 mg, 0.40 mmol) and CsF (182 mg, 1.2 mmol) in DMF (2 mL) was added 1-Bromo-3,3-dimethyl-butane (99 mg, 0.60 mmol). The reaction mixture was stirred at 80° C. for 2 h. Chromatograph on silica gel (10:1 hexane/EtOAc) gave 125 mg (88%) of F-28 as colorless oil. $^1$H NMR (400 MHz, CDCl$_3$) δ 7.30-7.17 (m, 5H), 7.14 (d, J=6.7 Hz, 2H), 6.80 (d, J=6.7 Hz, 2H), 4.49 (t, J=8.1 Hz, 1H), 4.03 (q, J=7.2 Hz, 2H), 3.97 (t, J=7.3 Hz, 2H), 3.01 (d, J=8.1 Hz, 2H), 1.69 (t, J=7.3 Hz, 2H), 1.11 (t, J=7.2 Hz, 3H), 0.97 (s, 9H); MS (ES) m/z: 355 (M+H$^+$).

Compound F-28 (120 mg, 0.34 mmol) in THF/MeOH/H$_2$O (4:1:1 v/v/v, 12 mL) was treated with LiOH (1M in H$_2$O, 2.0 mL, 2.0 mmol). The mixture was stirred at room temperature overnight. Aqueous 1N HCl solution was added to neutralize the reaction mixture and then it was extracted with EtOAc thrice. The combined extracts were washed with brine and dried over Na$_2$SO$_4$. Concentration and chromatograph on silica gel (20:1 CH$_2$Cl$_2$/MeOH) gave 81 mg (73%) of the acid 28 as white solid. $^1$H NMR (300 MHz, CDCl$_3$) δ 7.30-7.17 (m, 5H), 7.12 (d, J=8.6 Hz, 2H), 6.80 (d, J=8.6 Hz, 2H), 4.47 (t, J=8.0 Hz, 1H), 3.97 (t, J=7.3 Hz, 2H), 3.02 (d, J=8.0 Hz, 2H), 1.69 (t, J=7.3 Hz, 2H), 0.96 (s, 9H); MS (ES) m/z: 349 (M+Na$^+$).

Example AC

Compound 29

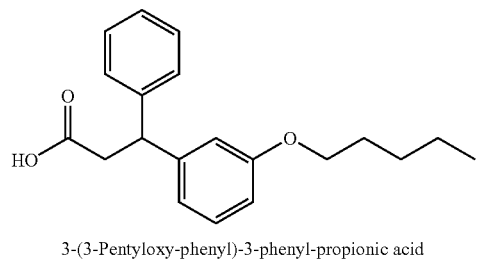

3-(3-Pentyloxy-phenyl)-3-phenyl-propionic acid

Scheme AC

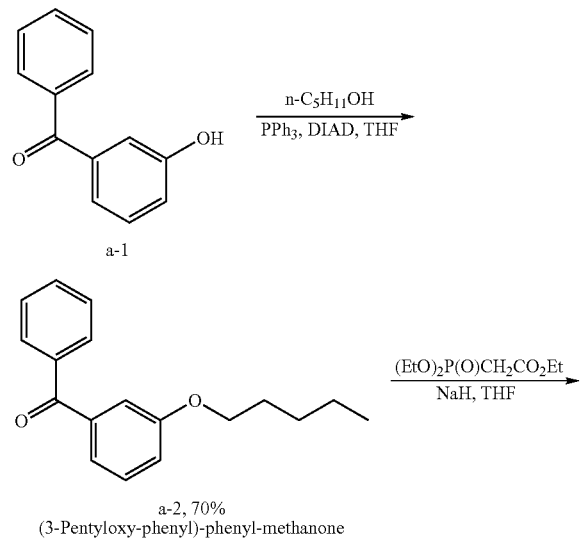

a-1 a-2, 70%
(3-Pentyloxy-phenyl)-phenyl-methanone

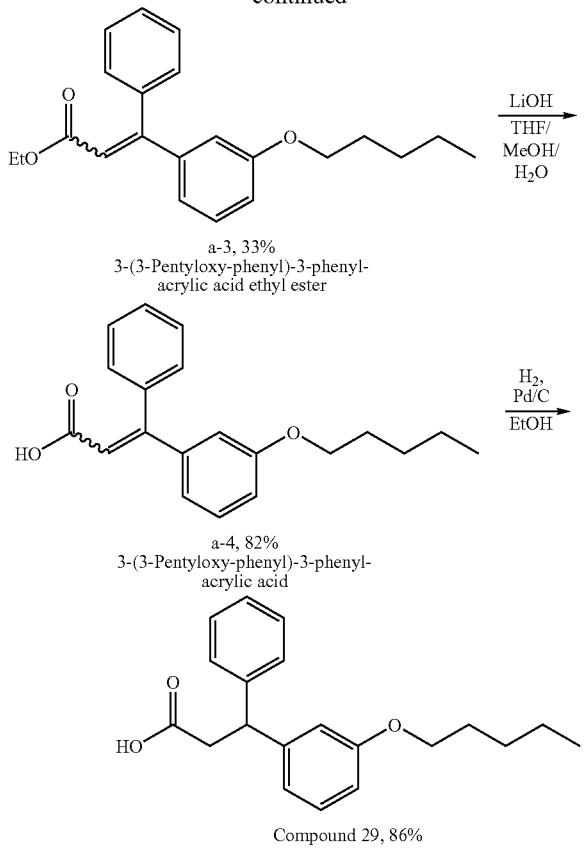

a-3, 33%
3-(3-Pentyloxy-phenyl)-3-phenyl-acrylic acid ethyl ester a-4, 82%
3-(3-Pentyloxy-phenyl)-3-phenyl-acrylic acid Compound 29, 86%

To a solution of a-1 (0.990 g, 5.0 mmol), n-pentyl alcohol (0.440 g, 5.0 mmol) and PPh$_3$ (1.574 g, 6.0 mmol) in THF (20 mL) was added DIAD (1.112 g, 5.5 mmol). The solution was stirred at room temperature overnight. Concentration and chromatograph on silica gel (20:1 hexane/EtOAc) gave 0.940 g (70%) of a-2 as colorless oil. $^1$H NMR (400 MHz, CDCl$_3$) δ 7.81 (d, J=8.0 Hz, 2H), 7.59 (t, J=8.0 Hz, 1H), 7.51-7.46 (m, 2H), 7.39-7.31 (m, 3H), 7.13 (m, 1H), 7.14-7.10 (m, 1H), 4.01 (t, J=8.0 Hz, 2H), 1.81 (tt, J=8.0, 8.0 Hz, 2H), 1.57-1.43 (m, 4H), 0.93 (t, J=8.0 Hz, 3H); MS (ES) m/z: 269 (M+H$^+$).

(Diethoxy-phosphoryl)-acetic acid ethyl ester (258 mg, 1.15 mmol) was added dropwise to a suspension of NaH (60% w/w in mineral oil, 43 mg, 1.07 mmol) in THF (3 mL) at 0° C. The mixture was stirred at room temperature for 30 min. A solution of a-2 (103 mg, 0.38 mmol) in THF (2 mL) was added. The reaction mixture was stirred at 60° C. for overnight. The cooled mixture was poured into a saturated NH$_4$Cl aqueous solution. The mixture was extracted with EtOAc thrice. The combined extracts were washed with H$_2$O, brine and dried (Na$_2$SO$_4$). Concentration and chromatograph on silica gel (20:1 hexane/EtOAc) gave 128 mg (33%) of a 1:1 Z/E mixture of a-3 as colorless oil.

Compound a-3 (128 mg, 0.38 mmol) in THF/MeOH/H$_2$O (4:1:1 v/v/v, 12 mL) was treated with LiOH (1 M in H$_2$O, 2.0 mL, 2.0 mmol). The mixture was stirred at room temperature for overnight. Saturated NH$_4$Cl aqueous solution was added and it was extracted with EtOAc thrice. The combined extracts were washed with brine and dried over Na$_2$SO$_4$. Concentration and chromatograph on silica gel (20:1 CH$_2$Cl$_2$/MeOH) gave 97 mg (82%) of the acid a-4 as colorless oil. $^1$H NMR (300 MHz, CDCl$_3$) δ 7.38-7.16 (m, 6H), 6.91-6.72 (m, 3H), 6.31 (s, 1H), 3.91 (q, J=6.0 Hz, 2H), 1.81-1.69 (m, 2H), 1.48-1.30 (m, 4H), 0.92 (t, J=7.5 Hz, 3H); MS (ES) m/z: 333 (M+Na$^+$). A mixture of a-4 (58 mg, 0.19 mmol) in EtOH (10 mL) with Pd/C (10% w/w, 50 mg) was shaken under H$_2$ (55 psi) for 2.5 h. Filtration through Celite and concentration gave the crude. Purification by chromatograph on silica gel (20:1 CH$_2$Cl$_2$/MeOH) gave 51 mg (86%) of Compound 29 as colorless oil. $^1$H NMR (400 MHz, CDCl$_3$) δ7.32-7.15 (m, 6H), 6.83-6.70 (m, 3H), 6.31 (s, 1H), 4.48 (t, J=8.0 Hz, 1H), 3.90 (q, J=8.0 Hz, 2H), 3.07 (d, J=8.0 Hz, 2H), 1.75 (tt, J=8.0, 8.0 Hz, 2H), 1.46-1.32 (m, 4H), 0.90 (t, J=8.0 Hz, 3H); MS (ES) m/z: 335 (M+Na$^+$).

Example AD compound 30

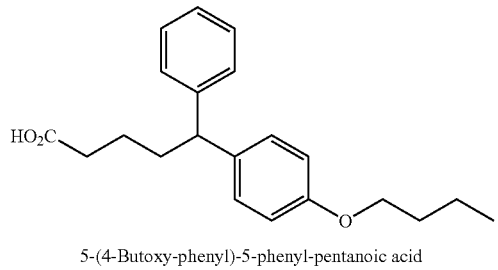

5-(4-Butoxy-phenyl)-5-phenyl-pentanoic acid

Scheme AD

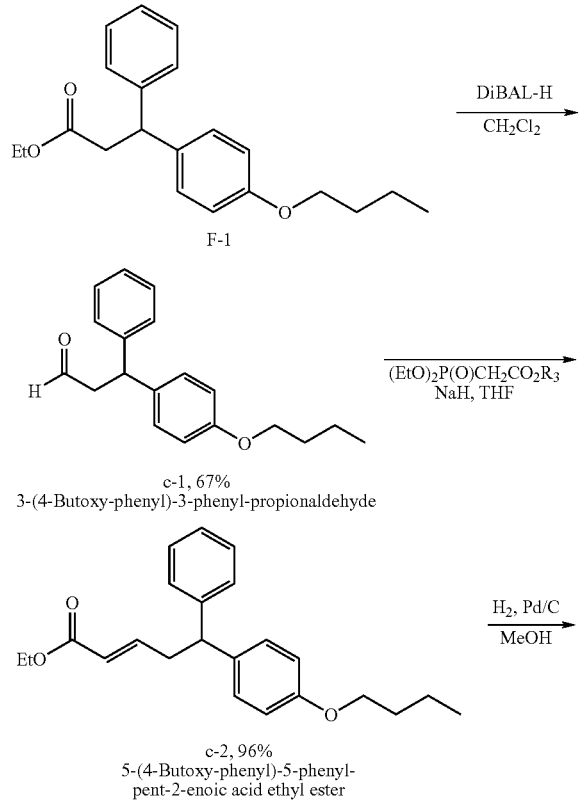

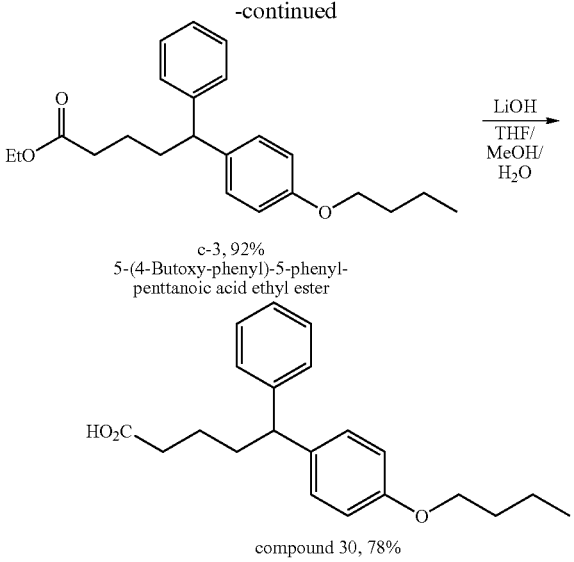

To a solution of compound F-1 (311 mg, 0.95 mmol) in CH$_2$Cl$_2$ (9 mL) at −78° C. was added dropwise DiBAL-H (1.0 M in CH$_2$Cl$_2$, 2.50 mL, 2.50 mmol). The reaction mixture was stirred at −78° C. for 1 h. Saturated Rochelle's salt aqueous solution was added and it was stirred vigorously at room temperature until the two layers became clear. It was extracted with EtOAc thrice and the combined extracts were dried (Na$_2$SO$_4$) and concentrated. The residue was purified by chromatograph on silica gel (10:1 hexane.EtOAc) to give 179 mg (67%) of the aldehyde c-1 as colorless oil. $^1$H NMR (400 MHz, CDCl$_3$) δ9.72 (s, 1H), 7.30-7.16 (m, 5H), 7.12 (d, J=8.0 Hz, 2H), 6.82 (d, J=8.0 Hz, 2H), 4.56 (t, J=8.0 Hz, 1H), 3.91 (t, J=7.0 Hz, 2H), 3.12 (d, J=8.0 Hz, 2H), 1.73 (tt, J=7.0, 7.0 Hz, 2H), 1.44 (tq, J=7.0, 7.0 Hz, 2H), 0.96 (t, J=7.0 Hz, 3H); MS (ES) m/z: 305 (M+Na$^+$).

A mixture of the aldehyde c-1 (88 mg, 0.31 mmol) and (triphenylphosphanylidene)-acetic acid ethyl ester (230 mg, 0.62 mmol) in toluene (8 mL) was heated at reflux for 1.5 h. Concentration and chromatograph on silica gel (10:1 hexane/EtOAc) gave 106 mg (96%) of c-2 as colorless oil. $^1$H NMR (400 MHz, CDCl$_3$) δ7.30-7.16 (m, 5H), 7.10 (d, J=8.0 Hz, 2H), 6.84 (dt, J=16.0, 8.0 Hz, 1H), 6.81 (d, J=8.0 Hz, 2H), 5.80 (d, J=16.0 Hz, 1H), 4.12 (q, J=8.0 Hz, 2H), 4.04 (t, J=8.0 Hz, 1H), 3.91 (t, J=7.0 Hz, 2H), 2.92 (t, J=8.0 Hz, 2H), 1.74 (tt, J=7.0 Hz, 2H), 1.47 (tq, J=7.0 Hz, 2H), 1.24 (t, J=8.0 Hz, 3H), 0.96 (t, J=7.0 Hz, 3H); MS (ES) m/z: 353 (M+H$^+$).

Compound c-2 (96 mg, 0.27 mmol) was dissolved in MeOH (15 mL) with Pd/C (10% w/w, 90 mg) and it was shaken under H$_2$ (55 psi) for 2 h. Filtration through Celite and concentration gave the crude. Purification by chromatograph on silica gel (10:1 hexane/EtOAc) gave 89 mg (92%) of c-3 as colorless oil. $^1$H NMR (400 MHz, CDCl$_3$) δ730-7.15 (m, 5H), 7.11 (d, J=8.0 Hz, 2H), 6.80 (d, J=8.0 Hz, 2H), 4.10 (q, J=7.0 Hz, 2H), 3.91 (t, J=8.0 Hz, 2H), 3.85 (t, J=8.0 Hz, 2H), 2.31 (t, J=8.0 Hz, 2H), 2.03 (dt, J=8.0, 8.0 Hz, 2H), 1.73 (tt, J=8.0 Hz, 2H), 1.63-1.55 (m, 2H), 1.46 (tq, J=8.0, 8.0 Hz, 2H), 1.24 (t, J=7.0 Hz, 3H), 0.95 (t, J=8.0 Hz, 3H); MS (ES) m/z: 377 (M+Na$^+$).

Compound c-3 (71 mg, 0.20 mmol) in THF/MeOH/H$_2$O (4:1:1 v/v/v, 6 mL) was treated with LiOH (1M in H$_2$O, 1.0 mL, 1.0 mmol). The mixture was stirred at room temperature overnight. Aqueous 1N HCl solution was added to neutralize the reaction mixture and then it was extracted with EtOAc thrice. The combined extracts were washed with brine and dried over $Na_2SO_4$. Concentration and chromatograph on silica gel (20:1 $CH_2Cl_2$/MeOH) gave 51 mg (78%) of the acid 30 as colorless oil. $^1$H NMR (300 MHz, $CDCl_3$) δ730-7.15 (m, 5H), 7.12 (d, J=9.0 Hz, 2H), 6.80 (d, J=9.0 Hz, 2H), 3.91 (t, J=6.0 Hz, 2H), 3.84 (t, J=9.0 Hz, 2H), 2.35 (t, J=7.5 Hz, 2H), 2.05 (dt, J=9.0, 7.5 Hz, 2H), 1.75 (tt, J=6.0 Hz, 2H), 1.64-1.54 (m, 2H), 1.47 (tq, J=6.0, 7.5 Hz, 2H), 0.95 (t, J=7.5 Hz, 3H); MS (ES) m/z: 349 (M+Na$^+$).

Compounds 1 through 30 in Table 1 below were prepared according to the methods described by the Schemes and Examples described herein.

TABLE 1

| Cpd No. | Structure |
|---|---|
| 1 | 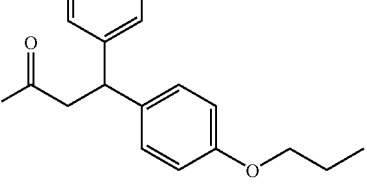 |
| 2 | 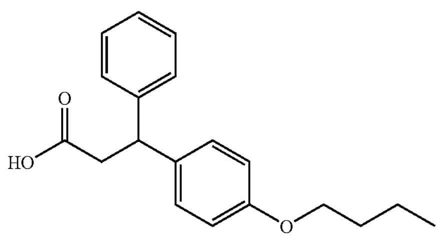 |
| 3 | 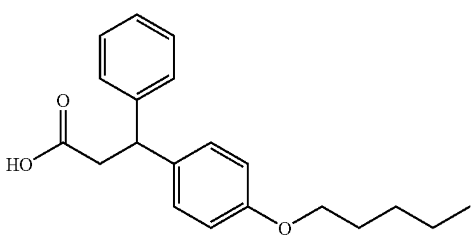 |
| 4 | 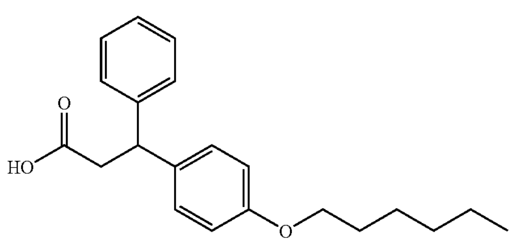 |
| 5 | 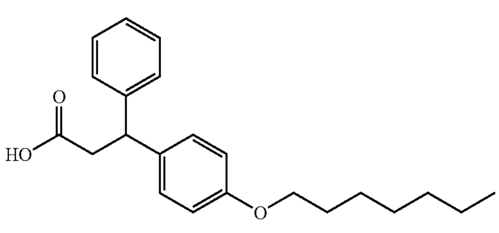 |

TABLE 1-continued

| Cpd No. | Structure |
|---|---|
| 6 | 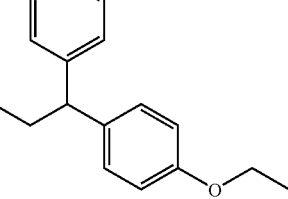 |
| 7 | 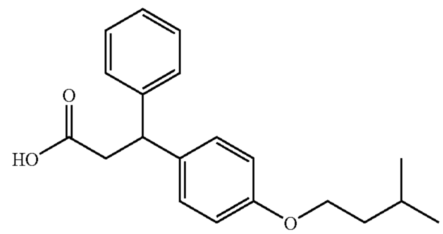 |
| 8 | 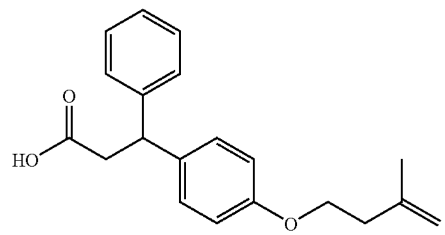 |
| 9 | 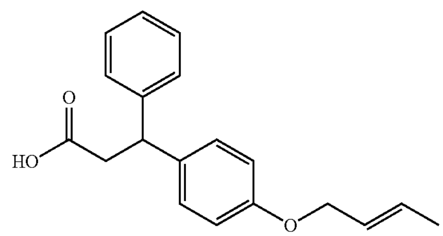 |
| 10 | 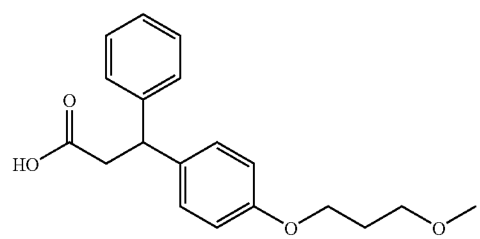 |
| 11 | 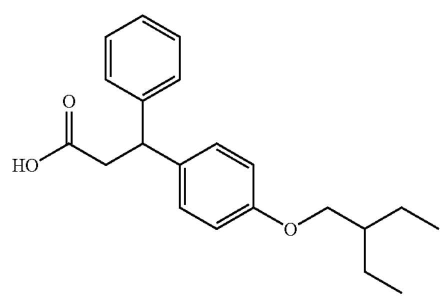 |

TABLE 1-continued

| Cpd No. | Structure |
|---|---|
| 12 | 3-phenyl-3-[4-(2-methylbutoxy)phenyl]propanoic acid |
| 13 | 3-phenyl-3-[4-(4-methylcyclohexyloxy)phenyl]propanoic acid |
| 14 | (A)-3-phenyl-3-[4-(2-ethylbutoxy)phenyl]propanoic acid |
| 15 | (B)-3-phenyl-3-[4-(2-ethylbutoxy)phenyl]propanoic acid |
| 16 | (B)-3-phenyl-3-[4-((S)-2-methylbutoxy)phenyl]propanoic acid |
| 17 | (B)-3-phenyl-3-[4-((S)-2-methylbutoxy)phenyl]propanoic acid |
| 18 | (A)-3-phenyl-3-[4-((S)-2-methylbutoxy)phenyl]propanoic acid |
| 19 | (A)-3-phenyl-3-[4-((R)-2-methylbutoxy)phenyl]propanoic acid |
| 20 | 3-(3-fluorophenyl)-3-(4-butoxyphenyl)propanoic acid |
| 21 | 3-[3-(trifluoromethyl)phenyl]-3-(4-butoxyphenyl)propanoic acid |

TABLE 1-continued

| Cpd No. | Structure |
|---|---|
| 22 | 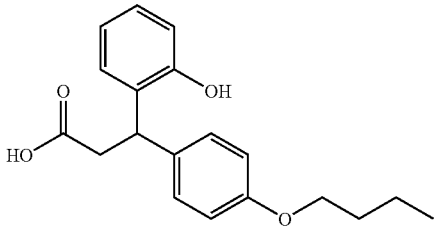 |
| 23 | 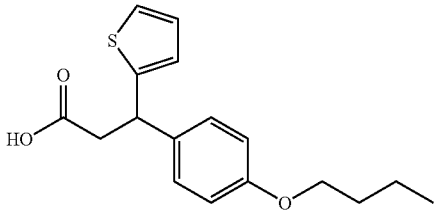 |
| 24 | 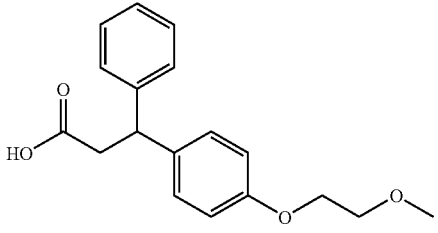 |
| 25 | 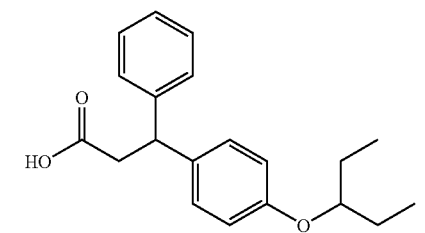 |
| 26 | 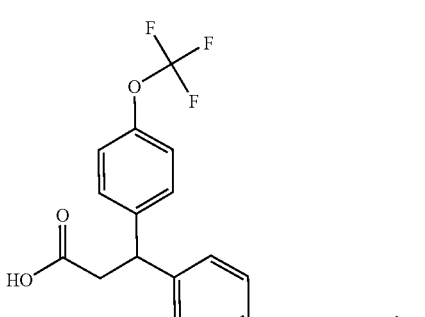 |
| 27 | 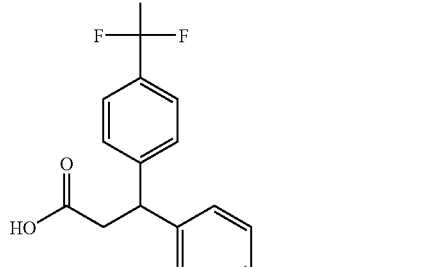 |
| 28 | 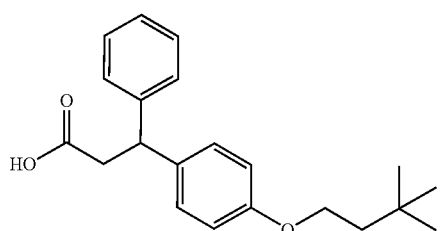 |
| 29 | 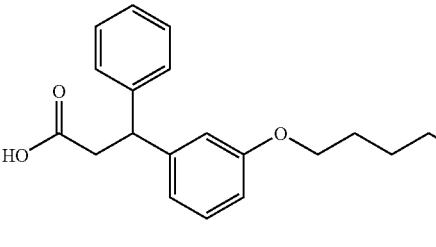 |
| 30 | 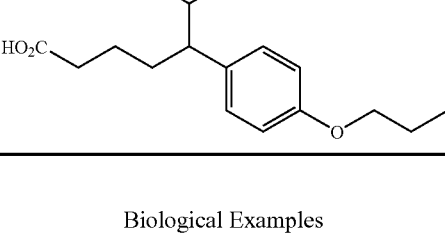 |

Biological Examples

GPR40 In Vitro Assay

To identify agonists of GPR40 receptor, the following assay was used to measure FFA-induced calcium mobilization in transfected cell lines HEK293/hGPR40-32:

Plate 20,000 cell/well in Corning 384 well plate (Cat# 3712);
Incubate over night (16 to 24 hours);
Remove medium;
Add 40 μl of 1×BD dye (1× signal enhancer, 1× calcium indicator dye, 1× probenecid, 0.01% BSA in DMEM/F12 media without Phenol Rad);
Incubate 30 minutes at 37° C. and 15 minutes at RT;
Read with the FDSS6000 System;
Add 20 μl of test compound (in 0.01% BSA in DMEM/F12 media without Phenol Rad);
Read for 5 minutes;

Add 20 μl of 40 μM linolenic acid or GPR40 agonist (in 0.01% BSA in DMEM/F12 media without Phenol Rad);
Read for 2 minutes.
Percentage Inhibition and/or $ED_{50}$ were calculated following conventional methods. Representative results are shown in Table 2 below:

TABLE 2

In vitro data of representative compounds of the invention

| Compound No. | $ED_{50}$ (μM) |
|---|---|
| 1 | 3.70 |
| 2 | 1.43, 0.96 |
| 3 | 3.3, 4.2, 1.4 |
| 4 | 2.88 |
| 5 | 4.26 |
| 6 | 3.16 |
| 7 | 1.81, 2.58, 1.18 |
| 8 | 2.71 |
| 9 | 2.71 |
| 10 | 7.58 |
| 11 | 0.64 |
| 12 | 0.33, 0.26 |
| 13 | 7.32 |
| 14 | >30 |
| 15 | 0.85 |
| 16 | 0.71 |
| 17 | 0.56 |
| 18 | >10 |
| 19 | >10 |
| 20 | 1.44 |
| 21 | 2.84 |
| 22 | 4.8 |
| 23 | 0.96, 1.61 |
| 24 | >10 |
| 25 | >10 |
| 26 | >10 |
| 27 | >10 |
| 28 | >10 |
| 29 | >10 |
| 30 | >10 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of Formula (I)

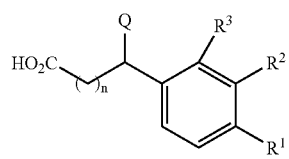

wherein
$R^1$ is —O—$R^4$, or when $R^2$ is —O—$R^5$, $R^1$ is H;
$R^2$ is selected from H, halo, cyano, acetyl, $C_{1-3}$alkyl optionally substituted with halo, $C_{1-3}$alkoxy optionally substituted with halo, and —O—$R^5$;
$R^3$ is selected from H, halo, cyano, acetyl, $C_{1-3}$alkyl optionally substituted with halo, and $C_{1-3}$alkoxy optionally substituted with halo;
$R^4$ and $R^5$ are each independently selected from $C_{3-8}$alkyl optionally substituted with halo or cyano, $C_{3-8}$alkenyl optionally substituted with halo, $C_{3-8}$alkynyl optionally substituted with halo, $C_{3-8}$cycloalkyl optionally substituted with $C_{1-3}$alkyl, $C_{1-4}$alkoxy-$C_{3-5}$alkyl;
Q is selected from phenyl,

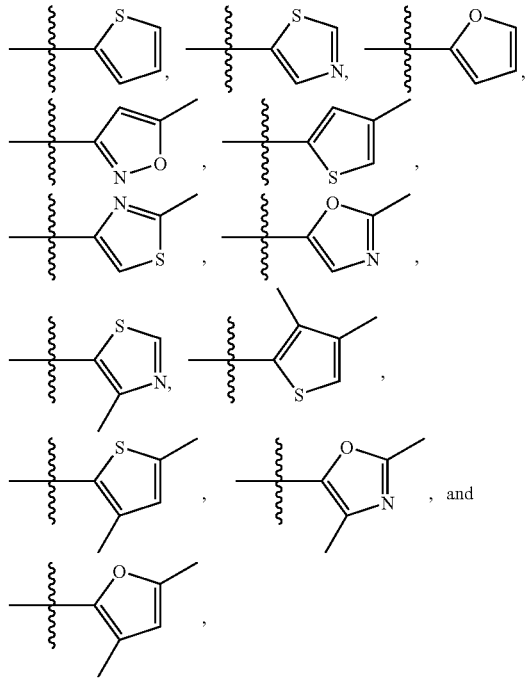

said Q being substituted with 0-2 groups independently selected from halo, $C_{1-3}$alkyl, halo substituted $C_{1-3}$alkyl, $C_{1-3}$alkoxy, halo substituted $C_{1-3}$alkoxy, cyano, acetyl or hydroxy; and
n is 1, 2 or 3;
or an optical isomer, enantiomer, diastereomer, racemate, or pharmaceutically acceptable salt thereof.

2. The compound according to claim 1 wherein
$R^1$ is —O—$R^4$;
$R^2$ is selected from H, halo, cyano, acetyl, $C_{1-3}$alkyl optionally substituted with halo, and $C_{1-3}$alkoxy optionally substituted with halo;
$R^3$ is selected from H, halo, cyano, acetyl, $C_{1-3}$alkyl optionally substituted with halo, and $C_{1-3}$alkoxy optionally substituted with halo;
$R^4$ is selected from $C_{3-8}$alkyl optionally substituted with halo or cyano, $C_{3-8}$alkenyl optionally substituted with halo, $C_{3-8}$alkynyl optionally substituted with halo, $C_{3-8}$cycloalkyl optionally substituted with $C_{1-3}$alkyl, $C_{1-4}$alkoxy-$C_{3-5}$alkyl;
Q is selected from phenyl,

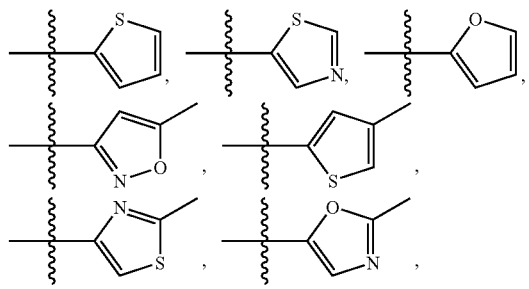

-continued

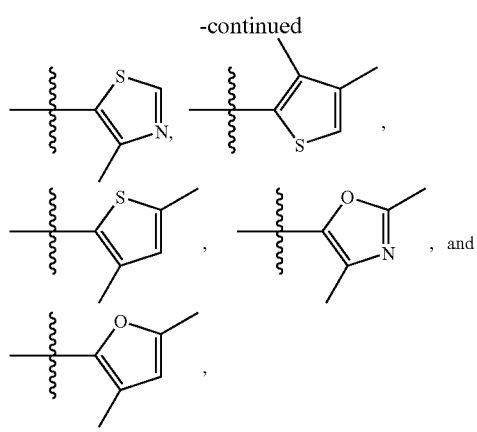

said Q being substituted with 0-2 groups independently selected from halo, $C_{1-3}$alkyl, halo substituted $C_{1-3}$alkyl, $C_{1-3}$alkoxy, halo substituted $C_{1-3}$alkoxy, cyano, acetyl or hydroxy; and
n is 1;
or an optical isomer, enantiomer, diastereomer, racemate, or pharmaceutically acceptable salt thereof.

3. The compound according to claim 2 wherein $R^1$ is —O—$R^4$ wherein $R^4$ is selected from $C_{3-7}$alkyl optionally substituted by halo, methoxy-$C_{3-5}$alkyl-, $C_{3-8}$alkenyl, and $C_{5-6}$cycloalkyl optionally substituted by methyl.

4. The compound according to claim 2 wherein $R^2$ and $R^3$ are both H.

5. The compound according to claim 4 wherein Q is

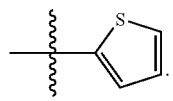

6. The compound according to claim 4 wherein Q is phenyl.

7. The compound according to claim 4 wherein Q is substituted with 0-2 groups selected from halo, $CF_3$, and OH.

8. The compound according to claim 1 wherein
$R^1$ is —O—$R^4$;
$R^2$ and $R^3$ are both H;
$R^4$ is selected from $C_{3-7}$alkyl optionally substituted by halo, methoxy-$C_{3-5}$alkyl-, $C_{3-8}$alkenyl, and $C_{5-6}$cycloalkyl optionally substituted by methyl; and
Q is phenyl or

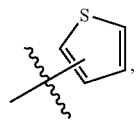

said Q being optionally substituted with 1 or 2 groups independently selected from halo, $CF_3$, or OH;
or an optical isomer, enantiomer, diastereomer, racemate, or pharmaceutically acceptable salt thereof.

9. A compound selected from the group consisting of
3-Phenyl-3-(4-propoxy-phenyl)-propionic acid;
3-(4-Butoxy-phenyl)-3-phenyl-propionic acid;
3-(4-Pentyloxy-phenyl)-3-phenyl-propionic acid;
3-(4-Hexyloxy-phenyl)-3-phenyl-propionic acid;
3-(4-Heptyloxy-phenyl)-3-phenyl-propionic acid;
3-Phenyl-3-[4-(4,4,4-trifluoro-butoxy)-phenyl]-propionic acid;
3-[4-(3-Methyl-but-3-enyloxy)-phenyl]-3-phenyl-propionic acid;
3-[4-(3-Methyl-butoxy)-phenyl]-3-phenyl-propionic acid;
3-(4-But-2-enyloxy-phenyl)-3-phenyl-propionic acid;
3-[4-(3-methoxy-propoxy)-phenyl]-3-phenyl-propionic acid;
3-(3-Pentyloxy-phenyl)-3-phenyl-propionic acid;
5-(4-Butoxy-phenyl)-5-phenyl-pentanoic acid;
3-[4-(4-Methyl-cyclohexyloxy)-phenyl]-3-phenyl-propionic acid;
3-[4-(2-Ethyl-butoxy)-phenyl]-3-phenyl-propionic acid;
3-[4-(2-Methyl-butoxy)-phenyl]-3-phenyl-propionic acid;
3-(4-Butoxy-phenyl)-3-(3-fluoro-phenyl)-propionic acid;
3-(4-Butoxy-phenyl)-3-(3-trifluoromethyl-phenyl)-propionic acid;
3-(4-Butoxy-phenyl)-3-(2-hydroxy-phenyl)-propionic acid;
3-(4-Butoxy-phenyl)-3-thiophen-2-yl-propionic acid;
3-[4-(2-Methoxy-ethoxy)-phenyl]-3-phenyl-propionic acid;
3-[4-(1-Ethyl-propoxy)-phenyl]-3-phenyl-propionic acid;
3-(4-Butoxy-phenyl)-3-(4-trifluoromethoxy-phenyl)-propionic acid;
3-(4-Butoxy-phenyl)-3-(4-trifluoromethyl-phenyl)-propionic acid;
3-[4-(3,3-Dimethyl-butoxy)-phenyl]-3-phenyl-propionic acid; and
an optical isomer, enantiomer, diastereomer, racemate, or pharmaceutically acceptable salt thereof.

10. The compound according to claim 9 selected from the group consisting of

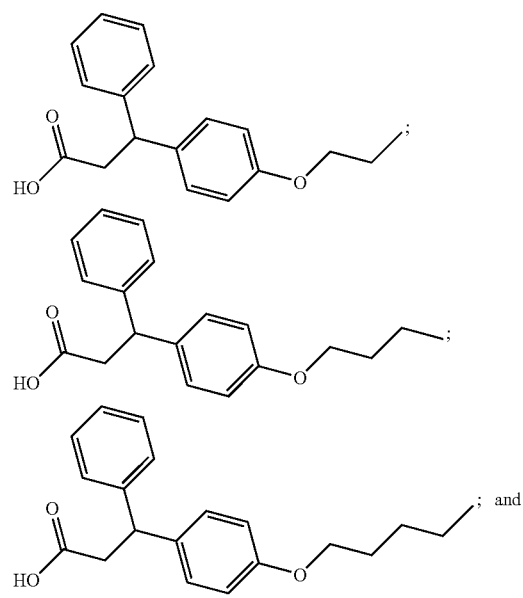

-continued

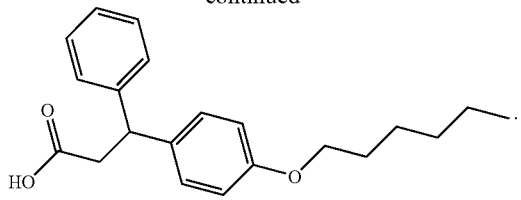

11. A pharmaceutical composition comprising a compound according to claim 1 admixed with a pharmaceutically acceptable carrier, excipient or diluent.

12. A method of treating a disease or condition in a mammal which disease or condition is affected by the modulation of GPR40 wherein the disease or condition is selected from the group consisting of insulin resistance, hyperglycemia, obesity, and diabetes, which method comprises administering to a mammal in need of such treatment a therapeutically effective amount of a compound of claim 1.

13. A method of stimulating glucose-induced insulin secretion in a subject, which method comprises administering to a subject in need thereof a therapeutically effective amount of a compound or a pharmaceutically acceptable salt according to claim 1.

14. The method of claim 12 wherein said therapeutically effective amount comprises a dose range of from about 0.1 mg to about 2,000 mg.

15. The method of claim 12 wherein said therapeutically effective amount comprises a dose range of from about 1 mg to about 1000 mg.

16. The method of claim 12 wherein said therapeutically effective amount comprises a dose range of from about 50 mg to about 1000 mg.

17. A kit comprising in one or more containers an amount of the composition of claim 11 effective to treat a disease or condition selected from the group consisting of insulin resistance, hyperglycemia, obesity, and diabetes.

\* \* \* \* \*